(12) United States Patent
Bryans et al.

(10) Patent No.: US 6,864,390 B2
(45) Date of Patent: Mar. 8, 2005

(54) METHOD FOR THE STEREOSELECTIVE SYNTHESIS OF CYCLIC AMINO ACIDS

(75) Inventors: Justin Stephen Bryans, Balsham (GB); David Clive Blakemore, Cambridge (GB); Sophie Caroline Williams, Cambridge (GB)

(73) Assignee: Warner-Lambert Company, Morris Plains, NJ (US)

( * ) Notice: Subject to any disclaimer, the term of this patent is extended or adjusted under 35 U.S.C. 154(b) by 220 days.

(21) Appl. No.: 10/149,160

(22) PCT Filed: Nov. 30, 2000

(86) PCT No.: PCT/US00/32570

§ 371 (c)(1),
(2), (4) Date: Jun. 6, 2002

(87) PCT Pub. No.: WO01/42190

PCT Pub. Date: Jun. 14, 2001

(65) Prior Publication Data

US 2003/0069438 A1 Apr. 10, 2003

Related U.S. Application Data

(60) Provisional application No. 60/169,602, filed on Dec. 8, 1999.

(51) Int. Cl.[7] .................. C07C 63/33; C07C 61/16; C07C 61/20
(52) U.S. Cl. .................. 562/491; 562/503; 562/504
(58) Field of Search .................. 562/491, 503, 562/504

(56) References Cited

FOREIGN PATENT DOCUMENTS

WO          9921824          5/1999

OTHER PUBLICATIONS

PCT Search Report, PCT/US00/32570.
Herz, "Azulenes. VII. A Novel Rearrangement in the Synthesis of Azulenes", *Journal of the American Chemical Society*, vol. 78, No. 7, pp. 1485–1494, 1956.

Primary Examiner—Johann Richter
Assistant Examiner—Paul A. Zucker
(74) Attorney, Agent, or Firm—Scully, Scott, Murphy & Presser

(57) ABSTRACT

The instant invention is a route to stereospecific 3-substituted 5-membered ring isomers of Formula (A). The final products are useful as agents in the treatment of epilepsy, faintness attacks, hypokinesia, cranial disorders, neurodegenerative disorders, depression, anxiety, panic, pain, neuropathological disorders, gastrointestinal disorders such as irritable bowel syndrome (IBS), inflammation especially arthritis, sleep disorders, premenstrual syndrome, and hot flashes. The invention provides novel routes to synthesize steroselectively analogs of gabapentin (Neurontin®) of Formulas (I), (II), (III) and (IV) wherein R is $C_1$–$C_{10}$ alkyl or $C_3$–$C_{10}$ cycloalkyl and pharmaceutically acceptable salts thereof.

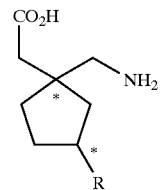

(A)

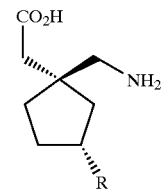

(I)

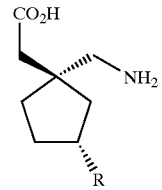

(II)

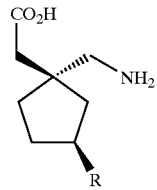

(III)

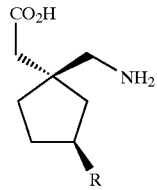

(IV)

46 Claims, No Drawings

METHOD FOR THE STEREOSELECTIVE SYNTHESIS OF CYCLIC AMINO ACIDS

This application is a 371 application of PCT/US00/32570 filed Nov. 30, 2000, which claims the benefit of priority to U.S. provisional application Ser. No. 60/169,602 filed Dec. 8, 1999.

BACKGROUND OF THE INVENTION

Compounds of formula:

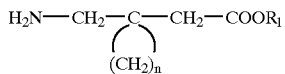

wherein $R_1$ is hydrogen or a lower alkyl radical and n is 4, 5, or 6 are known in U.S. Pat. No. 4,024,175 and its divisional U.S. Pat. No. 4,087,544. The uses disclosed are: protective effect against cramp induced by thiosemicarbazide; protective action against cardiazole cramp; the cerebral diseases, epilepsy, faintness attacks, hypokinesia, and cranial traumas; and improvement in cerebral functions. The compounds are useful in geriatric patients. The patents are hereby incorporated by reference.

U.S. Ser. No. 09/485,382 filed Feb. 8, 2000 teaches in part compounds of Formula I:

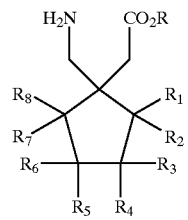

or a pharmaceutically acceptable salt thereof wherein R is hydrogen or a lower alkyl; and $R_1$ to $R_8$ are each independently selected from hydrogen, straight or branched alkyl of from 1 to 6 carbon atoms, phenyl, benzyl, fluorine, chlorine, bromine, hydroxy, hydroxymethyl, amino, aminomethyl, trifluoromethyl, —$CO_2H$, —$CO_2R_{15}$, —$CH_2CO_2H$, —$CH_2CO_2R_{15}$, —$OR_{15}$ wherein $R_{15}$ is a straight or branched alkyl of from 1 to 6 carbons, phenyl, or benzyl, and $R_1$ to $R_8$ are not simultaneously hydrogen. This patent application is hereby incorporated by reference.

U.S. Pat. No. 5,929,116 describes endothelin antagonists of formulas:

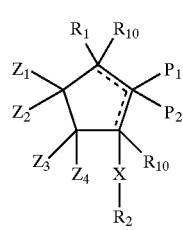

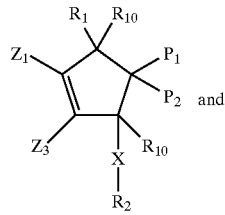

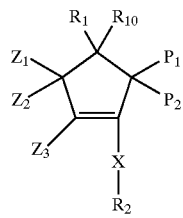

wherein $R_1$ is —$X(CH_2)_nAr$;

$R_2$ is Ar;

$P_1$ is —$X(CH_2)_nR_8$;

$P_2$ is —$X(CH_2)_nR_8$, or —$XR_9Y$;

$R_3$ and $R_5$ are independently hydrogen, $R_{11}$, OH, $C_{1-8}$ alkoxy, $S(O)_qR_{11}$, $N(R_6)_2$, Br, F, I, Cl, $CF_3$, $NHCOR_6$, —$R_{11}CO_2R_7$, —$XR_9$—Y, or —$X(CH_2)_nR_8$ wherein each methylene group within —$X(CH_2)_nR_8$ may be unsubstituted or substituted by one or two —$(CH_2)_nAr$ groups;

$R_4$ is hydrogen, $R_{11}$, OH, $C_{1-5}$ alkoxy, $S(O)_qR_{11}$, $N(R_6)_2$, —$X(R_{11})$, Br, F, I, Cl, or $NHCOR_6$ wherein the $C_{1-5}$ alkoxy may be unsubstituted or substituted by OH, methoxy, or halogen;

$R_6$ is independently hydrogen or $C_{1-4}$ alkyl;

$R_7$ is independently hydrogen, $C_{1-6}$ alkyl, or $(CH_2)_nAr$;

$R_8$ is hydrogen, $R_{11}$, $CO_2R_7$, $PO_3H_2$, $SO_2NR_7R_{11}$, $NR_7SO_2R_{11}$, $P(O)(OH)R_7$, CN, —$C(O)N(R_6)_2$, tetrazole, or $OR_6$;

$R_9$ is $C_{1-10}$ alkyl, $C_{2-10}$ alkenyl, or phenyl, all of which may be unsubstituted or substituted by one or more OH, $N(R_6)_2$, COOH, >C=O, halogen, or $XC_{1-5}$ alkyl;

$R_{10}$ is $R_3$ or $R_4$;

$R_{11}$ is $C_{1-8}$ alkyl, $C_{2-8}$ alkenyl, $C_{2-8}$ alkynyl, all of which may be unsubstituted or substituted by one or more OH, $CH_2OH$, $N(R_6)_2$, or halogen;

X is $(CH_2)_n$, O, $NR_6$, or $S(O)_q$;

Y is $CH_3$ or $X(CH_2)_nAr$;

Ar is:

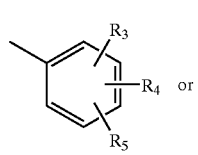

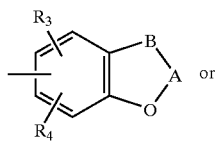

naphthyl, indolyl, pyridyl, thienyl, oxazolidinyl, oxazolyl, thiazolyl, isothiazolyl, pyrazolyl, triazolyl, tetrazolyl, imidazolyl, imidazolidinyl, thiazolidinyl, isoxazolyl, oxadiazolyl, thiadiazolyl, morpholinyl, piperidinyl, piperazinyl, pyrrolyl, or pyrimidyl; all of which may be unsubstituted or substituted by one or more $R_3$ or $R_4$ groups;

A is >C=O, or $[C(R_6)_2]_m$;

B is —$CH_2$— or —O—;

$Z_1$, $Z_2$, $Z_3$, and $Z_4$ are independently hydrogen, $C_{1-8}$ alkyl, $C_{2-8}$ alkenyl, $C_{2-8}$ alkynyl, OH, $C_{1-8}$ alkoxy, $S(O)_q C_{1-8}$ alkyl, $N(R_6)_2$, Br, F, I, Cl, $NHCOR_6$, —$X(CH_2)_n R_8$, $XR_9Y$, phenyl, benzyl, or $C_{3-6}$ cycloalkyl wherein the $C_{1-8}$ alkyl, $C_{2-8}$ alkenyl, or $C_{2-8}$ alkynyl may be optionally substituted by COOH, OH, $CO(CH_2)_n CH_3$, $CO(CH_2)_n CH_2 N(R_6)_2$, or halogen;

q is zero, one, or two;

n is an integer from 0 to 6;

m is 1, 2, or 3;

and the dotted line in Formula (I) indicates the optional presence of a double bond; or a pharmaceutically acceptable salt thereof; provided that when the optional double bond is present, there is only one $R_{10}$, there is no $P_1$, and $P_2$ is not $NR_6R_9Y$;

X is not $NR_6$, and $Z_3$ is not OH or $N(R_6)_2$ in Formula (III);

$Z_1$ and $Z_3$ are not OH, $N(R_6)_2$, or Iodine in Formula (II);

when the optional double bond is present in Formula (I) and X—$R_2$ is attached to the double bond, X is not $NR_6$;

when the optional double bond is present in Formula (I) and $R_1$ is attached directly to the double bond, $R_1$ is not $NR_6Ar$;

when $R_3$, $R_5$, $Z_1$, $Z_2$, or $Z_3$ is $X(CH_2)_n R_8$ and n is not zero, X is oxygen or $NR_6$ when $R_8$ is $OR_6$ or $CO_2H$.

Also included in the invention are pharmaceutically acceptable salts of the active compounds.

Most or all of the desired pharmacological activity of a compound comprised of two or more stereoisomers frequently resides in just one of the stereoisomers. The other stercoisomer(s) typically is inactive at best or exhibits undesirable side effects such as, for example, toxicity. Therefore where a compound is comprised of two or more stereoisomers, it is important, and sometimes mandatory, to develop a method of selectively preparing the beneficial stereoisomer in a form that is free from, or almost free from, contamination by the other inactive or harmful stercoisomer(s). However, usually it is very difficult to discover a method for the preparation of a beneficial stereoisomer in a form that is free from, or almost free from, contamination by the other inactive or harmful stereoisomer(s). Unexpectedly, we have invented novel preparations of certain important 3-substituted cyclopentyl-containing, amino acid analogs of gabapentin, a marketed anticonvulsant, which provide the desirable stereoisomers with a high degree of stereochemical purity.

None of the above teach the synthesis of the instant invention.

SUMMARY OF THE INVENTION

The instant invention encompasses novel synthetic routes for the preparation of important 3-substituted cyclopentyl-based analogs of gabapentin and pharmaceutically acceptable salts thereof. Gabapentin, marketed under the trade name Neurontin® for the treatment of seizure disorders, particularly epilepsy, provides well-known medical benefits to patients in need of such treatment. The instant invention encompasses novel synthetic routes for the preparation of 3-substituted cyclopentyl-based analogs of gabapentin and pharmaceutically acceptable salts thereof that enable the synthesis of each stereoisomer of these analogs with a high degree of stereochemical purity. These routes provide access to pure stereoisomers of Formulas I, II, III, and IV:

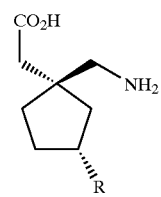

I

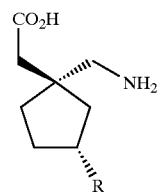

II

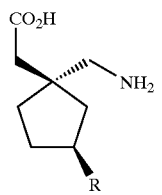

III

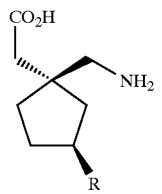

IV wherein R is $C_1$–$C_{10}$ alkyl or $C_3$–$C_{10}$ cycloalkyl.

Further, the invention encompasses the key intermediates of formulas (6) and (26). Still further, the invention provides novel synthetic routes for the preparation of compounds of formulas (6) and (26). The routes enable the synthesis of each stereoisomer of compounds of formulas (6) and (26) with a high degree of stereochemical purity. These routes provide access to pure stereoisomers of formulas (6) and (26) wherein R is $C_1$–$C_{10}$ alkyl or $C_3$–$C_{10}$ cycloalkyl.

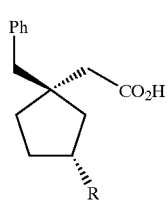 (6)

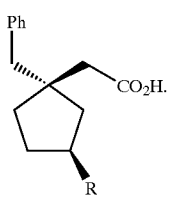 (26)

The invention provides a process for the preparation of a compound of Formula I:

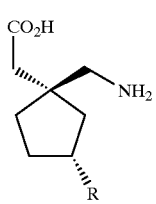 I wherein R is $C_1$–$C_{10}$ alkyl or $C_3$–$C_{10}$ cycloalkyl, and pharmaceutically acceptable salts thereof, which comprises:
a) adding a cyanoacetate of formula (A)

wherein $R_1$ is alkyl or benzyl, to a mixture of a chiral cyclopentanone of formula (1)

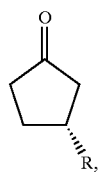

a solvent, a carboxylic acid, and a Knoevenagel reaction catalyst, and stirring the mixture in the presence of a means of removing water to produce the alkene of formula (2):

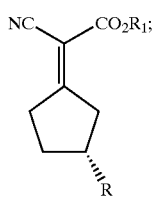

b) adding the product of Step a) above to a mixture of benzylmagnesium chloride, benzylmagnesium bromide, or benzylmagnesium iodide, in a solvent to produce the addition products of formulas (3a):

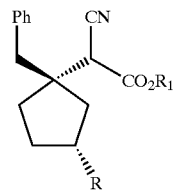

and (3b)

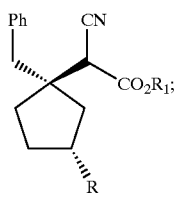

c) adding the products of Step b) above to a mixture of a base selected from potassium hydroxide, sodium hydroxide, lithium hydroxide, or cesium hydroxide in a solvent and stirring, and then acidifying to produce the carboxylic acids of formulas (4a):

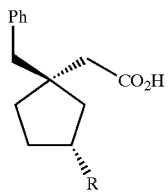

and (4b):

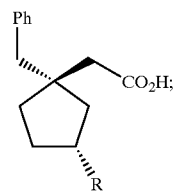

or adding the products of Step b) above to an acid mixture and stirring to produce the carboxylic acids of formulas (4a):

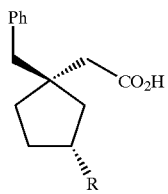

and (4b)

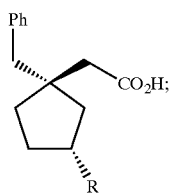

d) contacting the products of Step c) above with an amine in a solvent, and recrystallizing the salt so formed to produce the enriched diastereomer of formula (5):

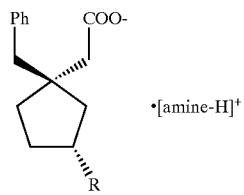

as the amine salt;

e) converting the product of Step d) to a carboxylic acid of formula (6):

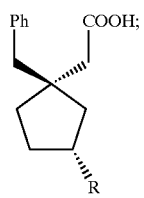

f) adding the product of Step e) to a mixture of iodomethane, a solvent, and a base, and stirring to produce the ester of formula (7):

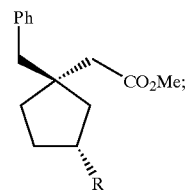

or adding the product of Step e) to methanol and an acid to produce the ester of formula (7):

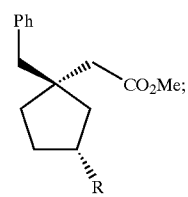

or adding the product of Step e) above to trimethylsilyldiazo-methane and methanol in a solvent to produce the ester of formula (7):

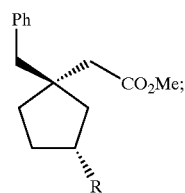

or adding the product of Step e) to a solution of diazomethane or trimethylsilyl-diazomethane in a solvent to produce ester of formula (7):

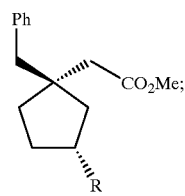

g) adding the product of Step f) to a mixture of carbon tetrachloride or ethyl acetate, and acetonitrile, water, sodium periodate, and ruthenium(III) chloride, and stirring to produce the carboxylic acid of formula (8):

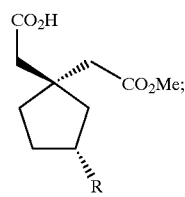

h) adding the product of Step g) to a mixture of a tertiary amine base, a solvent, and diphenylphosphoryl azide (DPPA), and stirring to produce the isocyanate of formula (9):

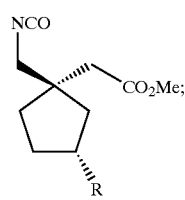

or adding the product of Step g) above to ethyl chloroformate or isobutyl chloroformate and a base in a solvent at a temperature of from −40° C. to 78° C., followed by adding a solution of sodium azide in water and tetrahydrofuran or acetone, followed by adding toluene or benzene, and refluxing to produce the isocyanate of formula (9):

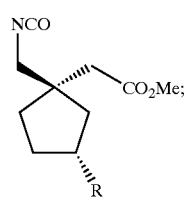

i) adding the product of Step h) to a mixture of a solvent and methanol, and stirring to produce the carbamate of formula (10):

j) adding the product of Step i) to a mixture of a solvent and aqueous hydrochloric acid, and stirring to produce a compound of formula (Ia):
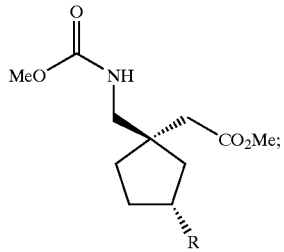
k) converting the product of Step j) to a compound of formula (I):
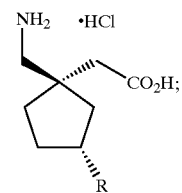
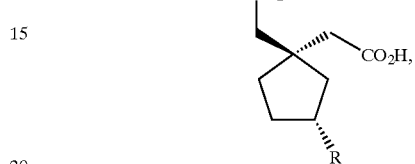
and further converting, if desired, to a pharmaceutically acceptable salt by known means.
This process is outlined in Scheme 1.
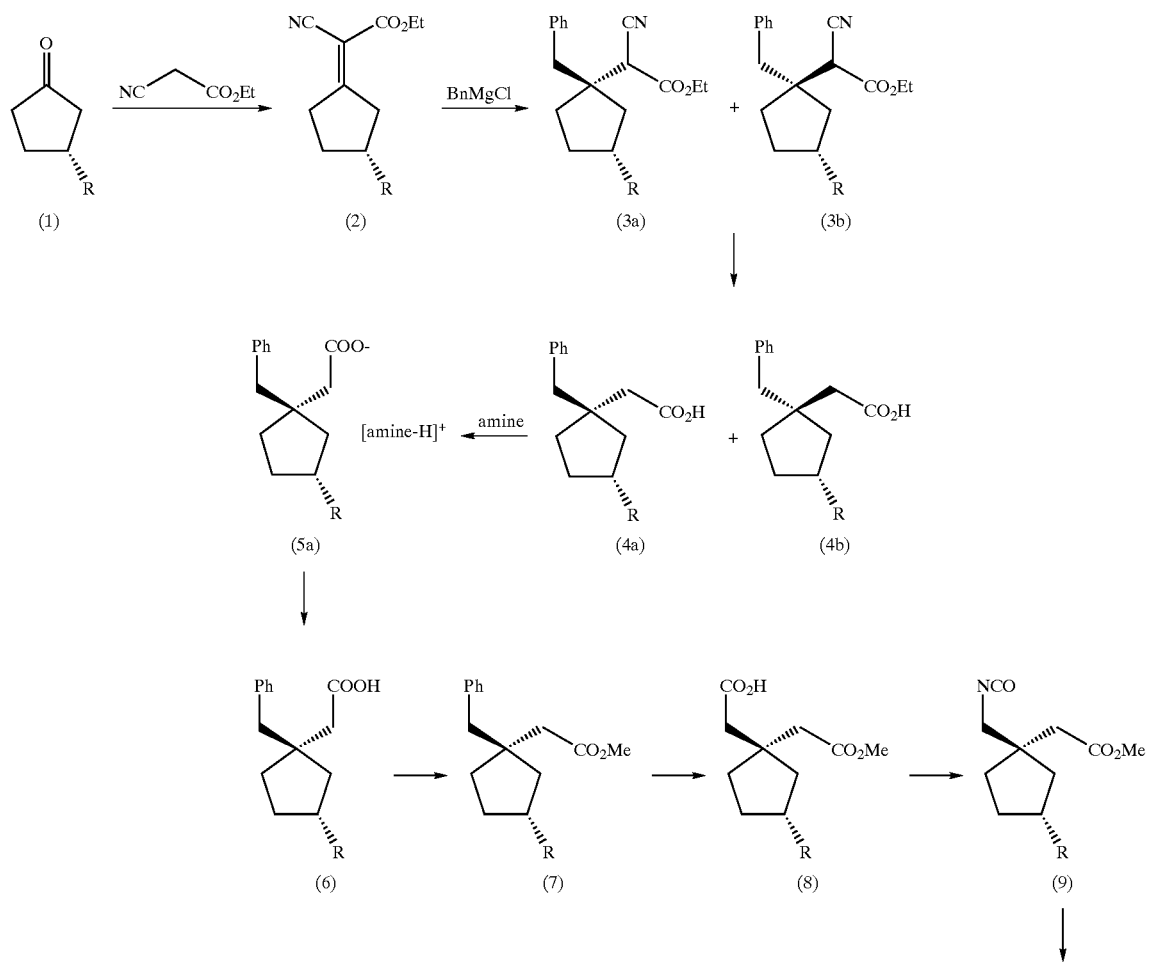

-continued

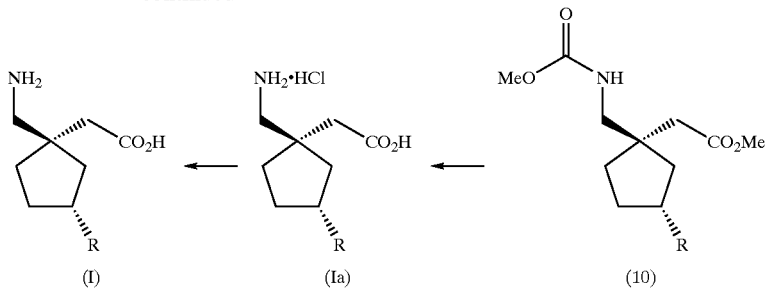

Preferred is a process for the preparation of a compound of Formula I wherein R is $C_1$–$C_{10}$ alkyl or $C_3$–$C_{10}$ cycloalkyl, and pharmaceutically acceptable salts thereof, which comprises:

a) adding a cyanoacetate of formula (A):

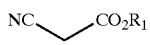

wherein $R_1$ is selected from methyl, ethyl, n-propyl, isopropyl, n-butyl, iso-butyl, sec-butyl, tert-butyl, and benzyl to a mixture of a chiral cyclopentanone of formula (1):

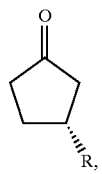

a solvent selected from tetrahydrofuran, 1,4-dioxane, tert-butylmethylether, chloroform, dichloromethane, acetonitrile, ethyl ether, ethyl acetate, hexanes, N,N-dimethylformamide, dimethylsulfoxide, ethanol, tert-butanol, toluene, benzene, xylenes, and n-heptane, acetic acid, and a Knoevenagel reaction catalyst selected from β-alanine, ammonium acetate, and piperidine, and stirring the mixture in the presence of a means of removing water selected from azeotropic distillation, activated molecular sieves, anhydrous magnesium sulfate, anhydrous sodium sulfate, anhydrous sodium carbonate, anhydrous potassium carbonate, anhydrous cesium carbonate, trimethyl orthoformate, and triethyl orthoformate to produce the alkene of formula (2):

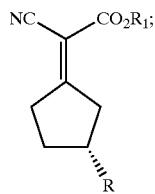

b) adding the product of Step a) above to a mixture of benzylmagnesium chloride, benzylmagnesium bromide, or benzylmagnesium iodide in a solvent selected from tetrahydrofuran, benzene, 1,4-dioxane, hexanes, n-heptane, toluene, diethyl ether, and tert-butyl methyl ether to produce the addition products of formulas (3a):

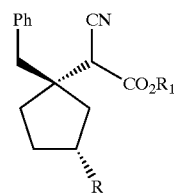

and (3b)

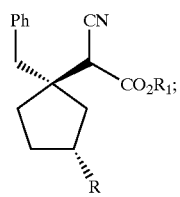

c) adding the products of Step b) above to a mixture of a base selected from potassium hydroxide, sodium hydroxide, lithium hydroxide, and cesium hydroxide in a solvent selected from ethylene glycol, 2-methoxyethyl ether, 1,4-dioxane, and diethylene glycol, and stirring the mixture, and then acidifying to produce the carboxylic acids of formulas (4a):

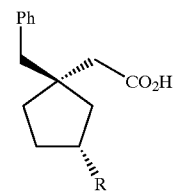

and (4b)

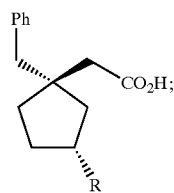

or adding the products of Step b) above to an acid mixture selected from 6–12 M HCl, 12 M $H_2SO_4$, 10%–48% wt/wt hydrobromic acid, and HBr in aqueous acetic acid, and stirring to produce the carboxylic acids of formulas (4a):

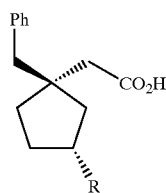

and (4b):

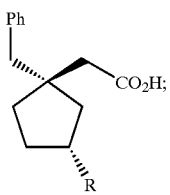

d) contacting the products of Step c) above with an amine selected from (S)-α-methyl-benzylamine, (R)-α-methyl-benzylamine, (R)-(+)-1-(naphthyl)ethylamine, (S)-(+)-1-(naphthyl)ethylamine, triethylamine, diisopropylethylamine, dicyclohexylamine, benzylamine, dibenzylamine, morpholine, N-methylmorpholine, piperidine, N-methylpiperidine, and pyridine in a solvent selected from N,N-dimethylformamide, chloroform, benzene, xylenes, hexanes, acetone, ethanol, methanol, iso-propanol, diethyl ether, dichloromethane, benzene, toluene, n-pentane, n-hexane, n-heptane, ethyl acetate, acetonitrile, tert-butyl methyl ether, tetrahydrofuran, and 1,4-dioxane, and recrystallizing the salt so formed to produce the enriched diastereomer of formula (5):

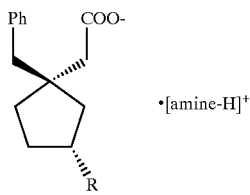

as the amine salt;

e) adding the product of Step d) to a mixture selected from aqueous hydrochloric acid, aqueous sulfuric acid, aqueous acetic acid, hydrochloric acid dissolved in acetic acid, or hydrochloric acid dissolved in acetic acid to which water is added and stirring to produce the carboxylic acid of formula (6):

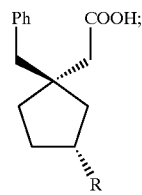

or partitioning the product of Step d) between a mixture of aqueous hydrochloric acid and a solvent selected from chloroform, dichloromethane, ethyl acetate, ethyl ether, tetrahydrofuran, 1,4-dioxane, toluene, and tert-butylmethylether, and drying and evaporating the organic layer to produce the carboxylic acid of formula (6):

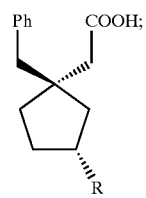

f) adding the product of Step e) above to a mixture of iodomethane, a solvent selected from dichloromethane, chloroform, tetrahydrofuran, toluene, and 1,4-dioxane, and a base selected from 1,8-diazabicyclo[5.4.0]undec-7-ene (DBU), diisopropylethylamine, triethylamine, and 1,5-diazabicyclo[4.3.0]non-5-ene (DBN), and stirring at a temperature of from −40° C. to 110° C. to produce the ester of formula (7):

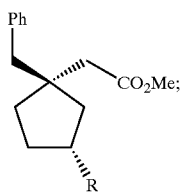

or adding the product of Step e) above to a mixture of methanol and concentrated sulphuric acid, concentrated hydrochloric acid, or hydrogen chloride at a temperature of from 0° C. to 100° C. to produce the ester of formula (7):

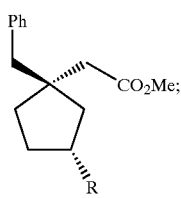

or adding the product of Step e) above to trimethylsilyldiazomethane and methanol in benzene or toluene at a temperature of from −40° C. to 100° C. to produce the ester of formula (7):

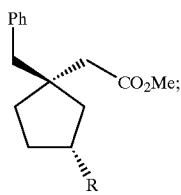

or adding the product of Step e) above to diazomethane or trimethylsilyldiazomethane in a solvent selected from benzene, toluene, dichloromethane, and diethyl ether at a temperature of from −40° C. to 40° C. to give a compound of formula (7):

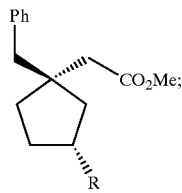

g) adding the product of Step f) to a mixture of carbon tetrachloride or ethyl acetate, and acetonitrile, water, sodium periodate, and ruthenium(III) chloride, and stirring at a temperature from −40° C. to 80° C. to produce the carboxylic acid of formula (8):

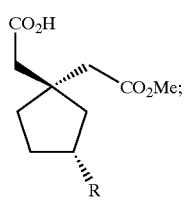

h) adding the product of Step g) above to a mixture of a base selected from triethylamine and diisopropylethylamine, a solvent selected from toluene, benzene, xylenes, tetrahydrofuran, diethyl ether and n-heptane, and diphenylphosphoryl azide (DPPA), and stirring at a temperature of from 0° C. to 150° C. to produce the isocyanate of formula (9):

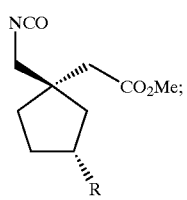

or adding the product of Step g) above to ethyl chloroformate or isobutyl chloroformate, a base selected from triethylamine and diisopropylethylamine, and a solvent selected from tetrahydrofuran, acetone, and diethyl ether at a temperature of from −40° C. to 78° C., followed by adding a solution of sodium azide in water and tetrahydrofuran or acetone, followed by adding toluene or benzene, and refluxing to produce the isocyanate of formula (9):

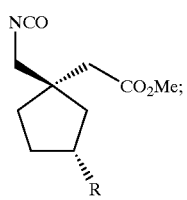

i) adding the product of Step h) to a mixture of a solvent selected from toluene, benzene, xylenes and n-heptane, and methanol, and stirring at a temperature from 0° C. to 150° C. to produce the carbamate of formula (10):

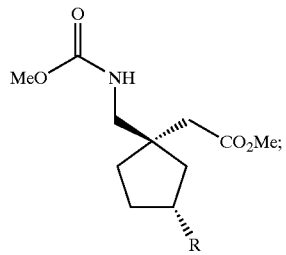

j) adding the product of Step i) to a mixture of a solvent selected from water, acetic acid, and 1,4-dioxane, and aqueous hydrochloric acid at a concentration of from 0.01 M to 12 M, and stirring at a temperature from 0° C. to 115° C. to produce a compound of formula Ia:

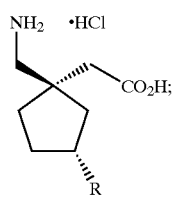

and k) converting the product of Step j) to a compound of Formula I:

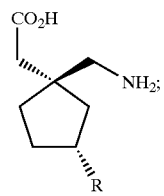

and further converting, if desired, to a pharmaceutically acceptable salt by known means.

More preferred is a process for the preparation of a compound of Formula I wherein R is $C_1$–$C_{10}$ alkyl or $C_3$–$C_{10}$ cycloalkyl, and pharmaceutically acceptable salts thereof, which comprises:

a) adding a cyanoacetate of formula (A)

wherein $R_1$ is ethyl, to a mixture of a chiral cyclopentanone of formula (1):

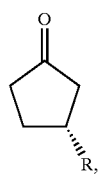

toluene, acetic acid, and a Knoevenagel reaction catalyst which is ammonium acetate, and heating the mixture at reflux over a Dean-Stark trap to produce the alkene of formula (2):

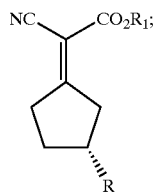

b) adding the product of Step a) above to a mixture of benzylmagnesium chloride in dry tetrahydrofuran at −100° C. to 25° C. to produce the addition products of formulas (3a):

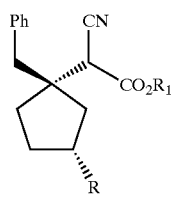

and (3b):

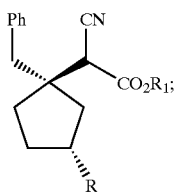

c) adding the products of Step b) above to a mixture of potassium hydroxide in ethylene glycol, and heating the mixture at 100° C. to 200° C., and then acidifying to produce the hydrolysis products of formulas (4a):

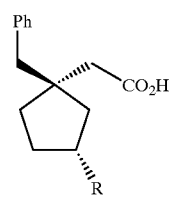

and (4b):

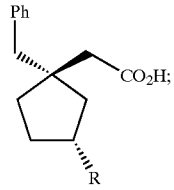

d) contacting the products of Step c) above with (S)-α-methyl-benzylamine in ethyl acetate, and recrystallizing the salt so formed from ethyl acetate to produce the enriched diastereomer of formula (5):

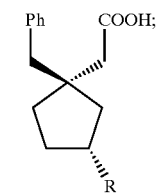

as the (S)-α-methyl-benzylamine salt;

e) adding the product of Step d) to aqueous hydrochloric acid and stirring to produce the carboxylic acid of formula (6):

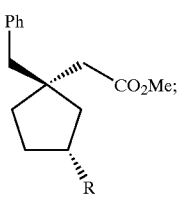

f) adding the product of Step e) to a mixture of iodomethane, dichloromethane, and 1,8-diazabicyclo[5.4.0]undec-7-ene (DBU), and stirring to produce the ester of formula (7):

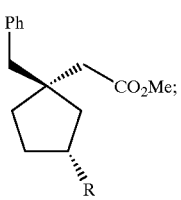

or adding the product of Step e) to methanol and concentrated sulfuric acid to produce the ester of formula (7):

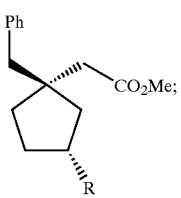

or adding the product of Step e) to a solution of diazomethane or trimethylsilyl-diazomethane in dichloromethane to produce the ester of formula (7):

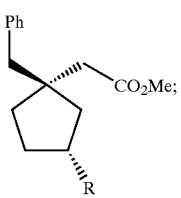

g) adding the product of Step f) to a mixture of carbon tetrachloride or ethyl acetate, and acetonitrile, water, sodium periodate, and ruthenium(III) chloride, and stirring to produce the carboxylic acid of formula (8):

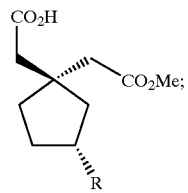

h) adding the product of Step g) to a mixture of triethylamine, toluene, and diphenylphosphoryl azide (DPPA), and refluxing to produce the isocyanate of formula (9):

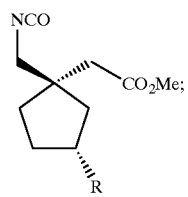

or adding the product of Step g) above to ethyl chloroformate or isobutyl chloroformate and triethylamine in tetrahydrofuran at a temperature of from −40° C. to 78° C., followed by adding a solution of sodium azide in water and tetrahydrofuran, followed by adding toluene or benzene, and refluxing to produce ester of formula (9):

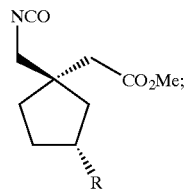

i) adding the product of Step h) to a mixture of methanol and toluene, and refluxing to produce the carbamate of formula (10):

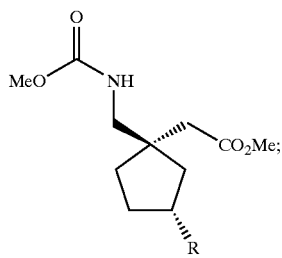

j) adding the product of Step i) to a mixture of 1,4-dioxane and aqueous hydrochloric acid at a concentration of 6 M, and stirring to produce a compound of formula Ia:

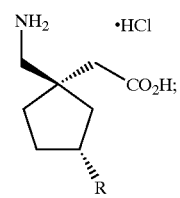

k) converting the product of Step j) to a compound of Formula I:

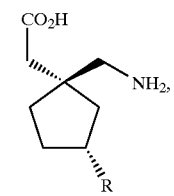

and further converting, if desired, to a pharmaceutically acceptable salt by known means.

Also preferred is a process for the preparation of a compound of Formula I as described above, further characterized in that the intermediate product (9):

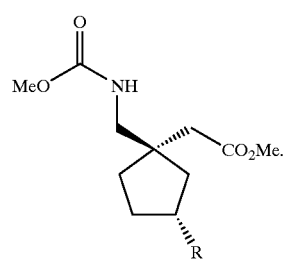

formed is reacted, without isolation, with methanol to produce the carbamate of formula (10):

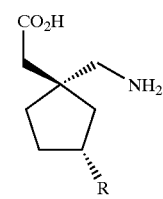

Further, the invention provides a process for the preparation of a compound of Formula II:

II wherein R is $C_1$–$C_{10}$ alkyl or $C_3$–$C_{10}$ cycloalkyl, and pharmaceutically acceptable salts thereof, which comprises:

a) adding a cyanoacetate of formula (A):

wherein $R_1$ is alkyl or benzyl, to a mixture of a chiral cyclopentanone of formula (1):

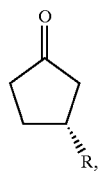

a solvent, a carboxylic acid, and a Knoevenagel reaction catalyst, and stirring the mixture in the presence of a means of removing water to produce the alkene of formula (2):

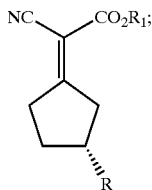

b) adding the product of Step a) above to a mixture of benzylmagnesium chloride, benzylmagnesium bromide, or benzylmagnesium iodide, in a solvent to produce the addition products of formulas (3a):

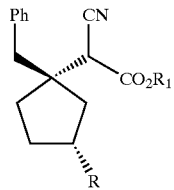

and (3b):

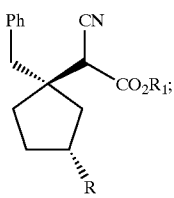

c) adding the products of Step b) above to a mixture of a base selected from potassium hydroxide, sodium hydroxide, lithium hydroxide, and cesium hydroxide and a solvent, and stirring, and then acidifying to produce the carboxylic acids of formulas (4a):

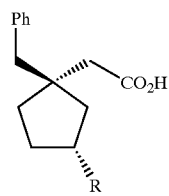

and (4b):

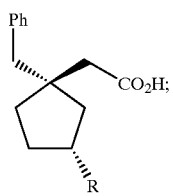

or adding the products of Step b) above to an acid mixture and stirring to produce the carboxylic acids of formulas (4a):

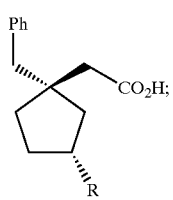

and (4b):

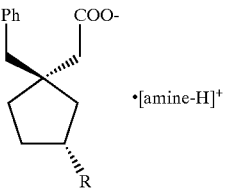

d) contacting the products of Step c) above with an amine in a solvent, and recrystallizing the salt so formed to produce the enriched diastereomer of formula (5):

as the amine salt; and e) converting the product of Step d) to a carboxylic acid of formula (6):

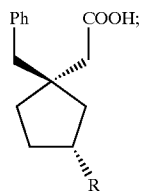

f) adding the product of Step e) to a mixture of a tertiary amine base, a solvent, and diphenylphosphoryl azide (DPPA), and stirring to produce the isocyanate of formula (11):

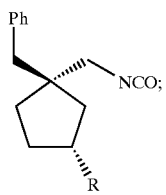

or adding the product of Step e) above to ethyl chloroformate or isobutyl chloroformate and a base in a solvent at a temperature of from −40° C. to 78° C., followed by adding a solution of sodium azide in water and tetrahydrofuran or acetone, followed by adding toluene or benzene, and refluxing to produce isocyanate of formula (11):

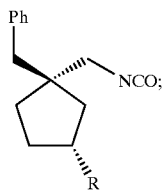

g) adding the product of Step f) to a mixture of a solvent and methanol, and stirring to produce the carbamate of formula (12):

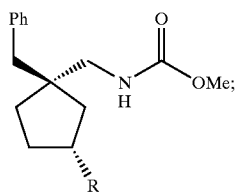

h) adding the product of Step g) to a mixture of carbon tetrachloride or ethyl acetate, and acetonitrile, water, sodium periodate, and ruthenium(III) chloride, and stirring to produce the carboxylic acid of formula (13):

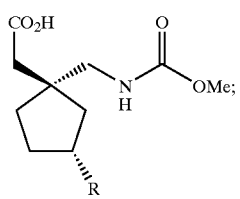

i) adding the product of Step h) to a mixture of a solvent and aqueous hydrochloric acid, and stirring to produce a compound of formula (IIa):

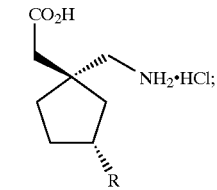

j) converting the product of Step i) to a compound of formula (II):

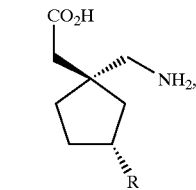

and further converting, if desired, to a pharmaceutically acceptable salt by known means.

This process is outlined below in Scheme 2.

Scheme 2

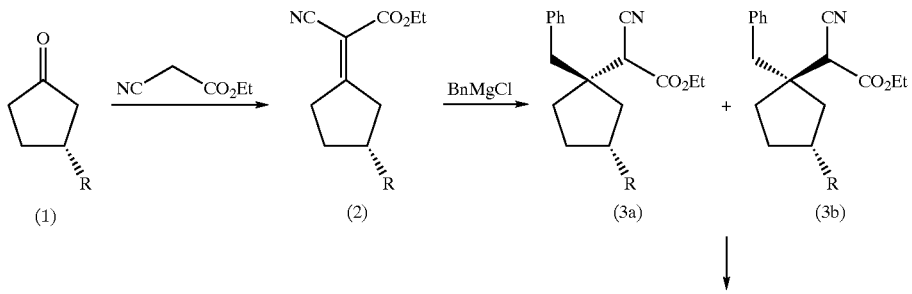

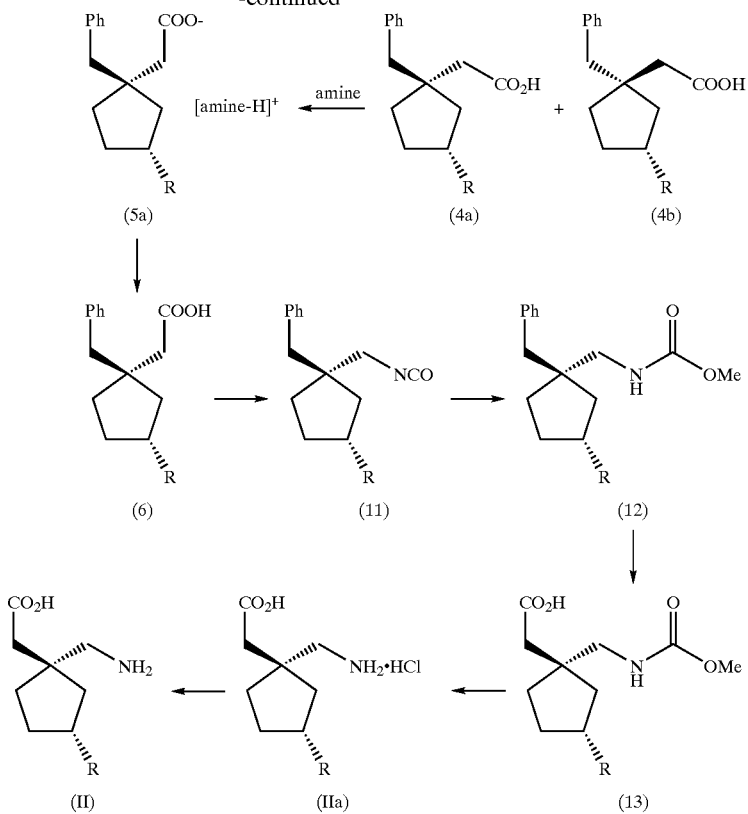

Preferred is a process for the preparation of a compound of Formula II wherein R is $C_1$–$C_{10}$ alkyl or $C_3$–$C_{10}$ cycloalkyl, and pharmaceutically acceptable salts thereof, which comprises:

a) adding a cyanoacetate of formula (A)

wherein $R_1$ is selected from methyl, ethyl, n-propyl, iso-propyl, n-butyl, iso-butyl, sec-butyl, tert-butyl, and benzyl to a mixture of a chiral cyclopentanone of formula (1):

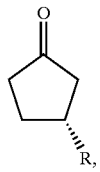

a solvent selected from tetrahydrofuran, 1,4-dioxane, tert-butylmethylether, chloroform, dichloromethane, acetonitrile, ethyl ether, ethyl acetate, hexanes, N,N-dimethylformamide, dimethylsulfoxide, ethanol, tert-butanol, toluene, benzene, xylenes, and n-heptane, acetic acid, and a Knoevenagel reaction catalyst selected from β-alanine, ammonium acetate, and piperidine, and stirring the mixture in the presence of a means of removing water selected from azeotropic distillation, activated molecular sieves, anhydrous magnesium sulfate, anhydrous sodium sulfate, anhydrous sodium carbonate, anhydrous potassium carbonate, anhydrous cesium carbonate, trimethyl orthoformate, and triethyl orthoformate to produce the alkene of formula (2):

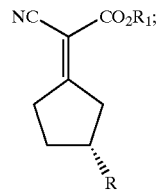

b) adding the product of Step a) above to a mixture of benzylmagnesium chloride, benzylmagnesium bromide, or benzylmagnesium iodide in a solvent selected from tetrahydrofuran, benzene, 1,4-dioxane, hexanes, n-heptane, toluene, diethyl ether, and tert-butyl methyl ether to produce the addition products of formulas (3a):

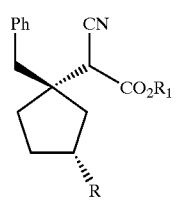

and (3b):

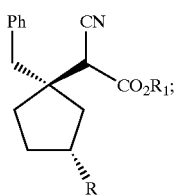

c) adding the products of Step b) above to a mixture of a base selected from potassium hydroxide, sodium hydroxide, lithium hydroxide, and cesium hydroxide in a solvent selected from ethylene glycol, 2-methoxyethyl ether, 1,4-dioxane, and diethylene glycol, and stirring the mixture and then acidifying to produce the carboxylic acids of formulas (4a):

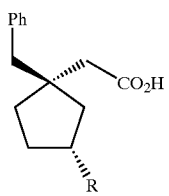

and (4b)

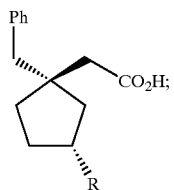

or adding the products of Step b) above to an acid mixture selected from 6–12 M HCl, 12 M $H_2SO_4$, 10%–48% wt/wt hydrobromic acid, and HBr in aqueous acetic acid, and stirring to produce the carboxylic acids of formulas (4a):

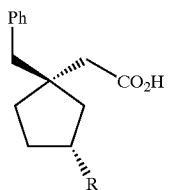

and (4b):

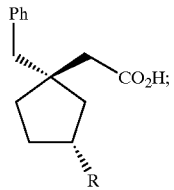

d) contacting the products of Step c) above with an amine selected from (S)-α-methyl-benzylamine, (R)-α-methyl-benzylamine, (R)-(+)-1-(naphthyl)ethylamine, (S)-(+)-1-(naphthyl)ethylamine, triethylamine, diisopropylethylamine, dicyclohexylamine, benzylamine, dibenzylamine, morpholine, N-methylmorpholine, piperidine, N-methylpiperidine, and pyridine in a solvent selected from N,N-dimethylformamide, chloroform, benzene, xylenes, hexanes, acetone, ethanol, methanol, iso-propanol, diethyl ether, dichloromethane, benzene, toluene, n-pentane, n-hexane, n-heptane, ethyl acetate, acetonitrile, tert-butyl methyl ether, tetrahydrofuran, and 1,4-dioxane, and recrystallizing the salt so formed to produce the enriched diastereomer of formula (5):

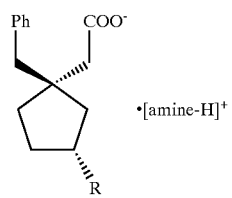

as the amine salt;

e) adding the product of Step d) to a mixture selected from aqueous hydrochloric acid, aqueous sulfuric acid, aqueous acetic acid, hydrochloric acid dissolved in acetic acid, and hydrochloric acid dissolved in acetic acid and water, and stirring to produce the carboxylic acid of formula (6):

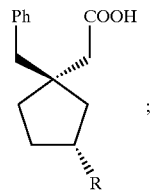

or partitioning the product of Step d) between a mixture of aqueous hydrochloric acid and a solvent selected from chloroform, dichloromethane, ethyl acetate, ethyl ether, tetrahydrofuran, 1,4-dioxane, toluene, and tert-butylmethylether, and drying and evaporating the organic layer to produce the carboxylic acid of formula (6):

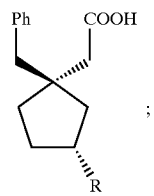

f) adding the product of Step e) above to a mixture of a base selected from triethylamine and diisopropylethylamine, a solvent selected from toluene, benzene, xylenes, tetrahydrofuran, diethyl ether and n-heptane, and diphenylphosphoryl azide (DPPA), and stirring at a temperature of from 0° C. to 150° C. to produce the isocyanate of formula (11):

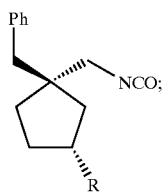

or adding the product of Step e) above to ethyl chloroformate or isobutyl chloroformate and a base selected from triethylamine and diisopropylethylamine, and a solvent selected from tetrahydrofuran, acetone, and diethyl ether at a temperature of from −40° C. to 78° C., followed by adding a solution of sodium azide in water and tetrahydrofuran or acetone, followed by adding toluene or benzene, and refluxing to produce the isocyanate of formula (11):

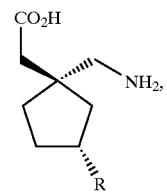

g) adding the product of Step f) to a solvent selected from toluene, benzene, xylenes, and n-heptane, and methanol, and stirring at a temperature from 0° C. to 150° C. to produce the carbamate of formula (12):

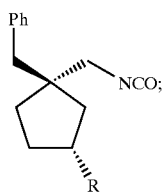

h) adding the product of Step g) to a mixture of carbon tetrachloride or ethyl acetate, and acetonitrile, water, sodium periodate, and ruthenium(III) chloride, and stirring at a temperature from −40° C. to 80° C. to produce the carboxylic acid of formula (13):

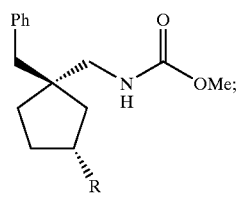

i) adding the product of Step h) to a mixture of a solvent selected from water, acetic acid, and 1,4-dioxane, and aqueous hydrochloric acid at a concentration of from 0.01 M to 12 M, and stirring at a temperature from 020 C. to 115° C. to produce a compound of formula IIa:

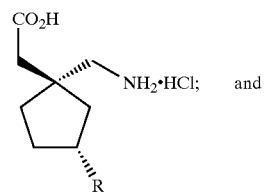

j) converting the product of Step i) to a compound of Formula II:

and further converting, if desired, to a pharmaceutically acceptable salt by known means.

More preferred is a process for the preparation of a compound of Formula II wherein R is $C_1$–$C_{10}$ alkyl or $C_3$–$C_{10}$ cycloalkyl, and pharmaceutically acceptable salts thereof, which comprises:

a) adding a cyanoacetate of formula (A)

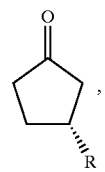

wherein $R_1$ is ethyl, to a mixture of a chiral cyclopentanone of formula (1):

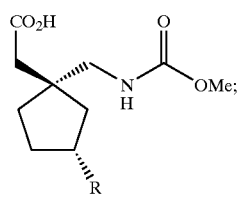

toluene, acetic acid, and a Knoevenagel reaction catalyst which is ammonium acetate, and heating the mixture at reflux over a Dean-Stark trap to produce the alkene of formula (2):

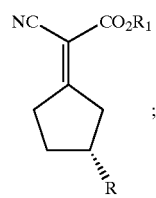

b) adding the product of Step a) above to a mixture of benzylmagnesium chloride in dry tetrahydrofuran at −100° C. to 25° C. to produce the addition products of formulas (3a):

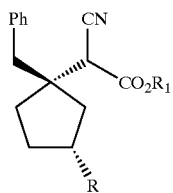

and (3b):

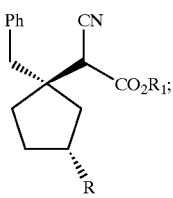

c) adding the products of Step b) above to a mixture of potassium hydroxide in ethylene glycol, and heating the mixture at 100° C. to 200° C., and then acidifying to produce the hydrolysis products of formulas (4a):

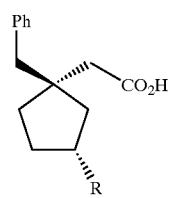

and (4b)

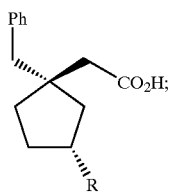

d) contacting the products of Step c) above with (S)-α-methyl-benzylamine in ethyl acetate, and recrystallizing the salt so formed from ethyl acetate to produce the enriched diastereomer of formula (5):

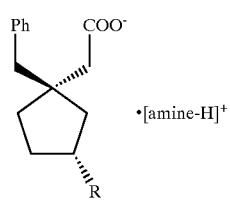

as the (S)-α-methyl-benzylamine salt;

e) adding the product of Step d) to aqueous hydrochloric acid and stirring to produce the carboxylic acid of formula (6):

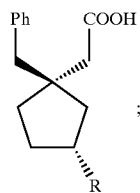

f) adding the product of Step e) to a mixture of triethylamine, toluene, and diphenylphosphoryl azide (DPPA), and refluxing to produce the isocyanate of formula (11):

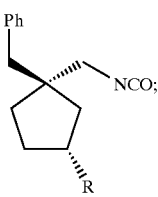

or adding the product of Step e) above to ethyl chloroformate or isobutyl chloroformate and triethylamine in tetrahydrofuran at a temperature of from −40° C. to 78° C., followed by adding a solution of sodium azide in water and tetrahydrofuran or acetone, followed by adding toluene or benzene, and refluxing to produce isocyanate of formula (11):

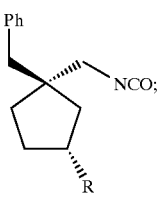

g) adding the product of Step f) to a mixture of methanol and toluene, and refluxing to produce the carbamate of formula (12):

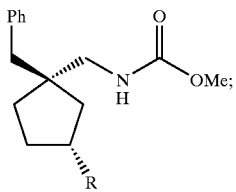

h) adding the product of Step g) to a mixture of carbon tetrachloride or ethyl acetate, and acetonitrile, water, sodium periodate, and ruthenium(III) chloride, and stirring to produce the carboxylic acid of formula (13):

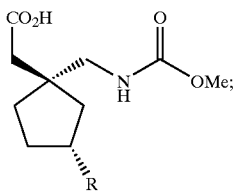

i) adding the product of Step h) to a mixture of 1,4-dioxane and aqueous hydrochloric acid at a concentration of 6 M, and stirring to produce a compound of formula IIa:

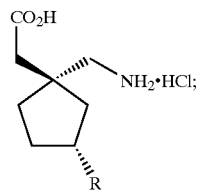

j) converting the product of Step i) to a compound of Formula II:

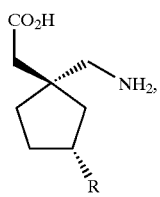

and further converting, if desired, to a pharmaceutically acceptable salt by known means.

Also preferred is a process for the preparation of a compound of Formula II as described above, further characterized in that the intermediate product (11):

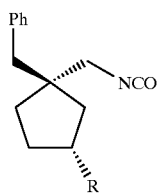

formed is further reacted, without isolation, with methanol to produce the carbamate of formula (12):

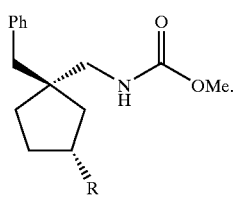

Still further, the invention provides a process for the preparation of a compound of Formula II:

II

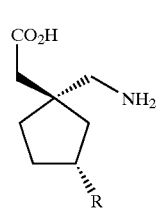

wherein R is $C_1$–$C_{10}$ alkyl or $C_3$–$C_{10}$ cycloalkyl, and pharmaceutically acceptable salts thereof, which comprises:

a) adding a cyanoacetate of formula (A)

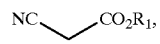

wherein $R_1$ is alkyl or benzyl, to a mixture of a chiral cyclopentanone of formula (1):

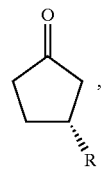

a solvent, a carboxylic acid, and a Knoevenagel reaction catalyst, and stirring the mixture in the presence of a means of removing water to produce the alkene of formula (2):

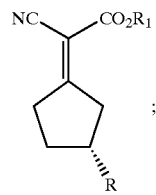

b) adding the product of Step a) above to a mixture of benzylmagnesium chloride, benzylmagnesium bromide, or benzylmagnesium iodide, in a solvent to produce the addition products of formulas (3a):

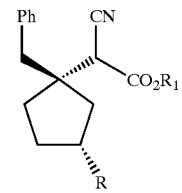

and (3b):

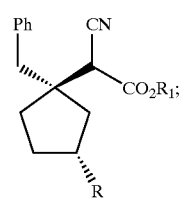

c) adding the products of Step b) above to a mixture of a base selected from potassium hydroxide, sodium hydroxide, lithium hydroxide, and cesium hydroxide, in a solvent, and stirring, and then acidifying to produce the carboxylic acids of formulas (4a):

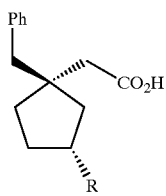

and (4b)

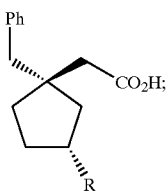

or adding the products of Step b) above to an acid mixture and stirring to produce the carboxylic acids of formulas (4a):

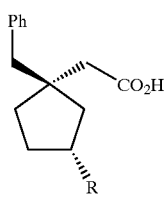

and (4b):

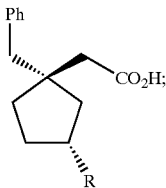

d) contacting the products of Step c) above with an amine in a solvent, and recrystallizing the salt so formed to produce the enriched diastereomer of formula (5):

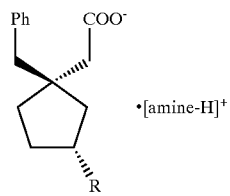

as the amine salt;

e) converting the product of Step d) to a carboxylic acid of formula (6):

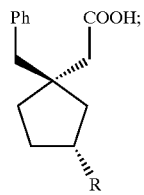

f) adding oxalyl chloride to a mixture of the product of Step e), a solvent, and N,N-dimethylformamide (DMF), and stirring to produce the acid chloride of formula (14):

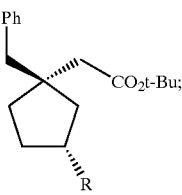

g) adding the product of Step f) to a mixture of tert-butyl alcohol, a solvent, and a tertiary amine base, and stirring to produce the ester of formula (15):

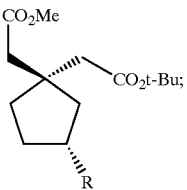

h) adding the product of Step g) to a mixture of carbon tetrachloride or ethyl acetate, and acetonitrile, water, sodium periodate, and ruthenium(III) chloride, and stirring to produce the carboxylic acid of formula (16):

i) adding the product of Step h) to a mixture of a solvent, methanol, and (trimethylsilyl)diazomethane, and stirring to produce the bis ester of formula (17):

or adding the product of Step h) to a mixture of iodomethane, a solvent, and a base, and stirring to produce the bis ester of formula (17):

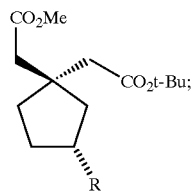

j) adding an acid to a mixture of the product from Step i) and a solvent, and stirring to produce the carboxylic acid of formula (18):

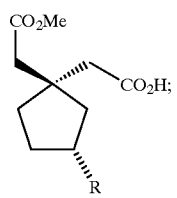

k) adding the product of Step j) to a mixture of a tertiary amine base, a solvent, and diphenylphosphoryl azide (DPPA) is added, and stirring to produce the isocyanate of formula (19):

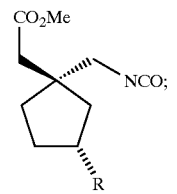

or adding the product of Step j) above to ethyl chloroformate or isobutyl chloroformate and a base in a solvent at a temperature of from −40° C. to 78° C., followed by adding a solution of sodium azide in water and tetrahydrofuran or acetone, followed by adding toluene or benzene, and refluxing to produce isocyanate of formula (19):

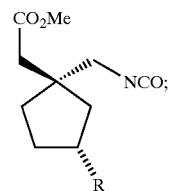

l) adding the product of Step k) to a mixture of a solvent and methanol, and stirring to produce the carbamate of formula (20):

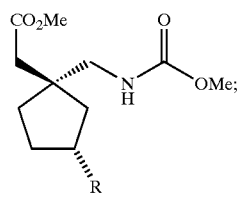

m) adding the product of Step l) to a mixture of a solvent and aqueous hydrochloric acid is added, and stirring to produce a compound of formula (IIa):

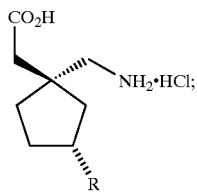

and n) converting the product of Step m) to a compound of formula (II):

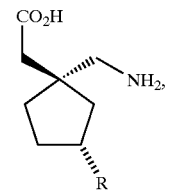

and further converting, if desired, to a pharmaceutically acceptable salt by known means.

This process is outlined in Scheme 3.

Scheme 3

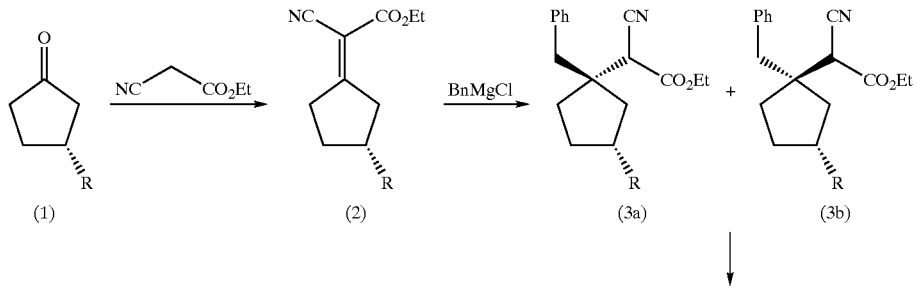

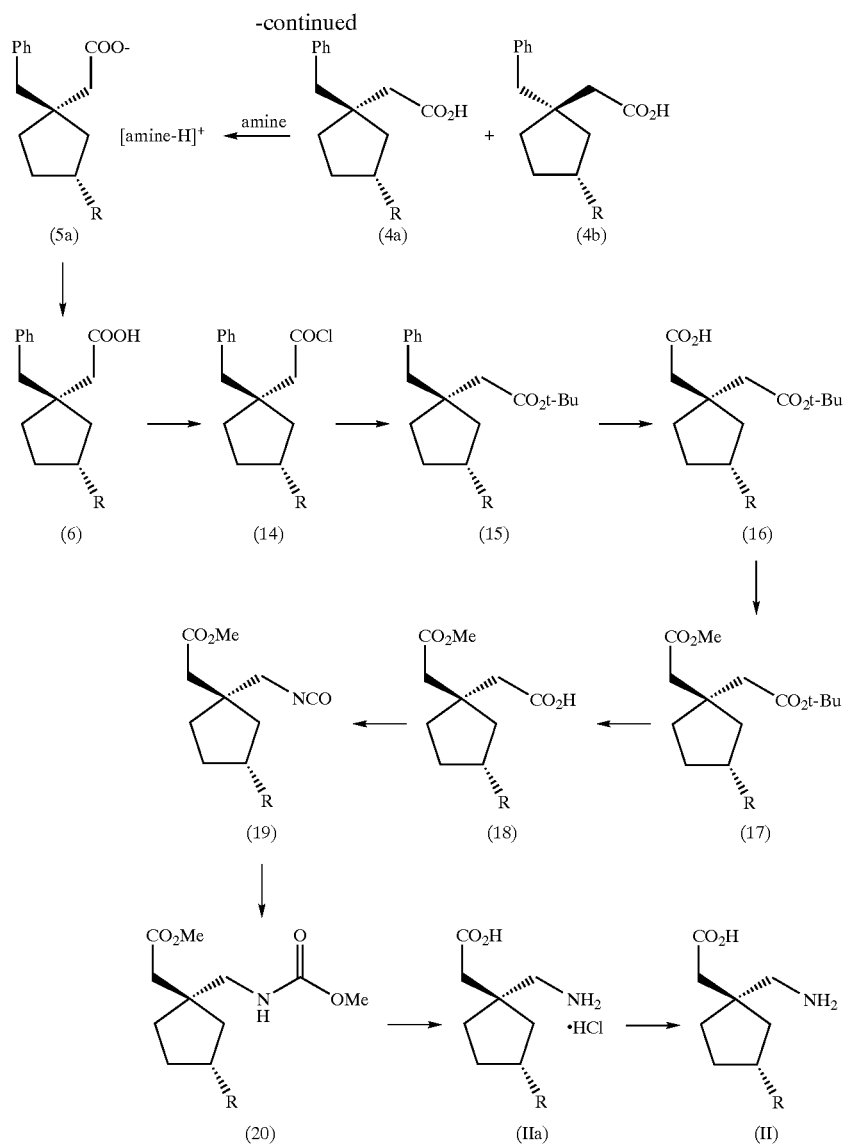

Preferred is a process for the preparation of a compound of Formula II wherein R is $C_1$–$C_{10}$ alkyl or $C_3$–$C_{10}$ cycloalkyl, and pharmaceutically acceptable salts thereof, which comprises:

a) adding a cyanoacetate of formula (A)

wherein $R_1$ is selected from methyl, ethyl, n-propyl, iso-propyl, n-butyl, iso-butyl, sec-butyl, tert-butyl, and benzyl to a mixture of a chiral cyclopentanone of formula (1):

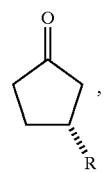

a solvent selected from tetrahydrofuran, 1,4-dioxane, tert-butylmethylether, chloroform, dichloromethane, acetonitrile, ethyl ether, ethyl acetate, hexanes, N,N-dimethylformamide, dimethylsulfoxide, ethanol, tert-butanol, toluene, benzene, xylenes, and n-heptane, acetic acid, and a Knoevenagel reaction catalyst selected from β-alanine, ammonium acetate, and piperidine, and stirring the mixture in the presence of a means of removing water selected from azeotropic distillation, activated molecular sieves, anhydrous magnesium sulfate, anhydrous sodium sulfate, anhydrous sodium carbonate, anhydrous potassium carbonate, anhydrous cesium carbonate, trimethyl-orthoformate, and triethyl orthoformate to produce the alkene of formula (2):

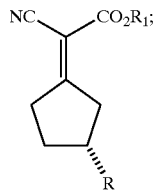

b) adding the product of Step a) above to a mixture of benzylmagnesium chloride, benzylmagnesium bromide, or benzylmagnesium iodide in a solvent selected from tetrahydrofuran, benzene, 1,4-dioxane, hexanes, n-heptane, toluene, diethyl ether, and tert-butyl methyl ether to produce the addition products of formulas (3a):

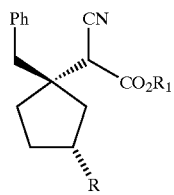

and (3b):

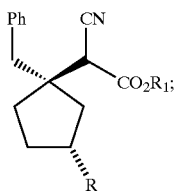

c) adding the products of Step b) above to a mixture of a base selected from potassium hydroxide, sodium hydroxide, lithium hydroxide, and cesium hydroxide in a solvent selected from ethylene glycol, 2-methoxyethyl ether, 1,4-dioxane, and diethylene glycol, and stirring the mixture and then acidifying to produce the carboxylic acids of formulas (4a):

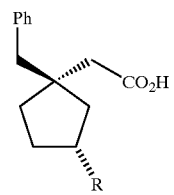

and (4b)

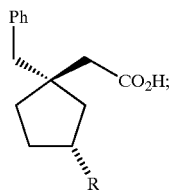

or adding the products of Step b) above to an acid mixture selected from 6–12 M HCl, 12 M $H_2SO_4$, 10%–48% wt/wt hydrobromic acid, and HBr in aqueous acetic acid, and stirring to produce the carboxylic acids of formulas (4a):

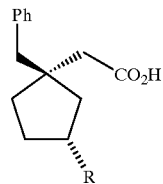

and (4b):

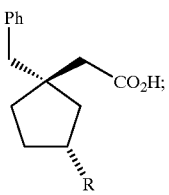

d) contacting the products of Step c) above with an amine selected from (S)-α-methyl-benzylamine, (R)-α-methyl-benzylamine, (R)-(+)-1-(naphthyl)ethylamine, (S)-(+)-1-(naphthyl)ethylamine, triethylamine, diisopropylethylamine, dicyclohexylamine, benzylamine, dibenzylamine, morpholine, N-methylmorpholine, piperidine, N-methylpiperidine, and pyridine in a solvent selected from N,N-dimethylformamide, chloroform, benzene, xylenes, hexanes, acetone, ethanol, methanol, iso-propanol, diethyl ether, dichloromethane, benzene, toluene, n-pentane, n-hexane, n-heptane, ethyl acetate, acetonitrile, tert-butyl methyl ether, tetrahydrofuran, and 1,4-dioxane, and recrystallizing the salt so formed to produce the enriched diastereomer of formula (5):

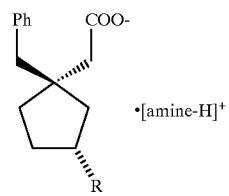

as the amine salt;

e) adding the product of Step d) to a mixture selected from aqueous hydrochloric acid, aqueous sulfuric acid, aqueous acetic acid, hydrochloric acid dissolved in acetic acid, or hydrochloric acid dissolved in acetic acid and water, and stirring to produce the carboxylic acid of formula (6):

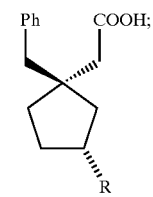

or partitioning the product of Step d) between a mixture of aqueous hydrochloric acid and a solvent selected from chloroform, dichloromethane, ethyl acetate, ethyl ether, tetrahydrofuran, 1,4-dioxane, toluene, and tert-butylmethylether, and drying and evaporating the organic layer to produce the carboxylic acid of formula (6):

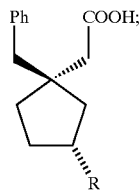

f) adding oxalyl chloride to a mixture of the product of Step e), a solvent selected from dichloromethane, chloroform, ethyl ether, toluene, and tert-butyl methyl ether, and 0.01 to 10 mole percent of N,N-dimethylformamide (DMF), and stirring at a temperature from −40° C. to 110° C. to produce the acid chloride of formula (14):

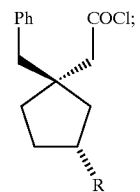

g) adding the product of Step f) to a mixture of tert-butyl alcohol, a solvent selected from dichloromethane, chloroform, ethyl ether, toluene, and tert-butyl methyl ether, and N,N-diisopropylethylamine (DIPEA) or triethylamine, and stirring at a temperature from −40° C. to 110° C. to produce the ester of formula (15):

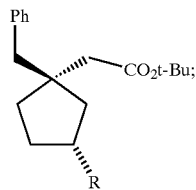

h) adding the product of Step g) to a mixture of carbon tetrachloride or ethyl acetate, and acetonitrile, water, sodium periodate, and ruthenium(III) chloride, and stirring at a temperature from −40° C. to 80° C. to produce the carboxylic acid of formula (16):

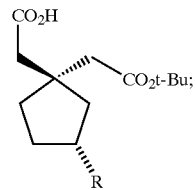

i) adding the product of Step h) to a solvent selected from toluene, benzene, xylenes, and n-heptane, methanol, and (trimethylsilyl)diazomethane, and stirring at a temperature from 0° C. to 150° C. to produce the bis ester of formula (17):

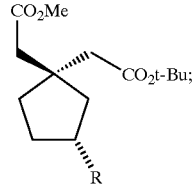

or adding the product of Step h) to a mixture of iodomethane, a solvent selected from dichloromethane, chloroform, tetrahydrofuran, toluene and 1,4-dioxane, and a base selected from 1,8-diazabicyclo[5.4.0]undec-7-ene (DBU), diisopropylethylamine, triethylamine, or 1,5-diazabicyclo[4.3.0]non-5-ene (DBN), and stirring at a temperature of from −40° C. to 110° C. to produce the bis ester of formula (17):

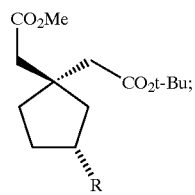

j) adding hydrochloric acid or trifluoroacetic acid (TFA) to a mixture of the product from Step i) and a solvent selected from dichloromethane, chloroform, 1,4-dioxane, tetrahydrofuran, ethyl ether, and tert-butyl methyl ether, and stirring at a temperature from −40° C. to 110° C. to produce the carboxylic acid of formula (18):

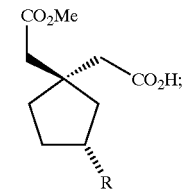

k) adding the product of Step j) to a mixture of a base selected from triethylamine and diisopropylethylamine, a solvent selected from toluene, benzene, xylenes, and n-heptane, and diphenylphosphoryl azide (DPPA), and stirring at a temperature from 0° C. to 150° C. to produce the isocyanate of formula (19):

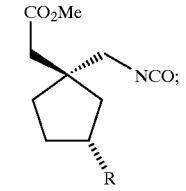

or adding the product of Step j) above to ethyl chloroformate or isobutyl chloroformate, a base selected from triethylamine and diisopropylethylamine, and a solvent selected from tetrahydrofuran, acetone, and diethyl ether at a temperature of from −40° C. to 78° C., followed by adding a solution of sodium azide in water and tetrahydrofuran or acetone, followed by adding toluene or benzene, and refluxing to produce isocyanate of formula (19):

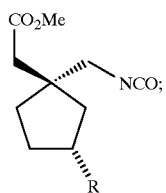

l) adding the product of Step k) to a mixture of a solvent selected from toluene, benzene, xylenes, and n-heptane, and methanol, and stirring at a temperature from 0° C. to 150° C. to produce the carbamate of formula (20):

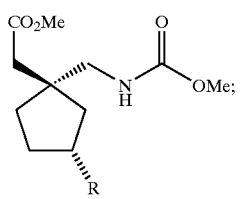

m) adding the product of Step l) to a mixture of a solvent selected from water, acetic acid, and 1,4-dioxane, and aqueous hydrochloric acid at a concentration of from 0.01 M to 12 M, and stirring at a temperature from 0° C. to 115° C. to produce a compound of formula IIa:

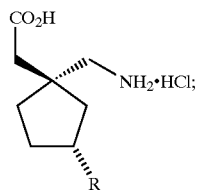

and n) converting the product of Step m) to a compound of Formula II:

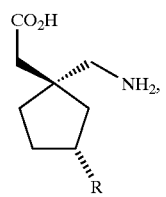

and further converting, if desired, to a pharmaceutically acceptable salt by known means.

More preferred is a process for the preparation of a compound of Formula II wherein R is $C_1$–$C_{10}$ alkyl or $C_3$–$C_{10}$ cycloalkyl, and pharmaceutically acceptable salts thereof, which comprises:

a) adding a cyanoacetate of formula (A):

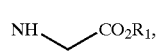

wherein $R_1$ is ethyl, to a mixture of a chiral cyclopentanone of formula (1):

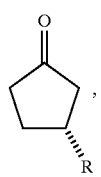

toluene, acetic acid, and a Knoevenagel reaction catalyst which is ammonium acetate, and heating the mixture at reflux over a Dean-Stark trap to produce the alkene of formula (2):

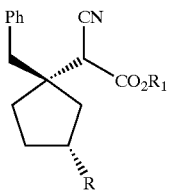

b) adding the product of Step a) above to a mixture of benzylmagnesium chloride in dry tetrahydrofuran at −100° C. to 25° C. to produce the addition products of formulas (3a):

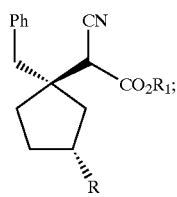

and (3b):

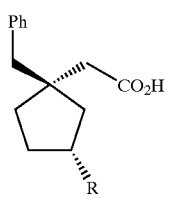

c) adding the products of Step b) above to a mixture of potassium hydroxide in ethylene glycol and heating the mixture at 100° C. to 200° C., and then acidifying to produce the hydrolysis products of formulas (4a):

and (4b):

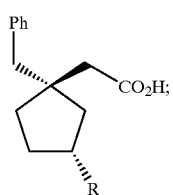

d) contacting the products of Step c) above with (S)-α-methyl-benzylamine in ethyl acetate, and recrystallizing the salt so formed from ethyl acetate to produce the enriched diastereomer of formula (5):

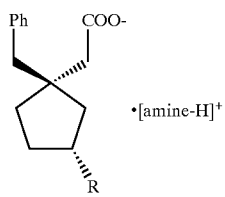

as the (S)-α-methyl-benzylamine salt;

e) adding the product of Step d) to aqueous hydrochloric acid and stirring to produce the carboxylic acid of formula (6):

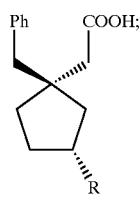

f) adding oxalyl chloride to a mixture of the product of Step e), dichloromethane, and a catalytic amount of N,N-dimethylformamide (DMF), and stirring to produce the acid chloride of formula (14):

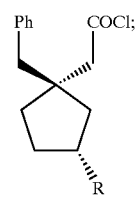

g) adding the product of Step f) to a mixture of tert-butyl alcohol, dichloromethane, and N,N-diisopropylethylamine (DIPEA), and stirring to produce the ester of formula (15):

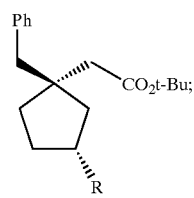

h) adding the product of Step g) to a mixture of carbon tetrachloride or ethyl acetate, and acetonitrile, water, sodium periodate, and ruthenium(III) chloride, and stirring to produce the carboxylic acid of formula (16):

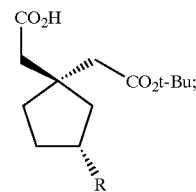

i) adding the product of Step h) to a mixture of methanol, toluene, and (trimethylsilyl)diazomethane, and stirring to produce the bis ester of formula (17):

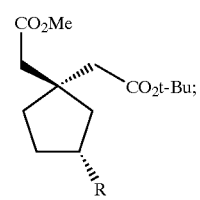

or adding the product of Step h) to a mixture of iodomethane, dichloromethane, triethylamine, and stirring to produce the bis ester of formula (17):

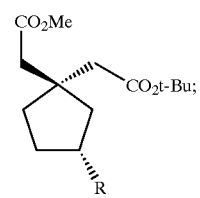

j) adding hydrochloric acid or trifluoroacetic acid (TFA) to a mixture of the product from Step i) and dichloromethane, and stirring to produce the carboxylic acid of formula (18):

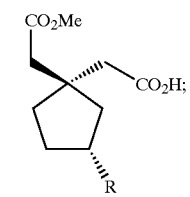

k) adding the product of Step j) to a mixture of triethylamine, toluene, and diphenylphosphoryl azide (DPPA), and refluxing to produce the isocyanate of formula (19):

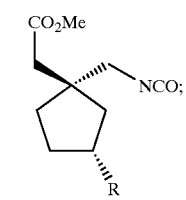

or adding the product of Step j) above to ethyl chloroformate or isobutyl chloroformate, triethylamine, and tetrahydrofuran at a temperature of from −40° C. to 78° C., followed by adding a solution of sodium azide in water and tetrahydrofuran or acetone, followed by adding toluene or benzene, and refluxing to produce isocyanate of formula (19):

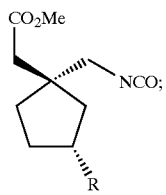

l) adding the product of Step k) to a mixture of methanol and toluene, and refluxing to produce the carbamate of formula (20):

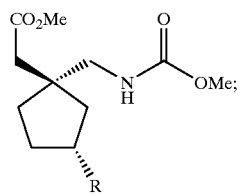

m) adding the product of Step l) to a mixture of 1,4-dioxane and aqueous hydrochloric acid at a concentration of 6 M, and stirring to produce a compound of formula IIa:

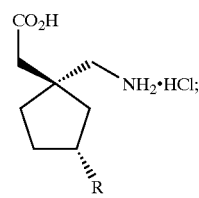

n) converting the product of Step m) to a compound of Formula II:

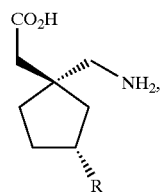

and further converting, if desired, to a pharmaceutically acceptable salt by known means.

Also preferred is a process for the preparation of a compound of Formula II, further characterized in that the intermediate product (14):

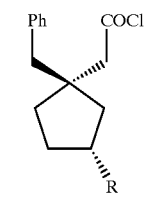

formed is further reacted, without isolation, with tert-butyl alcohol to produce the ester of formula (15):

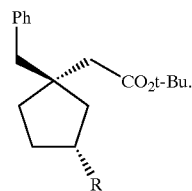

Also preferred is a process for the preparation of a compound of Formula II, further characterized in that the intermediate product (19):

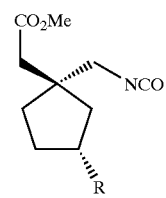

formed is further reacted, without isolation, with methanol to produce the carbamate of formula (20):

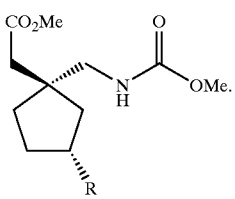

Also preferred is a process for the preparation of a compound of Formula II, further characterized in that the intermediate product (14):

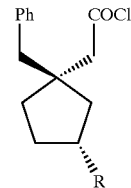

formed is further reacted, without isolation, with tert-butyl alcohol to produce the ester of Formula (15):

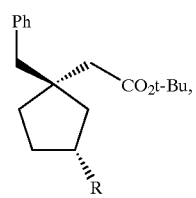

and the intermediate product (19):

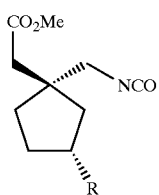

formed is further reacted, without isolation, with methanol to produce the carbamate of formula (20):

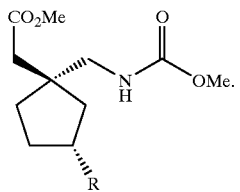

Further, the invention provides a process for the preparation of a compound of Formula III:

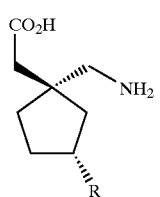                                                III wherein R is $C_1$–$C_{10}$ alkyl or $C_3$–$C_{10}$ cycloalkyl, and pharmaceutically acceptable salts thereof, which comprises:

a) adding a cyanoacetate of formula (A):

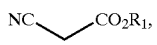

wherein $R_1$ is alkyl or benzyl, to a mixture of a chiral cyclopentanone of formula (21):

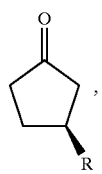

a solvent, a carboxylic acid, and a Knoevenagel reaction catalyst, and stirring the mixture in the presence of a means of removing water to produce the alkene of formula (22):

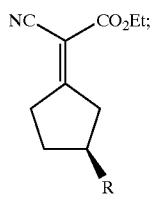

b) adding the product of Step a) above to a mixture of benzylmagnesium chloride or benzylmagnesium iodide, in a solvent to produce the addition of products of formulas (23a):

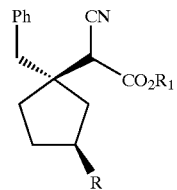

and (23b):

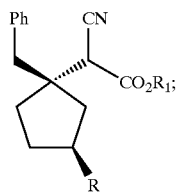

c) adding the products of Step b) above to a mixture of a base selected from potassium hydroxide, sodium hydroxide, lithium hydroxide, and cesium hydroxide, in a solvent, and stirring, and then acidifying to produce the carboxylic acids of formulas (24a):

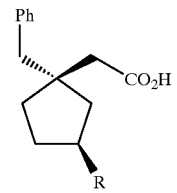

and (24b):

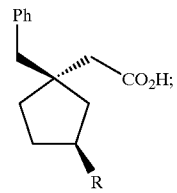

or adding the products of Step b) above to an acid mixture, and stirring to produce the carboxylic acids of formulas (24a):

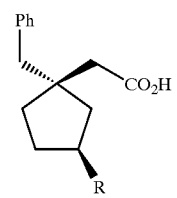

and (24b):

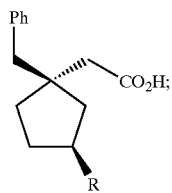

d) contacting the products of Step c) above with an amine in a solvent, and recrystallizing the salt so formed to produce the enriched diastereomer of formula (25):

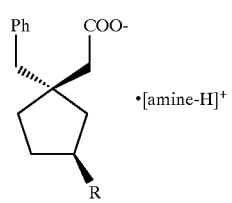

as the amine salt; and e) converting the product of Step d) to a carboxylic acid of formula (26):

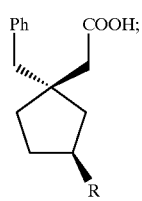

f) adding the product of Step e) to a mixture of iodomethane, a solvent, and 1,8-diazabicyclo[5.4.0]undec-7-ene (DBU), and stirring to produce the ester of formula (27):

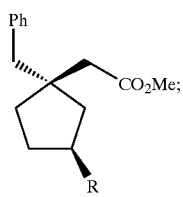

or adding the product of Step e) to methanol and an acid to produce the ester of formula (27):

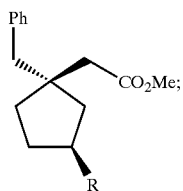

or adding the product of Step e) to a solution of diazomethane or trimethylsilyl-diazomethane in a solvent to produce ester of formula (27):

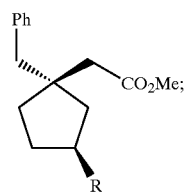

g) adding the product of Step f) to a mixture of carbon tetrachloride or ethyl acetate, and acetonitrile, water, sodium periodate, and ruthenium(III) chloride, and stirring to produce the carboxylic acid of formula (28):

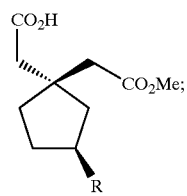

h) adding the product of Step g) to a mixture of a tertiary amine base, a solvent, and diphenylphosphoryl azide (DPPA), and stirring to produce the isocyanate of formula (29):

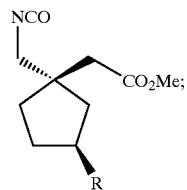

or adding the product of Step g) above to ethyl chloroformate or isobutyl chloroformate and a base in a solvent at a temperature of from −40° C. to 78° C., followed by adding a solution of sodium azide in water and tetrahydrofuran or acetone, followed by adding toluene or benzene, and refluxing to produce isocyanate of formula (29):

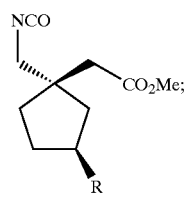

i) adding the product of Step h) to a mixture of a solvent and methanol, and stirring to produce the carbamate of formula (30):

j) adding the product of Step i) to a mixture of a solvent and aqueous hydrochloric acid, and stirring to produce a compound of formula (IIIa):
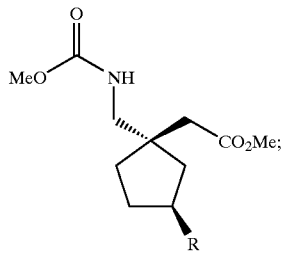
k) converting the product of Step j) to a compound of formula (III):
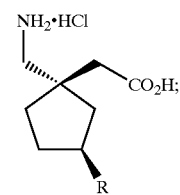
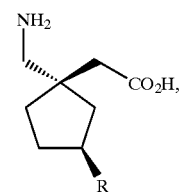
and further converting, if desired, to a pharmaceutically acceptable salt by known means.
This process is outlined in Scheme 4.
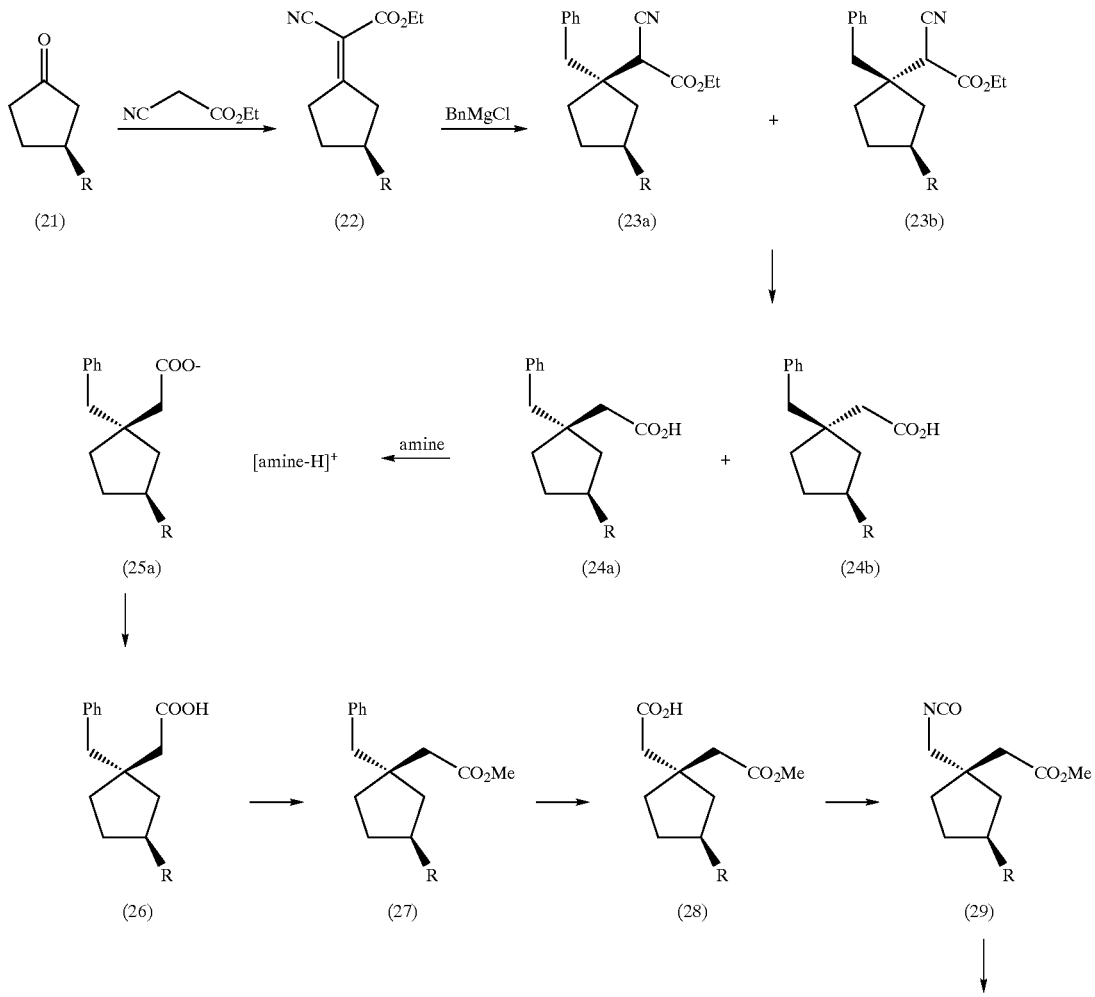
Scheme 4

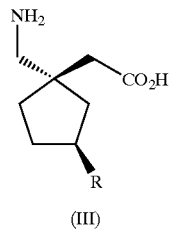 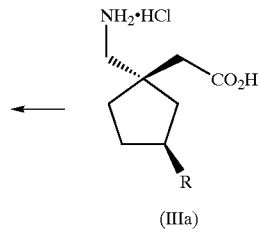 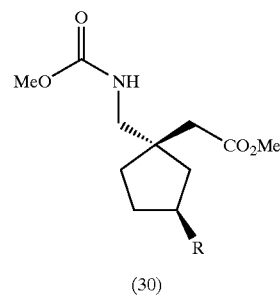

(III)    (IIIa)    (30)

Preferred is a process for the preparation of a compound of Formula III wherein R is $C_1$–$C_{10}$ alkyl or $C_3$–$C_{10}$ cycloalkyl, and pharmaceutically acceptable salts thereof, which comprises:

a) adding ethyl cyanoacetate to a mixture of a chiral cyclopentanone of formula (21) in a solvent selected from toluene, benzene, xylenes, or n-heptane to which acetic acid and β-alanine or ammonium acetate were added, and stirring the mixture at a temperature from 0° C. to 150° C. to produce the alkene of formula (22);

b) adding the product of Step a) above to a mixture of benzylmagnesium chloride in a dry solvent selected from tetrahydrofuran, 1,4-dioxane, n-heptane, toluene, ethyl ether, or tert-butyl methyl ether at a temperature from −100° C. to 110° C. to produce the addition products of formulas (23a) and (23b);

c) adding the products of Step b) above to a mixture of a base selected from potassium hydroxide, sodium hydroxide, lithium hydroxide, or cesium hydroxide in a solvent selected from ethylene glycol, 2-methoxyethyl ether, 1,4-dioxane, or diethylene glycol and stirring the mixture at a temperature from 25° C. to 250° C. to produce the carboxylic acids of formulas (24a) and (24b);

d) contacting the products of Step c) above with (R)-α-methyl-benzylamine in a solvent selected from ethyl acetate, acetonitrile, tetrahydrofuran, or 1,4-dioxane at a temperature from −40° C. to 105° C., and recrystallizing the salt so formed from a solvent selected from ethyl acetate, acetonitrile, tetrahydrofuran, 1,4-dioxane, tert-butyl methyl ether, toluene, or n-heptane to produce the enriched diastereomer of formula (25a) as the (R)-α-methyl-benzylamine salt;

e) adding the product of Step d) to a mixture selected from aqueous hydrochloric acid, hydrochloric acid dissolved in acetic acid, or hydrochloric acid dissolved in acetic acid to which water was added and stirring at a temperature from −40° C. to 115° C. to produce the carboxylic acid of formula (26);

f) adding the product of Step e) to a mixture of iodomethane in a solvent selected from dichloromethane, chloroform, tetrahydrofuran, toluene, or 1,4-dioxane to which 1,8-diazabicyclo[5.4.0]undec-7-ene (DBU) was added, and stirring at a temperature from −40° C. to 110° C. to produce the ester of formula (27);

g) adding the product of Step f) to a mixture of carbon tetrachloride and acetonitrile to which water, sodium periodate, and ruthenium(III) chloride were added, and stirring at a temperature from −40° C. to 80° C. to produce the carboxylic acid of formula (28);

h) adding the product of Step g) to a mixture of a base selected from triethylamine or diisopropylethylamine and a solvent selected from toluene, benzene, xylenes, or n-heptane to which diphenylphosphoryl azide (DPPA) was added, and stirring at a temperature from 0° C. to 150° C. to produce the isocyanate of formula (29);

i) adding the product of Step h) to a solvent selected from toluene, benzene, xylenes, or n-heptane to which methanol was added and stirring at a temperature from 0° C. to 150° C. to produce the carbamate of formula (30);

j) adding the product of Step i) to a solvent selected from water, acetic acid, or 1,4-dioxane to which aqueous hydrochloric acid at a concentration of from 0.01 M to 12 M was added, and stirring at a temperature from 0° C. to 115° C. to produce a compound of Formula IIIa;

k) converting the product of Step j) to a compound of Formula III, and further converting, if desired, to a pharmaceutically acceptable salt by known means.

More preferred is a process for the preparation of a compound of Formula III wherein R is $C_1$–$C_{10}$ alkyl or $C_3$–$C_{10}$ cycloalkyl, and pharmaceutically acceptable salts thereof, which comprises:

a) adding ethyl cyanoacetate to a mixture of a chiral cyclopentanone of formula (21) in toluene to which acetic acid and ammonium acetate were added, and heating the mixture at reflux to produce the alkene of formula (22);

b) adding the product of Step a) above to a mixture of benzylmagnesium chloride in dry tetrahydrofuran at −100° C. to −20° C. to produce the addition products of formulas (23a) and (23b);

c) adding the products of Step b) above to a mixture of potassium hydroxide in ethylene glycol, and heating the mixture at 100° C. to 200° C. to produce the hydrolysis products of formulas (24a) and (24b);

d) contacting the products of Step c) above with (R)-α-methyl-benzylamine in ethyl acetate, and recrystallizing the salt so formed from ethyl acetate to produce the enriched diastereomer of formula (25a) as the (R)-α-methyl-benzylamine salt;

e) adding the product of Step d) to aqueous hydrochloric acid and stirring to produce the carboxylic acid of formula (26);

f) adding the product of Step e) to a mixture of iodomethane in dichloromethane to which 1,8-diazabicyclo[5.4.0]undec-7-ene (DBU) was added, and stirring to produce the ester of formula (27);

g) adding the product of Step f) to a mixture of carbon tetrachloride and acetonitrile to which water, sodium periodate, and ruthenium(III) chloride were added, and stirring to produce the carboxylic acid of formula (28);

h) adding the product of Step g) to a mixture of triethylamine and toluene to which diphenylphosphoryl azide (DPPA) was added, and refluxing to produce the isocyanate of formula (29);

i) adding the product of Step h) to a mixture of methanol and toluene, and refluxing to produce the carbamate of formula (30);

j) adding the product of Step i) to 1,4-dioxane to which aqueous hydrochloric acid at a concentration of 6 M was added, and stirring to produce a compound of Formula IIIa;

k) converting the product of Step j) to a compound of Formula III, and further converting, if desired, to a pharmaceutically acceptable salt by known means.

Also preferred is a process for the preparation of a compound of Formula III, further characterized in that the intermediate product (29):

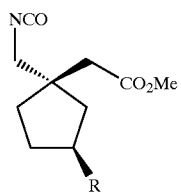

formed is further reacted, without isolation, with methanol to produce the carbamate of formula (30):

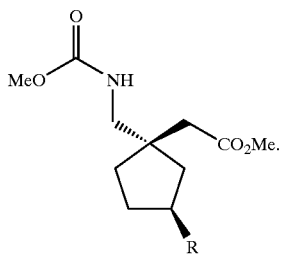

Further, the invention provides a process for the preparation of a compound of Formula IV:

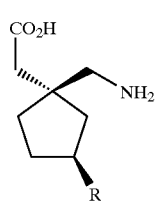

wherein R is $C_1$–$C_{10}$ alkyl or $C_3$–$C_{10}$ cycloalkyl, and pharmaceutically acceptable salts thereof, which comprises:

a) adding a cyanoacetate of formula (A):

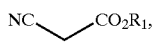

wherein $R_1$ is alkyl or benzyl, to a mixture of a chiral cyclopentanone of formula (21):

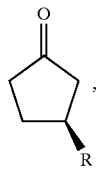

a solvent, a carboxylic acid, and a Knoevenagel reaction catalyst, and stirring the mixture in the presence of a means of removing water to produce the alkene of formula (22):

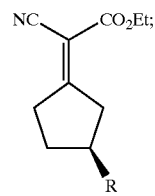

b) adding the product of Step a) above to a mixture of benzylmagnesium chloride or benzylmagnesium iodide, in a solvent to produce the addition of products of formulas (23a):

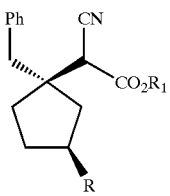

and (23b):

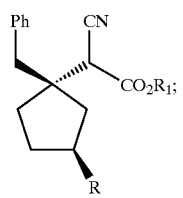

c) adding the products of Step b) above to a mixture of a base selected from potassium hydroxide, sodium hydroxide, lithium hydroxide, and cesium hydroxide, in a solvent, and stirring, and then acidifying to produce the carboxylic acids of formulas (24a):

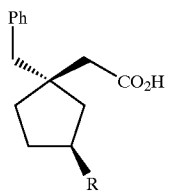

and (24b):

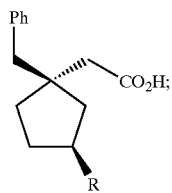

or adding the products of Step b) above to an acid mixture, and stirring to produce the carboxylic acids of formulas (24a):

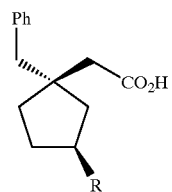

and (24b):

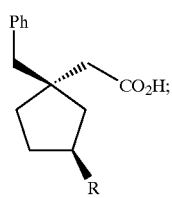

d) contacting the products of Step c) above with an amine in a solvent, and recrystallizing the salt so formed to produce the enriched diastereomer of formula (25):

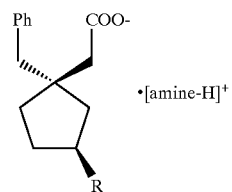

as the amine salt; and e) converting the product of Step d) to a carboxylic acid of formula (26):

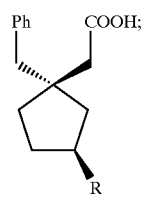

f) adding the product of Step e) to a mixture of a tertiary amine base, a solvent, and diphenylphosphoryl azide (DPPA) is added, and stirring to produce the isocyanate of formula (31):

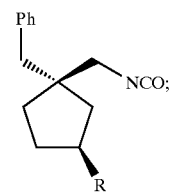

or adding the product of Step g) above to ethyl chloroformate or isobutyl chloroformate and a base in a solvent at a temperature of from −40° C. to 78° C., followed by adding a solution of sodium azide in water and tetrahydrofuran or acetone, followed by adding toluene or benzene, and refluxing to produce the isocyanate of formula (31):

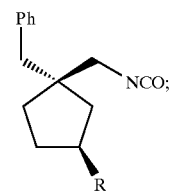

g) adding the product of Step f) to a mixture of a solvent and methanol, and stirring to produce the carbamate of formula (32):

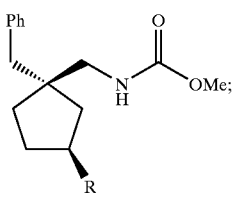

h) adding the product of Step g) to a mixture of carbon tetrachloride or ethyl acetate, and acetonitrile, water, sodium periodate, and ruthenium(III) chloride, and stirring to produce the carboxylic acid of formula (33):

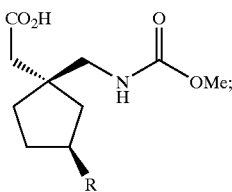

i) adding the product of Step h) to a mixture of a solvent and aqueous hydrochloric acid, and stirring to produce a compound of formula (IVa):

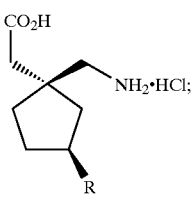

and j) converting the product of Step i) to a compound of formula (IV):

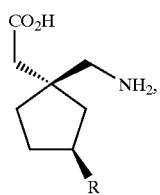

and further converting, if desired, to a pharmaceutically acceptable salt by known means.

This process is outlined in Scheme 5.

added, and stirring the mixture at a temperature from 0° C. to 150° C. to produce the alkene of formula (22);

b) adding the product of Step a) above to a mixture of benzylmagnesium chloride in a dry solvent selected from tetrahydrofuran, 1,4-dioxane, n-heptane, toluene, ethyl ether, or tert-butyl methyl ether at a temperature from −100° C. to 110° C. to produce the addition products of formulas (23a) and (23b);

c) adding the products of Step b) above to a mixture of a base selected from potassium hydroxide, sodium hydroxide, lithium hydroxide, or cesium hydroxide in a solvent selected from ethylene glycol, 2-methoxyethyl ether, 1,4-dioxane, or diethylene glycol and stirring the

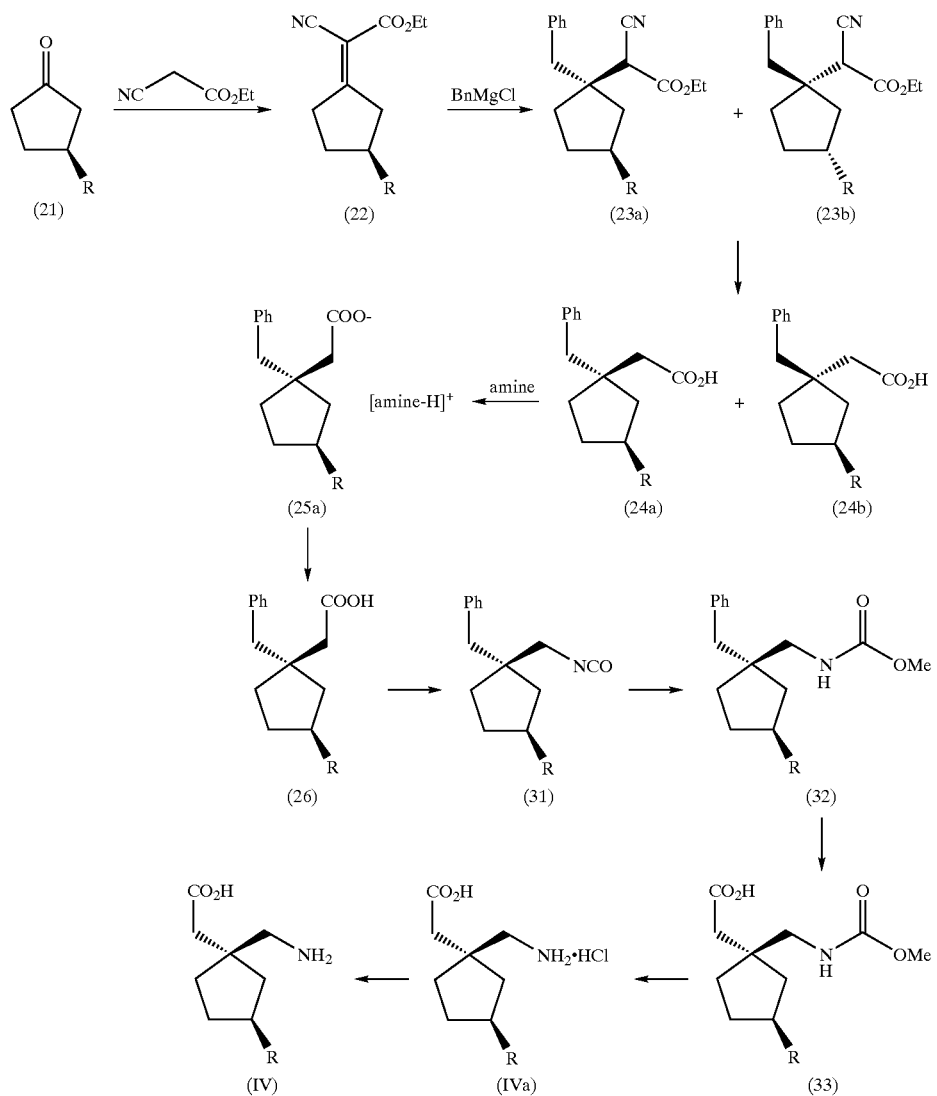

Preferred is a process for the preparation of a compound of Formula IV wherein R is $C_1$–$C_{10}$ alkyl or $C_3$–$C_{10}$ cycloalkyl, and pharmaceutically acceptable salts thereof, which comprises:

a) adding ethyl cyanoacetate to a mixture of a chiral cyclopentanone of formula (21) in a solvent selected from toluene, benzene, xylenes, or n-heptane to which acetic acid and β-alanine or ammonium acetate were mixture at a temperature from 25° C. to 250° C. to produce the carboxylic acids of formulas (24a) and (24b);

d) contacting the products of Step c) above with (R)-α-methyl-benzylamine in a solvent selected from ethyl acetate, acetonitrile, tetrahydrofuran, or 1,4-dioxane at a temperature from −40° C. to 105° C., and recrystallizing the salt so formed from a solvent selected from ethyl acetate, acetonitrile, tetrahydrofuran, 1,4-dioxane, tert-butyl methyl ether, toluene, or n-heptane to produce the enriched diastereomer of formula (25a) as the (R)-α-methyl-benzylamine salt;

e) adding the product of Step d) to a mixture selected from aqueous hydrochloric acid, hydrochloric acid dissolved in acetic acid, or hydrochloric acid dissolved in acetic acid to which water was added and stirring at a temperature from −40° C. to 115° C. to produce the carboxylic acid of formula (26);

f) adding the product of Step e) to a mixture of a base selected from triethylamine or diisopropylethylamine and a solvent selected from toluene, benzene, xylenes, or n-heptane to which diphenylphosphoryl azide (DPPA) was added, and stirring at a temperature from 0° C. to 150° C. to produce the isocyanate of formula (31);

g) adding the product of Step f) to a solvent selected from toluene, benzene, xylenes, or n-heptane to which methanol was added and stirring at a temperature from 0° C. to 150° C. to produce the carbamate of formula (32);

h) adding the product of Step g) to a mixture of carbon tetrachloride and acetonitrile to which water, sodium periodate, and ruthenium(III) chloride were added, and stirring at a temperature from −40° C. to 80° C. to produce the carboxylic acid of formula (33);

i) adding the product of Step h) to a solvent selected from water, acetic acid, or 1,4-dioxane to which aqueous hydrochloric acid at a concentration of from 0.01 M to 12 M was added, and stirring at a temperature from 0° C. to 115° C. to produce a compound of Formula IVa;

j) converting the product of Step i) to a compound of Formula IV, and further converting, if desired, to a pharmaceutically acceptable salt by known means.

More preferred is a process for the preparation of a compound of Formula IV wherein R is $C_1$–$C_{10}$ alkyl or $C_3$–$C_{10}$ cycloalkyl, and pharmaceutically acceptable salts thereof, which comprises:

a) adding ethyl cyanoacetate to a mixture of a chiral cyclopentanone of formula (21) in toluene to which acetic acid and ammonium acetate were added, and heating the mixture at reflux to produce the alkene of formula (22);

b) adding the product of Step a) above to a mixture of benzylmagnesium chloride in dry tetrahydrofuran at −100° C. to −20° C. to produce the addition products of formulas (23a) and (23b);

c) adding the products of Step b) above to a mixture of potassium hydroxide in ethylene glycol, and heating the mixture at 100° C. to 200° C. to produce the hydrolysis products of formulas (24a) and (24b);

d) contacting the products of Step c) above with (R)-α-methyl-benzylamine in ethyl acetate, and recrystallizing the salt so formed from ethyl acetate to produce the enriched diastereomer of formula (25a) as the (R)-α-methyl-benzylamine salt;

e) adding the product of Step d) to aqueous hydrochloric acid and stirring to produce the carboxylic acid of formula (26);

f) adding the product of Step e) to a mixture of triethylamine and toluene to which diphenylphosphoryl azide (DPPA) was added, and refluxing to produce the isocyanate of formula (31);

g) adding the product of Step f) to a mixture of methanol and toluene and refluxing to produce the carbamate of formula (32);

h) adding the product of Step g) to a mixture of carbon tetrachloride and acetonitrile to which water, sodium periodate, and ruthenium(III) chloride were added, and stirring to produce the carboxylic acid of formula (33);

i) adding the product of Step h) to 1,4-dioxane to which aqueous hydrochloric acid at a concentration of 6 M was added, and stirring to produce a compound of Formula IVa;

j) converting the product of Step i) to a compound of Formula IV, and further converting, if desired, to a pharmaceutically acceptable salt by known means.

Also preferred is a process for the preparation of a compound of Formula IV, further characterized in that the intermediate product (31):

formed is further reacted, without isolation, with methanol to produce the carbamate of formula (32):

Still further, the invention provides a process for the preparation of a compound of Formula IV:

IV wherein R is $C_1$–$C_{10}$ alkyl or $C_3$–$C_{10}$ cycloalkyl, and pharmaceutically acceptable salts thereof, which comprises:

a) adding a cyanoacetate of formula (A):

NC⌒$CO_2R_1$, wherein $R_1$ is alkyl or benzyl, to a mixture of a chiral cyclopentanone of formula (21):

a solvent, a carboxylic acid, and a Knoevenagel reaction catalyst, and stirring the mixture in the presence of a means of removing water to produce the alkene of formula (22):

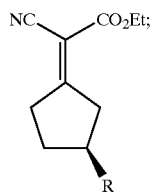

b) adding the product of Step a) above to a mixture of benzylmagnesium chloride or benzylmagnesium iodide, in a solvent to produce the addition of products of formulas (23a):

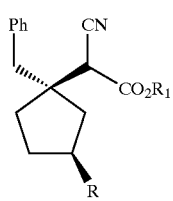

and (23b):

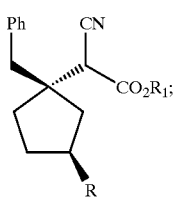

c) adding the products of Step b) above to a mixture of a base selected from potassium hydroxide, sodium hydroxide, lithium hydroxide, and cesium hydroxide, in a solvent, and stirring, and then acidifying to produce the carboxylic acids of formulas (24a):

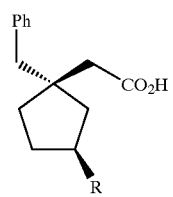

and (24b):

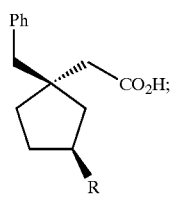

or adding the products of Step b) above to an acid mixture, and stirring to produce the carboxylic acids of formulas (24a):

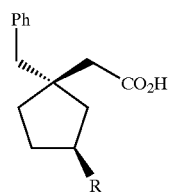

and (24b):

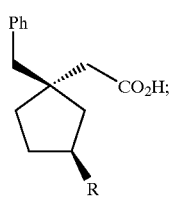

d) contacting the products of Step c) above with an amine in a solvent, and recrystallizing the salt so formed to produce the enriched diastereomer of formula (25):

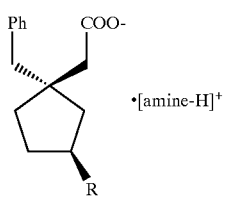

as the amine salt; and e) converting the product of Step d) to a carboxylic acid of formula (26):

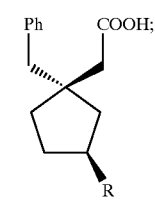

f) adding oxalyl chloride to a mixture of the product of Step e), a solvent, and N,N-dimethylformamide (DMF), and stirring to produce the acid chloride of formula (34):

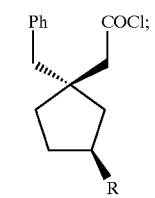

g) adding the product of Step f) to a mixture of tert-butyl alcohol, a solvent, and a tertiary amine base, and stirring to produce the ester of formula (35):

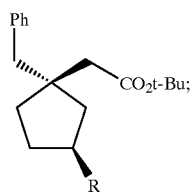

h) adding the product of Step g) to a mixture of carbon tetrachloride or ethyl acetate, and acetonitrile, water, sodium periodate, and ruthenium(III) chloride, and stirring to produce the carboxylic acid of formula (36):

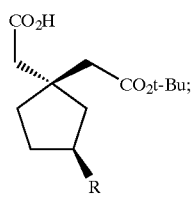

i) adding the product of Step h) to a mixture of a solvent, methanol, and (trimethylsilyl)diazomethane, and stirring to produce the bis ester of formula (37):

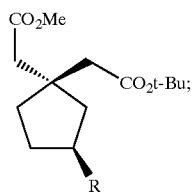

or adding the product of Step h) to a mixture of iodomethane, a solvent, and a base, and stirring to produce the bis ester of formula (37):

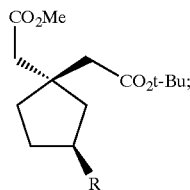

j) adding an acid to a mixture of the product from Step i) and a solvent and stirring to produce the carboxylic acid of formula (38):

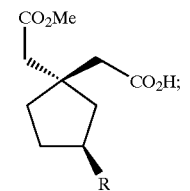

k) adding the product of Step j) to a mixture of a tertiary amine base, a solvent, and diphenylphosphoryl azide (DPPA), and stirring to produce the isocyanate of formula (39):;

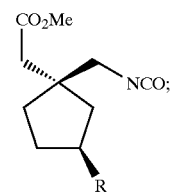

or adding the product of Step j) above to ethyl chloroformate or isobutyl chloroformate and a base in a solvent at a temperature of from −40° C. to 78° C., followed by adding a solution of sodium azide in water and tetrahydrofuran or acetone, followed by adding toluene or benzene, and refluxing to produce isocyanate of formula (39):

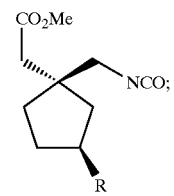

l) adding the product of Step k) to a mixture of a solvent and methanol, and stirring to produce the carbamate of formula (40):

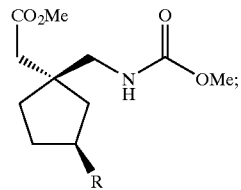

m) adding the product of Step l) to a mixture of a solvent and hydrochloric acid, and stirring to produce a compound of formula (IVa):

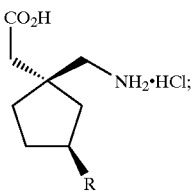

n) converting the product of Step m) to a compound of Formula IV:

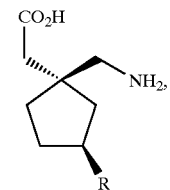

and further converting, if desired, to a pharmaceutically acceptable salt by known means.

This process is outlined in Scheme 6.

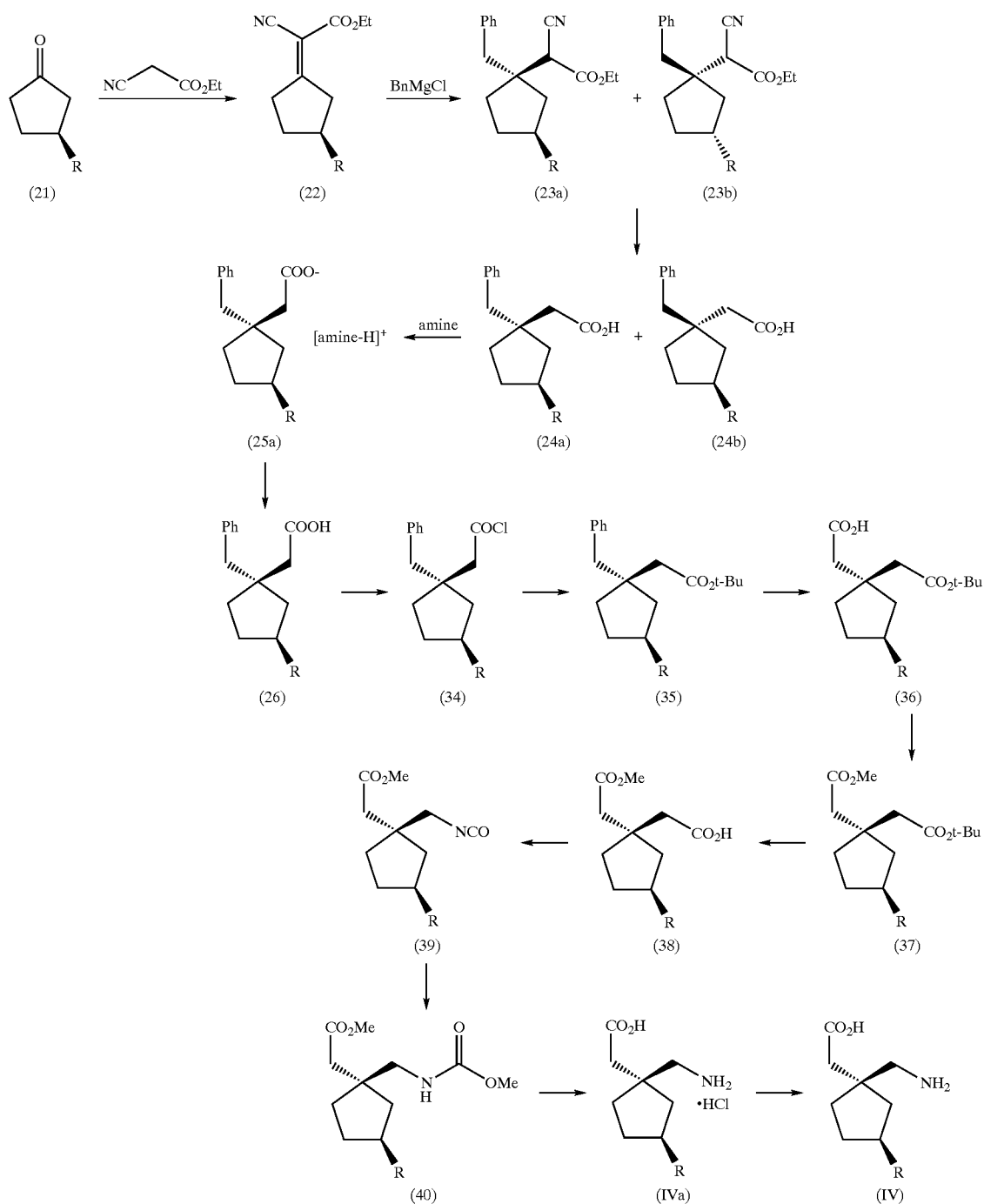

Preferred is a process for the preparation of a compound of Formula IV wherein R is $C_1$–$C_{10}$ alkyl or $C_3$–$C_{10}$ cycloalkyl, and pharmaceutically acceptable salts thereof, which comprises:

a) adding ethyl cyanoacetate to a mixture of a chiral cyclopentanone of formula (21) in a solvent selected from toluene, benzene, xylenes, or n-heptane to which acetic acid and β-alanine or ammonium acetate were added, and stirring the mixture at a temperature from 0° C. to 150° C. to produce the alkene of formula (22);

b) adding the product of Step a) above to a mixture of benzylmagnesium chloride in a dry solvent selected from tetrahydrofuran, 1,4-dioxane, n-heptane, toluene, ethyl ether, or tert-butyl methyl ether at a temperature from −100° C. to 110° C. to produce the addition products of formulas (23 a) and (23b);

c) adding the products of Step b) above to a mixture of a base selected from potassium hydroxide, sodium hydroxide, lithium hydroxide, or cesium hydroxide in a solvent selected from ethylene glycol, 2-methoxyethyl ether, 1,4-dioxane, or diethylene glycol and stirring the mixture at a temperature from 25° C. to 250° C. to produce the carboxylic acids of formulas (24a) and (24b);

d) contacting the products of Step c) above with (R)-α-methyl-benzylamine in a solvent selected from ethyl acetate, acetonitrile, tetrahydrofuran, or 1,4-dioxane at a temperature from −40° C. to 105° C., and recrystallizing the salt so formed from a solvent selected from ethyl acetate, acetonitrile, tetrahydrofuran, 1,4-dioxane, tert-butyl methyl ether, toluene, or n-heptane to produce the enriched diastereomer of formula (25a) as the (R)-α-methyl-benzylamine salt;

e) adding the product of Step d) to a mixture selected from aqueous hydrochloric acid, hydrochloric acid dissolved in acetic acid, or hydrochloric acid dissolved in acetic acid to which water was added and stirring at a temperature from −40° C. to 115° C. to produce the carboxylic acid of formula (26);

f) adding oxalyl chloride to a mixture of the product of Step e) and a solvent selected from dichloromethane, chloroform, ethyl ether, toluene, or tert-butyl methyl ether to which 0.01 mol percent to 10 mol percent of N,N-dimethylformamide (DMF) was added, and stirring at a temperature from −40° C. to 110° C. to produce the acid chloride of formula (34);

g) adding the product of Step f) to a mixture of tert-butyl alcohol in a solvent selected from dichloromethane, chloroform, ethyl ether, toluene, or tert-butyl methyl ether to which N,N-diisopropylethylamine (DIPEA) or triethylamine was added, and stirring at a temperature from −40° C. to 110° C. to produce the ester of formula (35);

h) adding the product of Step g) to a mixture of carbon tetrachloride and acetonitrile to which water, sodium periodate, and ruthenium(III) chloride were added, and stirring at a temperature from −40° C. to 80° C. to produce the carboxylic acid of formula (36);

i) adding the product of Step h) to a solvent selected from toluene, benzene, xylenes, or n-heptane to which methanol and (trimethylsilyl)diazomethane were added, and stirring at a temperature from 0° C. to 150° C. to produce the bis ester of formula (37);

j) adding trifluoroacetic acid (TFA) to a mixture of the product from Step i) and a solvent selected from dichloromethane, chloroform, 1,4-dioxane, tetrahydrofuran, ethyl ether, or tert-butyl methyl ether and stirring at a temperature from −40° C. to 110° C. to produce the carboxylic acid of formula (38);

k) adding the product of Step j) to a mixture of a base selected from triethylamine or diisopropylethylamine and a solvent selected from toluene, benzene, xylenes, or n-heptane to which diphenylphosphoryl azide (DPPA) was added, and stirring at a temperature from 0° C. to 150° C. to produce the isocyanate of formula (39);

l) adding the product of Step k) to a solvent selected from toluene, benzene, xylenes, or n-heptane to which methanol was added and stirring at a temperature from 0° C. to 150° C. to produce the carbamate of formula (40);

m) adding the product of Step l) to a solvent selected from water, acetic acid, or 1,4-dioxane to which aqueous hydrochloric acid at a concentration of from 0.01 M to 12 M was added, and stirring at a temperature from 0° C. to 115° C. to produce a compound of Formula IVa;

n) converting the product of Step m) to a compound of Formula IV, and further converting, if desired, to a pharmaceutically acceptable salt by known means.

More preferred is a process for the preparation of a compound of Formula IV wherein R is $C_1$–$C_{10}$ alkyl or $C_3$–$C_{10}$ cycloalkyl, and pharmaceutically acceptable salts thereof, which comprises:

a) adding ethyl cyanoacetate to a mixture of a chiral cyclopentanone of formula (21) in toluene to which acetic acid and ammonium acetate were added, and heating the mixture at reflux to produce the alkene of formula (22);

b) adding the product of Step a) above to a mixture of benzylmagnesium chloride in dry tetrahydrofuran at −100° C. to −20° C. to produce the addition products of formulas (23a) and (23b);

c) adding the products of Step b) above to a mixture of potassium hydroxide in ethylene glycol, and heating the mixture at 100° C. to 200° C. to produce the hydrolysis products of formulas (24a) and (24b);

d) contacting the products of Step c) above with (R)-α-methyl-benzylamine in ethyl acetate, and recrystallizing the salt so formed from ethyl acetate to produce the enriched diastereomer of formula (25a) as the (R)-α-methyl-benzylamine salt;

e) adding the product of Step d) to aqueous hydrochloric acid and stirring to produce the carboxylic acid of formula (26);

f) adding oxalyl chloride to a mixture of the product of Step e) and dichloromethane to which a catalytic amount of N,N-dimethylformamide (DMF) was added, and stirring to produce the acid chloride of formula (34);

g) adding the product of Step f) to a mixture of tert-butyl alcohol in dichloromethane to which N,N-diisopropylethylamine (DIPEA) was added, and stirring to produce the ester of formula (35);

h) adding the product of Step g) to a mixture of carbon tetrachloride and acetonitrile to which water, sodium periodate, and ruthenium(III) chloride were added, and stirring to produce the carboxylic acid of formula (36);

i) adding the product of Step h) to a mixture of methanol and toluene to which (trimethylsilyl)diazomethane was added, and stirring to produce the bis ester of formula (37);

j) adding trifluoroacetic acid (TFA) to a mixture of the product from Step i) and dichloromethane, and stirring to produce the carboxylic acid of formula (38);

k) adding the product of Step j) to a mixture of triethylamine and toluene to which diphenylphosphoryl azide (DPPA) was added, and refluxing to produce the isocyanate of formula (39);

l) adding the product of Step k) to a mixture of methanol and toluene, and refluxing to produce the carbamate of formula (40);

m) adding the product of Step l) to 1,4-dioxane to which aqueous hydrochloric acid at a concentration of 6 M was added, and stirring to produce a compound of Formula IVa;

n) converting the product of Step m) to a compound of Formula IV, and further converting, if desired, to a pharmaceutically acceptable salt by known means.

Also preferred is a process for the preparation of a compound of Formula IV, further characterized in that the intermediate product (34):

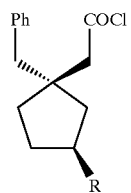

formed is further reacted, without isolation, with tert-butyl alcohol to produce the ester of formula (35):

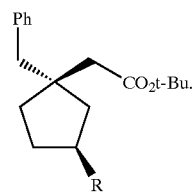

Also preferred is a process for the preparation of a compound of Formula IV, further characterized in that the intermediate product (39):

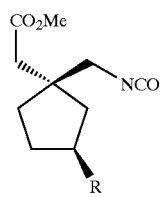

formed is further reacted, without isolation, with methanol to produce the carbamate of formula (40):

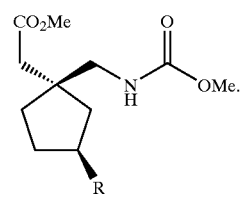

Also preferred is a process for the preparation of a compound of Formula IV, further characterized in that the intermediate product (34):

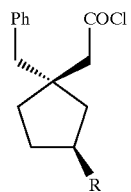

formed is further reacted, without isolation, with tert-butyl alcohol to produce the ester of formula (35);

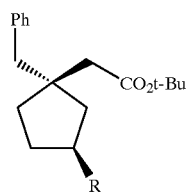

and the intermediate product (39):

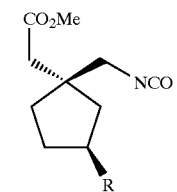

formed is further reacted, without isolation, with methanol to produce the carbamate of formula (40):

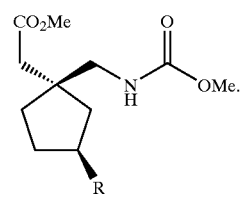

Further, the invention provides a process for the preparation of a compound of formula (6):

(6)

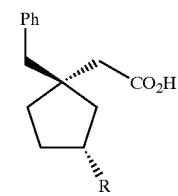

wherein R is $C_1$–$C_{10}$ alkyl or $C_3$–$C_{10}$ cycloalkyl, and pharmaceutically acceptable salts thereof, which comprises:

a) adding a cyanoacetate of formula (A):

wherein $R_1$ is alkyl or benzyl, to a mixture of a chiral cyclopentanone of formula (1):

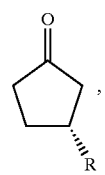

a solvent, a carboxylic acid, and a Knoevenagel reaction catalyst, and stirring the mixture in the presence of a means of removing water to produce the alkene of formula (2):

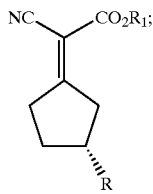

b) adding the product of Step a) above to a mixture of benzylmagnesium chloride, benzylmagnesium bromide, or benzylmagnesium iodide, in a solvent to produce the addition products of formulas (3a):

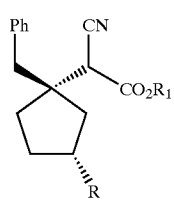

and (3b)

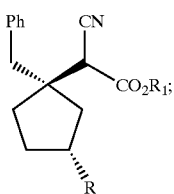

c) adding the products of Step b) above to a mixture of a base selected from potassium hydroxide, sodium hydroxide, lithium hydroxide, and cesium hydroxide, and a solvent, and stirring, and then acidifying to produce the carboxylic acids of formulas (4a):

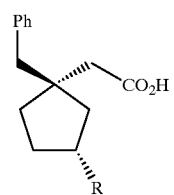

and (4b):

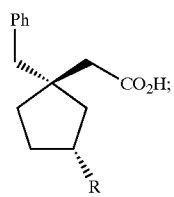

or adding the products of Step b) above to an acid mixture and stirring to produce the carboxylic acids of formulas (4a):

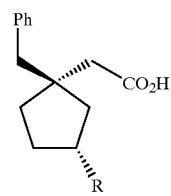

and (4b):

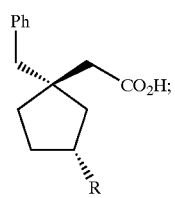

d) contacting the products of Step c) above with an amine in a solvent, and recrystallizing the salt so formed to produce the enriched diastereomer of formula (5):

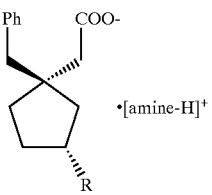

as the amine salt; and e) converting the product of Step d) to a carboxylic acid of formula (6):

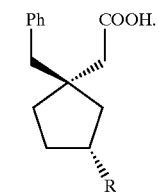

This process is outlined in Scheme 7.

Scheme 7

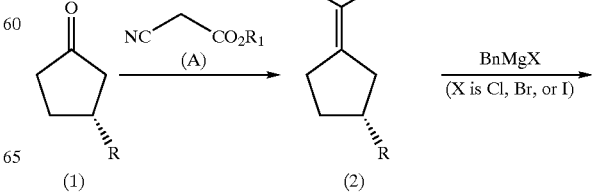

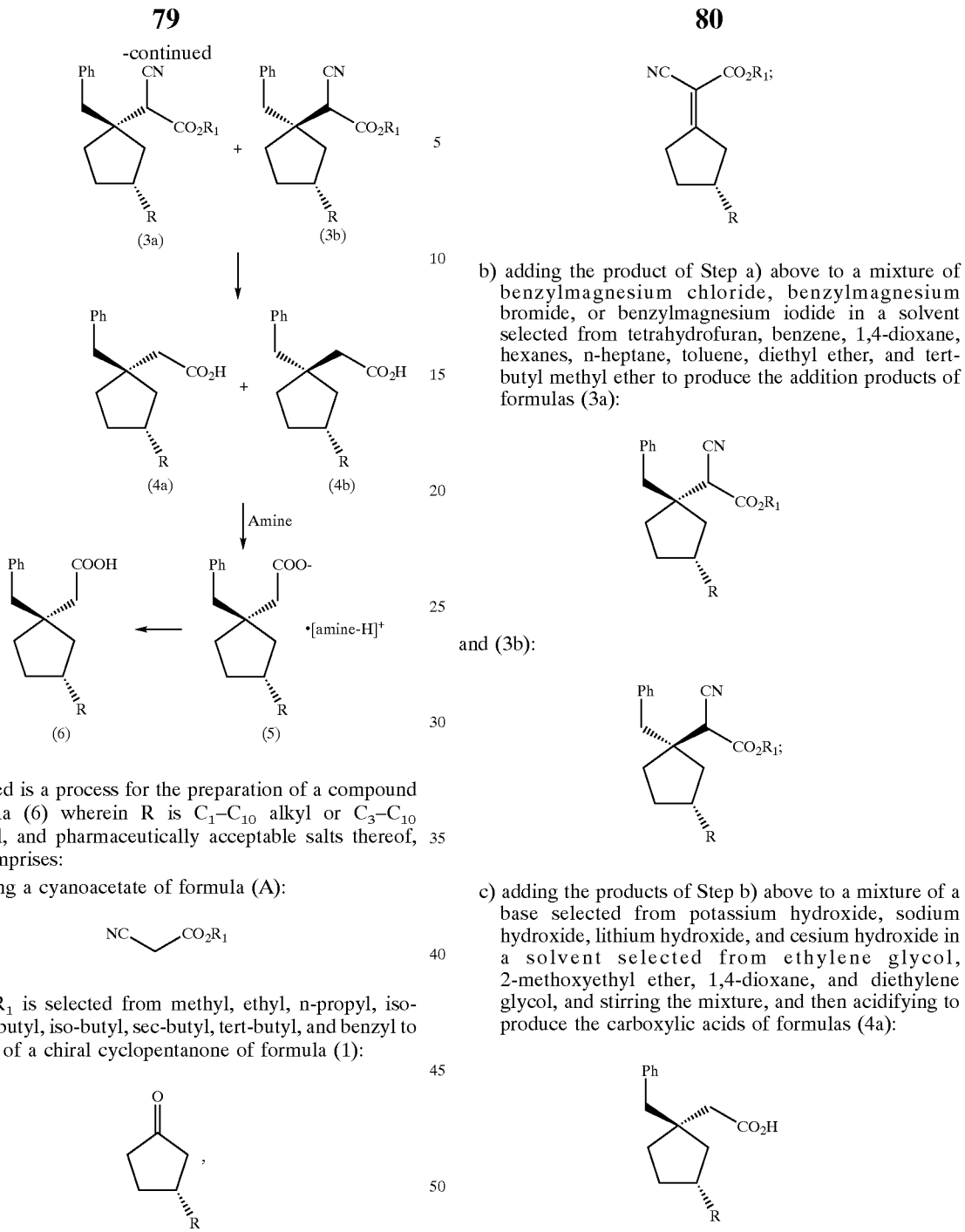

b) adding the product of Step a) above to a mixture of benzylmagnesium chloride, benzylmagnesium bromide, or benzylmagnesium iodide in a solvent selected from tetrahydrofuran, benzene, 1,4-dioxane, hexanes, n-heptane, toluene, diethyl ether, and tert-butyl methyl ether to produce the addition products of formulas (3a):

and (3b):

c) adding the products of Step b) above to a mixture of a base selected from potassium hydroxide, sodium hydroxide, lithium hydroxide, and cesium hydroxide in a solvent selected from ethylene glycol, 2-methoxyethyl ether, 1,4-dioxane, and diethylene glycol, and stirring the mixture, and then acidifying to produce the carboxylic acids of formulas (4a):

and (4b):

or adding the products of Step b) above to an acid mixture selected from 6–12 M HCl, 12 M $H_2SO_4$, 10%–48% wt/wt hydrobromic acid, and HBr in aqueous acetic acid, and stirring to produce the carboxylic acids of formulas (4a):

Preferred is a process for the preparation of a compound of formula (6) wherein R is $C_1$–$C_{10}$ alkyl or $C_3$–$C_{10}$ cycloalkyl, and pharmaceutically acceptable salts thereof, which comprises:

a) adding a cyanoacetate of formula (A):

wherein $R_1$ is selected from methyl, ethyl, n-propyl, iso-propyl, n-butyl, iso-butyl, sec-butyl, tert-butyl, and benzyl to a mixture of a chiral cyclopentanone of formula (1):

a solvent selected from tetrahydrofuran, 1,4-dioxane, tert-butylmethylether, chloroform, dichloromethane, acetonitrile, ethyl ether, ethyl acetate, hexanes, N,N-dimethylformamide, dimethylsulfoxide, ethanol, tert-butanol, toluene, benzene, xylenes, and n-heptane, acetic acid, and a Knoevenagel reaction catalyst selected from β-alanine, ammonium acetate, and piperidine, and stirring the mixture in the presence of a means of removing water selected from azeotropic distillation, activated molecular sieves, anhydrous magnesium sulfate, anhydrous sodium sulfate, anhydrous sodium carbonate, anhydrous potassium carbonate, anhydrous cesium carbonate, trimethyl orthoformate, and triethyl orthoformate to produce the alkene of formula (2):

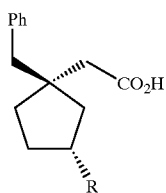

and (4b):

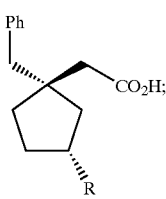

d) contacting the products of Step c) above with an amine selected from (S)-α-methyl-benzylamine, (R)-α-methyl-benzylamine, (R)-(+)-1-(naphthyl)ethylamine, (S)-(+)-1-(naphthyl)ethylamine, triethylamine, diisopropylethylamine, dicyclohexylamine, benzylamine, dibenzylamine, morpholine, N-methylmorpholine, piperidine, N-methylpiperidine, and pyridine in a solvent selected from N,N-dimethylformamide, chloroform, benzene, xylenes, hexanes, acetone, ethanol, methanol, iso-propanol, diethyl ether, dichloromethane, benzene, toluene, n-pentane, n-hexane, n-heptane, ethyl acetate, acetonitrile, tert-butyl methyl ether, tetrahydrofuran, and 1,4-dioxane, and recrystallizing the salt so formed to produce the enriched diastereomer of formula (5):

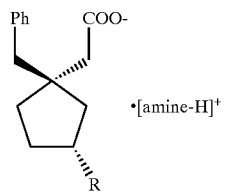

as the amine salt; and e) adding the product of Step d) to a mixture selected from aqueous hydrochloric acid, aqueous sulfuric acid, aqueous acetic acid, hydrochloric acid dissolved in acetic acid, and hydrochloric acid dissolved in acetic acid and water, and stirring to produce the carboxylic acid of formula (6):

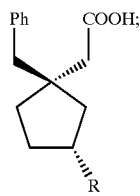

or partitioning the product of Step d) between a mixture of aqueous hydrochloric acid and a solvent selected from chloroform, dichloromethane, ethyl acetate, ethyl ether, tetrahydrofuran, 1,4-dioxane, toluene, and tert-butylmethylether, and drying and evaporating the organic layer to produce the carboxylic acid of formula (6):

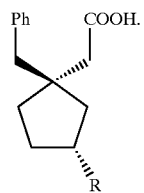

More preferred is a process for the preparation of a compound of formula (6) wherein R is $C_1$–$C_{10}$ alkyl or $C_3$–$C_{10}$ cycloalkyl, and pharmaceutically acceptable salts thereof, which comprises:

a) adding a cyanoacetate of formula (A):

wherein $R_1$ is ethyl, to a mixture of a chiral cyclopentanone of formula (1):

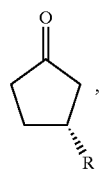

toluene, acetic acid, and a Knoevenagel reaction catalyst which is ammonium acetate, and heating the mixture at reflux over a Dean-Stark trap to produce the alkene of formula (2):

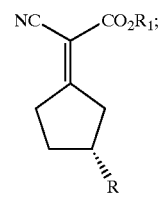

b) adding the product of Step a) above to a mixture of benzylmagnesium chloride in dry tetrahydrofuran at −100° C. to 25° C. to produce the addition products of formulas (3a):

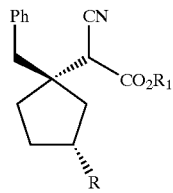

and (3b):

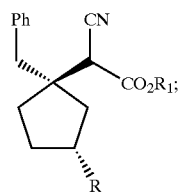

c) adding the products of Step b) above to a mixture of potassium hydroxide in ethylene glycol, and heating the mixture at 100° C. to 200° C., and then acidifying to produce the hydrolysis products of formulas (4a):

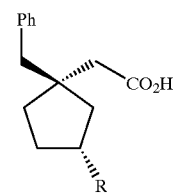

and (4b)

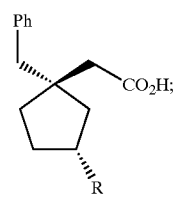

d) contacting the products of Step c) above with (S)-α-methyl-benzylamine in ethyl acetate, and recrystallizing the salt so formed from ethyl acetate to produce the enriched diastereomer of formula (5):

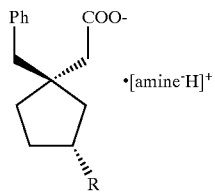

as the (S)-α-methyl-benzylamine salt;

e) adding the product of Step d) to aqueous hydrochloric acid and stirring to produce the carboxylic acid of formula (6):

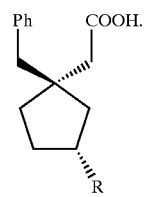

Further, the invention provides a process for the preparation of a compound of formula (26):

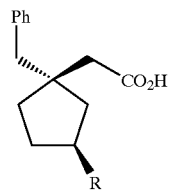

wherein R is $C_1$–$C_{10}$ alkyl or $C_3$–$C_{10}$ cycloalkyl, and pharmaceutically acceptable salts thereof, which comprises:

a) adding a cyanoacetate of formula (A):

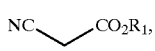

wherein $R_1$ is alkyl or benzyl, to a mixture of a chiral cyclopentanone of formula (21):

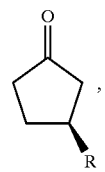

a solvent, a carboxylic acid, and a Knoevenagel reaction catalyst, and stirring the mixture in the presence of a means of removing water to produce the alkene of formula (22):

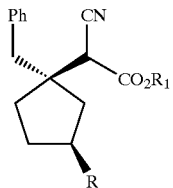

b) adding the product of Step a) above to a mixture of benzylmagnesium chloride or benzylmagnesium iodide, in a solvent to produce the addition of products of formulas (23a):

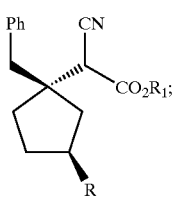

and (23b):

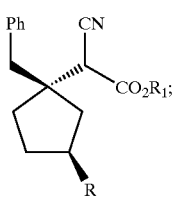

c) adding the products of Step b) above to a mixture of a base selected from potassium hydroxide, sodium hydroxide, lithium hydroxide, and cesium hydroxide, and a solvent, and stirring, and then acidifying to produce the carboxylic acids of formulas (24a):

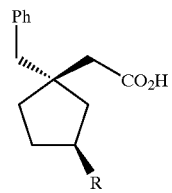

and (24b):

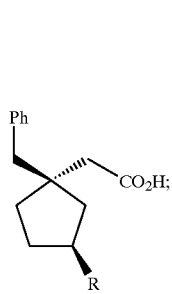

or adding the products of Step b) above to an acid mixture, and stirring to produce the carboxylic acids of formulas (24a):

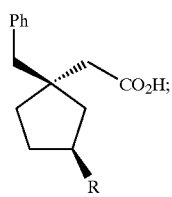

and (24b):

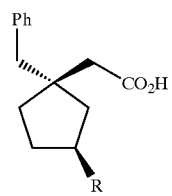

d) contacting the products of Step c) above with an amine in a solvent, and recrystallizing the salt so formed to produce the enriched diastereomer of formula (25):

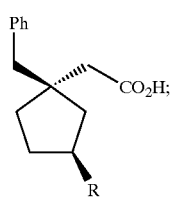

as the amine salt; and e) converting the product of Step d) to a carboxylic acid of formula (26):

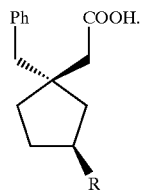

This process is outlined in Scheme 8.

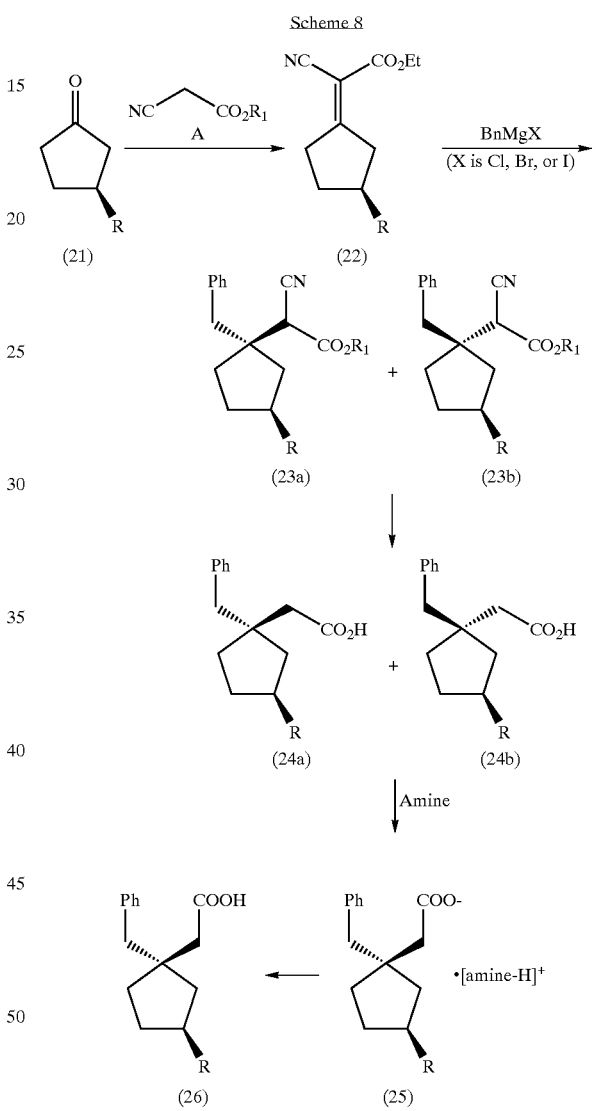

Preferred is a process for the preparation of a compound of formula (26) wherein R is $C_1$–$C_{10}$ alkyl or $C_3$–$C_{10}$ cycloalkyl, and pharmaceutically acceptable salts thereof, which comprises:

a) adding a cyanoacetate of formula (A)

wherein $R_1$ is selected from methyl, ethyl, n-propyl, iso-propyl, n-butyl, iso-butyl, sec-butyl, tert-butyl, and benzyl, to a mixture of a chiral cyclopentanone of formula (21):

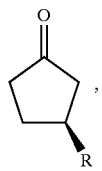

a solvent selected from tetrahydrofuran, 1,4-dioxane, tert-butylmethylether, chloroform, dichloromethane, acetonitrile, ethyl ether, ethyl acetate, hexanes, N,N-dimethylformamide, dimethylsulfoxide, ethanol, tert-butanol, toluene, benzene, xylenes, and n-heptane, acetic acid, and a Knoevenagel reaction catalyst selected from β-alanine, ammonium acetate, and piperidine, and stirring the mixture in the presence of a means of removing water selected from azeotropic distillation, activated molecular sieves, anhydrous magnesium sulfate, anhydrous cesium carbonate, trimethyl orthoformate, and triethyl orthoformate to produce the alkene of formula (22):

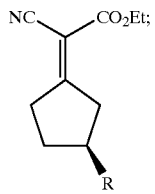

b) adding the product of Step a) above to a mixture of benzylmagnesium chloride, benzylmagnesium bromide, or benzylmagnesium iodide in a solvent selected from tetrahydrofuran, 1,4-dioxane, hexanes, n-heptane, toluene, diethyl ether, and tert-butyl methyl ether to produce the addition products of formulas (23a):

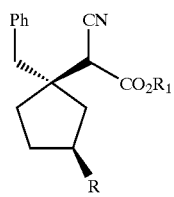

and (23b):

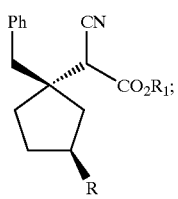

c) adding the products of Step b) above to a mixture of a base selected from potassium hydroxide, sodium hydroxide, lithium hydroxide, and cesium hydroxide in a solvent selected from ethylene glycol, 2-methoxyethyl ether, 1,4-dioxane, and diethylene glycol, and stirring the mixture, and then acidifying to produce the carboxylic acids of formulas (24a):

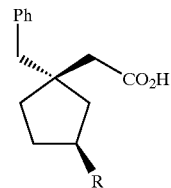

and (24b)

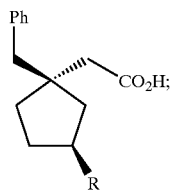

or adding the products of Step b) above to an acid mixture selected from 6–12 M HCl, 12 M $H_2SO_4$, 10%–48% wt/wt hydrobromic acid, and HBr in aqueous acetic acid, and stirring to produce the carboxylic acids of formulas (24a):

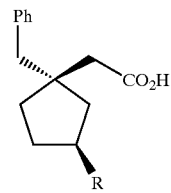

and (24b):

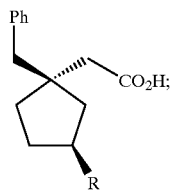

d) contacting the products of Step c) above with an amine selected from (S)-α-methyl-benzylamine, (R)-α-methyl-benzylamine, (R)-(+)-1-(naphthyl)ethylamine, (S)-(+)-1-(naphthyl)ethylamine, triethylamine, diisopropylethylamine, dicyclohexylamine, benzylamine, dibenzylamine, morpholine, N-methylmorpholine, piperidine, N-methylpiperidine, and pyridine in a solvent selected from N,N-dimethylformamide, chloroform, hexanes, acetone, ethanol, methanol, iso-propanol, diethyl ether, dichloromethane, benzene, toluene, n-pentane, n-hexane, n-heptane, ethyl acetate, acetonitrile, tert-butyl methyl ether, tetrahydrofuran, and 1,4-dioxane, and recrystallizing the salt so formed to produce the enriched diastereomer of formula (25):

as the amine salt; and

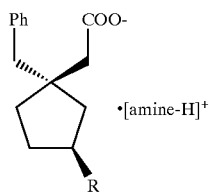

e) adding the product of Step d) to a mixture selected from aqueous hydrochloric acid, aqueous sulfuric acid, aqueous acetic acid, hydrochloric acid dissolved in acetic acid, and hydrochloric acid dissolved in acetic acid and water, and stirring to produce the carboxylic acid of formula (26):

or partitioning the product of Step d) between a mixture of aqueous hydrochloric acid and a solvent selected from chloroform, dichloromethane, ethyl acetate, ethyl ether, tetrahydrofuran, 1,4-dioxane, toluene, and tert-butylmethylether, and drying and evaporating the organic layer to produce the carboxylic acid of formula (26):

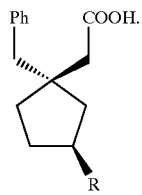

More preferred is a process for the preparation of a compound of formula (26) wherein R is $C_1$–$C_{10}$ alkyl or $C_3$–$C_{10}$ cycloalkyl, and pharmaceutically acceptable salts thereof, which comprises:

a) adding a cyanoacetate of formula (A):

wherein $R_1$ is ethyl, to a mixture of a chiral cyclopentanone of formula (21):

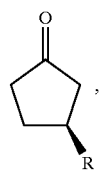

toluene, acetic acid, and a Knoevenagel reaction catalyst which is ammonium acetate, and heating the mixture at reflux over a Dean-Stark trap to produce the alkene of formula (22):

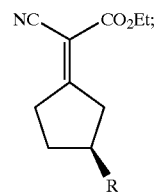

b) adding the product of Step a) above to a mixture of benzylmagnesium chloride in dry tetrahydrofuran at −100° C. to −20° C. to produce the addition products of formulas (23a):

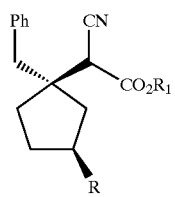

and (23b):

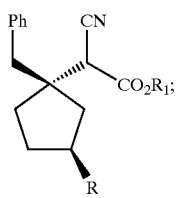

c) adding the products of Step b) above to a mixture of potassium hydroxide in ethylene glycol, and heating the mixture at 100° C. to 200° C., and then acidifying to produce the hydrolysis products of formulas (24a):

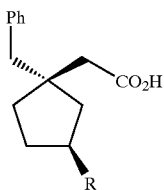

and (24b)

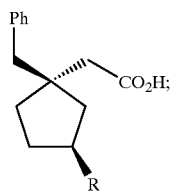

d) contacting the products of Step c) above with (R)-α-methyl-benzylamine in ethyl acetate, and recrystallizing the salt so formed from ethyl acetate to produce the enriched diastereomer of formula (25):

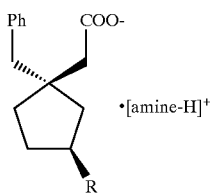

as the (R)-α-methyl-benzylamine salt; and e) adding the product of Step d) to aqueous hydrochloric acid and stirring to produce the carboxylic acid of formula (26):

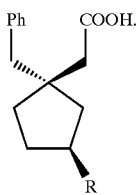

Further, the invention provides a key intermediate of formula (6):

(6)

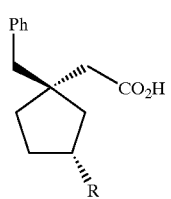

wherein R is $C_1$–$C_{10}$ alkyl or $C_3$–$C_{10}$ cycloalkyl, and pharmaceutically acceptable salts thereof.

Preferred is a compound of formula (6) and pharmaceutically acceptable salts thereof wherein R is $C_1$–$C_{10}$ alkyl.

More preferred is a compound of formula (6) and pharmaceutically acceptable salts thereof wherein R is selected from methyl, ethyl, and n-propyl.

Still more preferred is a compound of formula (6) named ((1S,3R)-1-benzyl-3-methyl-cyclopentyl)-acetic acid.

Further, the invention provides a key intermediate of formula (26):

(26)

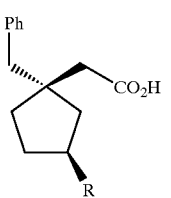

wherein R is $C_1$–$C_{10}$ alkyl or $C_3$–$C_{10}$ cycloalkyl and pharmaceutically acceptable salts thereof.

Preferred is a compound of formula (26) and pharmaceutically acceptable salts thereof wherein R is $C_1$–$C_{10}$ alkyl.

More preferred is a compound of formula (26) and pharmaceutically acceptable salts thereof wherein R is selected from methyl, ethyl, and n-propyl.

Still more preferred is a compound of formula (26) named ((1R,3S)-1-benzyl-3-methyl-cyclopentyl)-acetic acid.

Further, the invention provides a compound of Formula I, wherein R is as defined above, prepared according to any one of the processes for the preparation of a compound of Formula I described above.

Preferred is a compound of Formula I, wherein R is $C_1$–$C_{10}$ alkyl, prepared according to any one of the processes for the preparation of a compound of Formula I described above.

More preferred is a compound of Formula I wherein R is selected from methyl, ethyl, and n-propyl, prepared according to any one of the processes for the preparation of a compound of Formula I described above.

Still more preferred is a compound of Formula I selected from:

((1R,3S)-1-aminomethyl-3-methyl-cyclopentyl)-acetic acid; and ((1R,3S)-1-aminomethyl-3-methyl-cyclopentyl)-acetic acid hydrochloride, prepared according to any one of the processes for the preparation of a compound of Formula I described above.

Further, the invention provides a compound of Formula II, wherein R is as defined above, prepared according to any one of the processes for the preparation of a compound of Formula II described above.

Preferred is a compound of Formula II, wherein R is $C_1$–$C_{10}$ alkyl, prepared according to any one of the processes for the preparation of a compound of Formula II described above.

More preferred is a compound of Formula II, wherein R is selected from methyl, ethyl, and n-propyl, prepared according to any one of the processes for the preparation of a compound of Formula II described above.

Still more preferred is a compound of Formula II selected from:

((1S,3R)-1-aminomethyl-3-methyl-cyclopentyl)-acetic acid; and ((1S,3R)-1-aminomethyl-3-methyl-cyclopentyl)-acetic acid hydrochloride, prepared according to any one of the processes for the preparation of a compound of Formula II described above.

Further, the invention provides a compound of Formula III, wherein R is as defined above, prepared according to any one of the processes for the preparation of a compound of Formula III described above.

Further, the invention provides a compound of Formula IV, wherein R is as defined above, prepared according to any one of the processes for the preparation of a compound of Formula IV described above.

Further, the invention provides a compound of formula (6), wherein R is as defined above, prepared according to any one of the processes for the preparation of a compound of formula (6) described above.

Preferred is a compound of formula (6), wherein R is $C_1$–$C_{10}$ alkyl, prepared according to any one of the processes for the preparation of a compound of formula (6) described above.

More preferred is a compound of formula (6), wherein R is selected from methyl, ethyl, and n-propyl, prepared according to any one of the processes for the preparation of a compound of formula (6) described above.

Still more preferred is a compound of formula (6) named ((1S,3R)-1-benzyl-3-methyl-cyclopentyl)-acetic acid, prepared according to any one of the processes for the preparation of a compound of formula (6) described above.

Further, the invention provides a compound of formula (26), wherein R is as defined above, prepared according to any one of the processes for the preparation of a compound of formula (26) described above.

Preferred is a compound of formula (26), wherein R is $C_1$–$C_{10}$ alkyl, prepared according to any one of the processes for the preparation of a compound of formula (26) described above.

More preferred is a compound of formula (26), wherein R is selected from methyl, ethyl, and n-propyl, prepared according to any one of the processes for the preparation of a compound of formula (26) described above.

Still more preferred is a compound of formula (26) named ((1R,3S)-1-benzyl-3-methyl-cyclopentyl)-acetic acid, prepared according to any one of the processes for the preparation of a compound of formula (26) described above.

Further, the invention provides a compound of Formula I selected from:
((1R,3R)-1-aminomethyl-3-methyl-cyclopentyl)-acetic acid;
((1R,3R)-1-aminomethyl-3-methyl-cyclopentyl)-acetic acid hydrochloride;
((1R,3R)-1-aminomethyl-3-ethyl-cyclopentyl)-acetic acid;
((1R,3R)-1-aminomethyl-3-ethyl -cyclopentyl)-acetic acid hydrochloride;
((1R,3R)-1-aminomethyl-3-propyl-cyclopentyl)-acetic acid; and
((1R,3R)-1-aminomethyl-3-propyl-cyclopentyl)-acetic acid hydrochloride.

Further, the invention provides a compound of Formula II selected from:
((1S,3R)-1-aminomethyl-3-methyl-cyclopentyl)-acetic acid;
((1S,3R)-1-aminomethyl-3-methyl-cyclopentyl)-acetic acid hydrochloride;
((1S,3R)-1-aminomethyl-3-ethyl-cyclopentyl)-acetic acid;
((1S,3R)-1-aminomethyl-3-ethyl-cyclopentyl)-acetic acid hydrochloride;
((1S,3R)-1-aminomethyl-3-propyl-cyclopentyl)-acetic acid; and
((1S,3R)-1-aminomethyl-3-propyl-cyclopentyl)-acetic acid hydrochloride.

Further, the invention provides compounds selected from:
E-Cyano-((R)-3-methyl-cyclopentylidene)-acetic acid ethyl ester;
Z-Cyano-((R)-3-methyl-cyclopentylidene)-acetic acid ethyl ester;
(R)-((1S,3R)-1-Benzyl-3-methyl-cyclopentyl)-cyano-acetic acid ethyl ester;
(S)-((1S,3R)-1-Benzyl-3-methyl-cyclopentyl)-cyano-acetic acid ethyl ester;
(R)-((1R,3R)-1-Benzyl-3-methyl-cyclopentyl)-cyano-acetic acid ethyl ester;
(S)-((1R,3R)-1-Benzyl-3-methyl-cyclopentyl)-cyano-acetic acid ethyl ester;
((1S,3R)-1-Isocyanatomethyl-3-methyl-cyclopentylmethyl)-benzene;
((1S,3R)-1-Benzyl-3-methyl-cyclopentylmethyl)-carbamic acid methyl ester;
[(1S,3R)-1-(Methoxycarbonylamino-methyl)-3-methyl-cyclopentyl]-acetic acid;
((1S,3R)-1-Benzyl-3-methyl-cyclopentyl)-acetic acid methyl ester;
(1S,3 R)-1-Methoxycarbonylmethyl-3-methyl-cyclopentyl)-acetic acid;
((1R,3R)-1-Isocyanatomethyl-3-methyl-cyclopentyl)-acetic acid methyl ester;
[(1R,3R)-1-(Methoxycarbonylamino-methyl)-3-methyl-cyclopentyl]-acetic acid methyl ester;
((1S,3R)-1-Benzyl-3-methyl-cyclopentyl)-acetic acid tert-butyl ester;
[(1S,3R)-1-Carboxymethyl-3-methyl-cyclopentyl]-acetic acid tert-butyl ester;
[(1S,3R)-1-Methoxycarbonylmethyl-3-methyl-cyclopentyl]-acetic acid tert-butyl ester;
((1R,3R)-1-Methoxycarbonylmethyl-3-methyl-cyclopentyl)-acetic acid;
((1S,3R)-1-Isocyanatomethyl-3-methyl-cyclopentyl)-acetic acid methyl ester; and
[(1S,3R)-1-(Methoxycarbonylamino-methyl)-3-methyl-cyclopentyl]-acetic acid methyl ester.

More preferred is a process for the preparation of a compound of formula (4a):

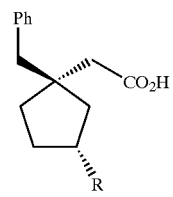

wherein R is $C_1$–$C_{10}$ alkyl or $C_3$–$C_{10}$ cycloalkyl, comprising, hydrolyzing a compound of formula (3a):

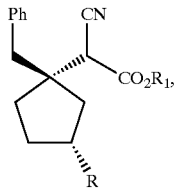

wherein $R_1$ is H, alkyl, or benzyl.

More preferred is a process for the preparation of a compound of formula (24a):

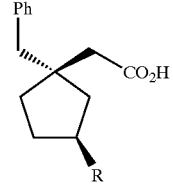

wherein R is $C_1$–$C_{10}$ alkyl or $C_3$–$C_{10}$ cycloalkyl, comprising, hydrolyzing a compound of formula (23a):

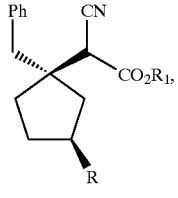

wherein $R_1$ is H, alkyl, or benzyl.

More preferred is a process for the preparation of a compound of formula (6):

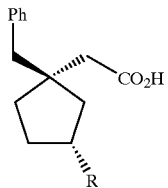

wherein R is $C_1$–$C_{10}$ alkyl or $C_3$–$C_{10}$ cycloalkyl, comprising, resolving a mixture containing compounds of formulas (4a):

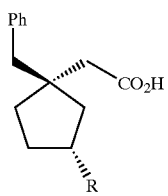

and (4b):

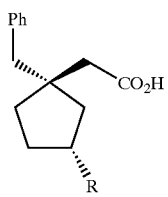

wherein R is $C_1$–$C_{10}$ alkyl or $C_3$–$C_{10}$ cycloalkyl.

More preferred is a process for the preparation of a compound of formula (26):

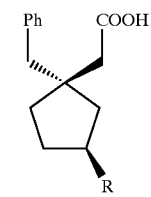

wherein R is $C_1$–$C_{10}$ alkyl or $C_3$–$C_{10}$ cycloalkyl, comprising, resolving a mixture containing compounds of formulas (24a):

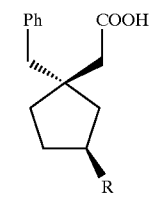

and (24b):

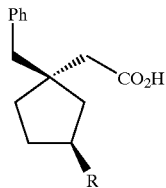

wherein R is $C_1$–$C_{10}$ alkyl or $C_3$–$C_{10}$ cycloalkyl.

More preferred is a process for the preparation of a compound of Formula I:

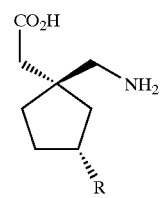

wherein R is $C_1$–$C_{10}$ alkyl or $C_3$–$C_{10}$ cycloalkyl, and pharmaceutically acceptable salt thereof, comprising, hydrolyzing a compound of formula (41):

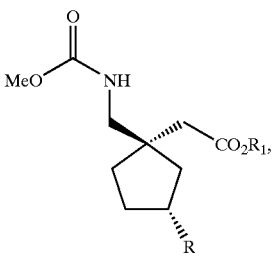

wherein $R_1$ is H, alkyl, or benzyl, and contacting the product, if desired, with an acid or a base.

More preferred is a process for the preparation of a compound of Formula II:

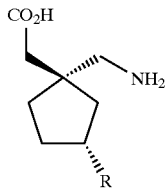

wherein R is $C_1$–$C_{10}$ alkyl or $C_3$–$C_{10}$ cycloalkyl, and pharmaceutically acceptable salt thereof; comprising, hydrolyzing a compound of formula (42):

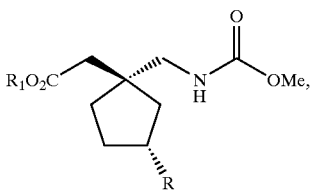

wherein $R_1$ is H, alkyl, or benzyl, and contacting the product, if desired, with an acid or a base.

More preferred is a process for the preparation of a compound of Formula III:

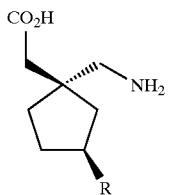

wherein R is $C_1$–$C_{10}$ alkyl or $C_3$–$C_{10}$ cycloalkyl, and pharmaceutically acceptable salt thereof, comprising, hydrolyzing a compound of formula (43):

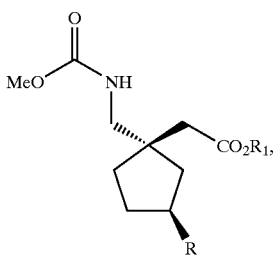

wherein $R_1$ is H, alkyl, or benzyl, and contacting the product, if desired, with an acid or a base.

More preferred is a process for the preparation of a compound of Formula IV:

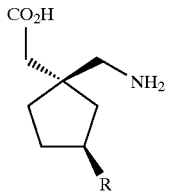

wherein R is $C_1$–$C_{10}$ alkyl or $C_3$–$C_{10}$ cycloalkyl, and pharmaceutically acceptable salt thereof, comprising, hydrolyzing a compound of formula (44):

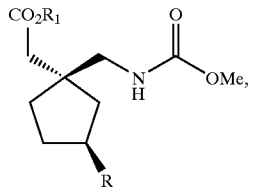

wherein $R_1$ is H, alkyl, or benzyl, and contacting the product, if desired, with an acid or a base.

DETAILED DESCRIPTION OF THE INVENTION

The instant invention is an important process as it permits the synthesis of single isomers; it is a route to stereospecific 3-substituted 5-membered rings of formula:

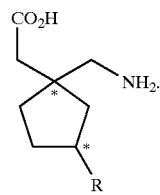

A key feature of the invention is the stereoselective preparation of a compound of formula (6) by selective fractional crystallization of a salt of formula (5) from a mixture of compounds of formulas (4a) and (4b), and conversion of a salt of formula (5) to a compound of formula (6). Another feature of the invention is the conversion of a compound of formula (2) to a mixture of compounds of formulas (3a) and (3b) wherein the yield of a compound of formula (3a) over a diastereomer of formula (3b) may be enhanced by optimizing certain reaction parameters such as, for example, temperature. Reaction of a compound of formula (2) at a relatively low temperature generally provides for a relatively higher yield of a compound of formula (3a) over (3b) than when the reaction is run at a higher temperature. The invention also provides for translation of the stereochemistry at the two chiral carbons of the cyclopentane ring of the resulting pure enantiomer of formula (6) into enantiomerically pure compounds of Formulas I or II with little or no racemization.

Another key feature of the invention is the stereoselective preparation of a compound of formula (26) by selective fractional crystallization of salt of formula (25) from a mixture of compounds of formulas (24a) and (24b), and conversion of a salt of formula (25) to a compound of formula (26). Another feature of the invention is the conversion of a compound of formula (22) to a mixture of compounds of formulas (23a) and (23b) wherein the yield of a compound of formula (23a) over a diastereomer of formula (23b) may be enhanced by optimizing certain reaction parameters such as, for example, temperature. Reaction of a compound of formula (22) at a relatively low temperature generally provides for a relatively higher yield of a compound of formula (23a) over (23b) than when the reaction is run at a higher temperature. The invention also provides for translation of the stereochemistry at the two chiral carbons of the cyclopentane ring of the resulting pure enantiomer of formula (26) into enantiomerically pure compounds of Formulas III or IV with little or no racemization.

The final products are useful as agents in the treatment of epilepsy, faintness attacks, hypokinesia, cranial disorders, neurodegenerative disorders, depression, anxiety, panic, pain, neuropathological disorders, gastrointestinal disorders such as irritable bowel syndrome (IBS), inflammation especially arthritis, sleep disorders, premenstrual syndrome, and hot flashes.

The following experimental procedures provide a novel route to be used to stereoselectively synthesize 3-substituted cyclopentyl-based analogs of gabapentin and pharmaceutically acceptable salts thereof. These routes provide access to pure stereoisomers of Formulas I, II, III, and IV:

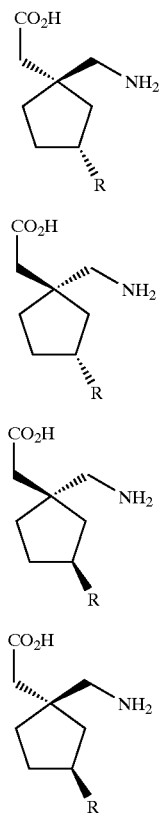

wherein R is $C_1$–$C_{10}$ alkyl or $C_3$–$C_{10}$ cycloalkyl.

Examples 1 and 3 below each show a synthesis of a compound of Formula II wherein R is methyl.

Example 2 below shows a synthesis of a compound of Formula I wherein R is methyl.

It is understood that compounds of Formulas I, II, III, or IV, or a pharmaceutically acceptable salt thereof, produced by a hydrolysis reaction such as, for example, step j) in the above process for the preparation of a compound of Formula I, or a pharmaceutically acceptable salt thereof, or the process described above wherein a compound of formula (41) is hydrolyzed, may be formed as an acid or base salt thereof, which salt may be optionally converted to a free amino acid form or a pharmaceutically acceptable salt form thereof by methods well known to a skilled person in the pharmaceutical or chemical arts.

The following terms are defined as used herein.

As used herein the term "$C_1$–$C_{10}$ alkyl" means a straight or branched alkyl group or radical containing from 1 to 10 carbon atoms. Illustrative examples of $C_1$–$C_{10}$ alkyl include methyl, ethyl, 1-propyl, 2-propyl, 1-butyl, 2-butyl, 2-methyl-1-propyl, 1,1-dimethylethyl, 1-pentyl, 2-pentyl, 3-pentyl, 2,2-dimethylpropyl, 1-hexyl, 2-hexyl, 3-hexyl, 4-methyl-1-pentyl, 1-heptyl, 2-heptyl, 3-heptyl, 4-heptyl, 5-methyl-1-hexyl, 1-octyl, 2-octyl, 3-octyl, 4-octyl, 6-methyl-1-heptyl, 5,5-dimethylhexyl, 1-nonyl, 2-nonyl, 1-decyl, and 2-decyl.

The term "$C_3$–$C_{10}$ cycloalkyl" means a cycloalkyl group or radical having from 3 to 10 carbon atoms. Illustrative examples of a $C_3$–$C_{10}$ cycloalkyl include cyclopropyl, cyclobutyl, cyclopentyl, cyclohexyl, cycloheptyl, cyclooctyl, cyclononyl and cyclodecyl.

The term "stereoisomer" means any of a group of isomers in which identical atoms are linked in the same order but differ in their spatial arrangement.

| | |
|---|---|
| * | Asterisk symbol points out an enantiomerically enriched chiral carbon atom |
| AcOH | Acetic acid |
| Alkali hydroxide | LiOH, NaOH, KOH, or CsOH |
| $NH_4OAc$ | Ammonium acetate |
| BnMgCl or $PhCH_2MgCl$ | Benzylmagnesium chloride |
| t-BuOH or tert-butyl alcohol | 1,1-Dimethylethanol |
| $^tButyl$ | 1,1-Dimethylethyl |
| $CH_2Cl_2$ | Dichloromethane |
| $CCl_4$ | Carbon tetrachloride |
| $CDCl_3$ | Deuterochloroform |
| $(CH_3)_3SiCHN_2$ | Trimethylsilyldiazomethane |
| CN | Carbon-nitrogen triple bond (nitrile) |
| $(COCl)_2$ | Oxalyl chloride |
| CsOH | Cesium hydroxide |
| de | Diastereomeric excess |
| DBU | 1,8-Diazabicyclo[5.4.0]undec-7-ene |
| DMF | N,N-Dimethylformamide |
| DMSO | Dimethylsulfoxide |
| DMSO-$d_6$ | Deuterated dimethylsulfoxide |
| ee | Enantiomeric excess |
| Et | Ethyl |
| EtOAc | Ethyl acetate |
| $Et_3N$ | Triethylamine |
| HCl | Hydrogen chloride |
| HCl (aq) | Hydrochloric acid |
| 6NHCl | 6 normal hydrochloric acid |
| HCl (g) | Hydrogen chloride (gaseous) |
| $^1H$-NMR | Proton (nuclear) magnetic resonance spectroscopy |
| IR | Infrared spectroscopy |
| J | Coupling constant in Hz |
| KOH | Potassium hydroxide |
| LCMS | Liquid chromatography-mass spectrometry |
| LiOH | Lithium hydroxide |
| Me | Methyl |
| MeO | Methoxy |
| MeCN | Acetonitrile |
| MeI | Iodomethane |
| MeOH | Methanol |
| $MgSO_4$ | Magnesium sulfate |
| MS (ES$^+$) | Positive ion electrospray mass spectrometry |
| MS (ES$^-$) | Negative ion electrospray mass spectrometry |
| MS (CI$^+$) | Positive ion chemical ionization mass spectrometry |
| MS (CI$^-$) | Negative ion chemical ionization mass spectrometry |
| m/z | mass per unit charge |
| $NCCH_2CO_2Et$ | Ethyl cyanoacetate |
| $NaIO_4$ | Sodium periodate |
| NaOH | Sodium hydroxide |
| ODS | Octadecyl-functionalized silica gel |
| Ph | Phenyl |
| (i-Pr)$_2$NEt | Diisopropylethylamine |
| $R_f$ | $R_f$ value |
| $RuCl_3$ | Ruthenium(III) chloride |
| $SOCl_2$ | Thionyl chloride |
| TFA or $CF_3CO_2H$ | Trifluoroacetic acid |
| THF | Tetrahydrofuran |

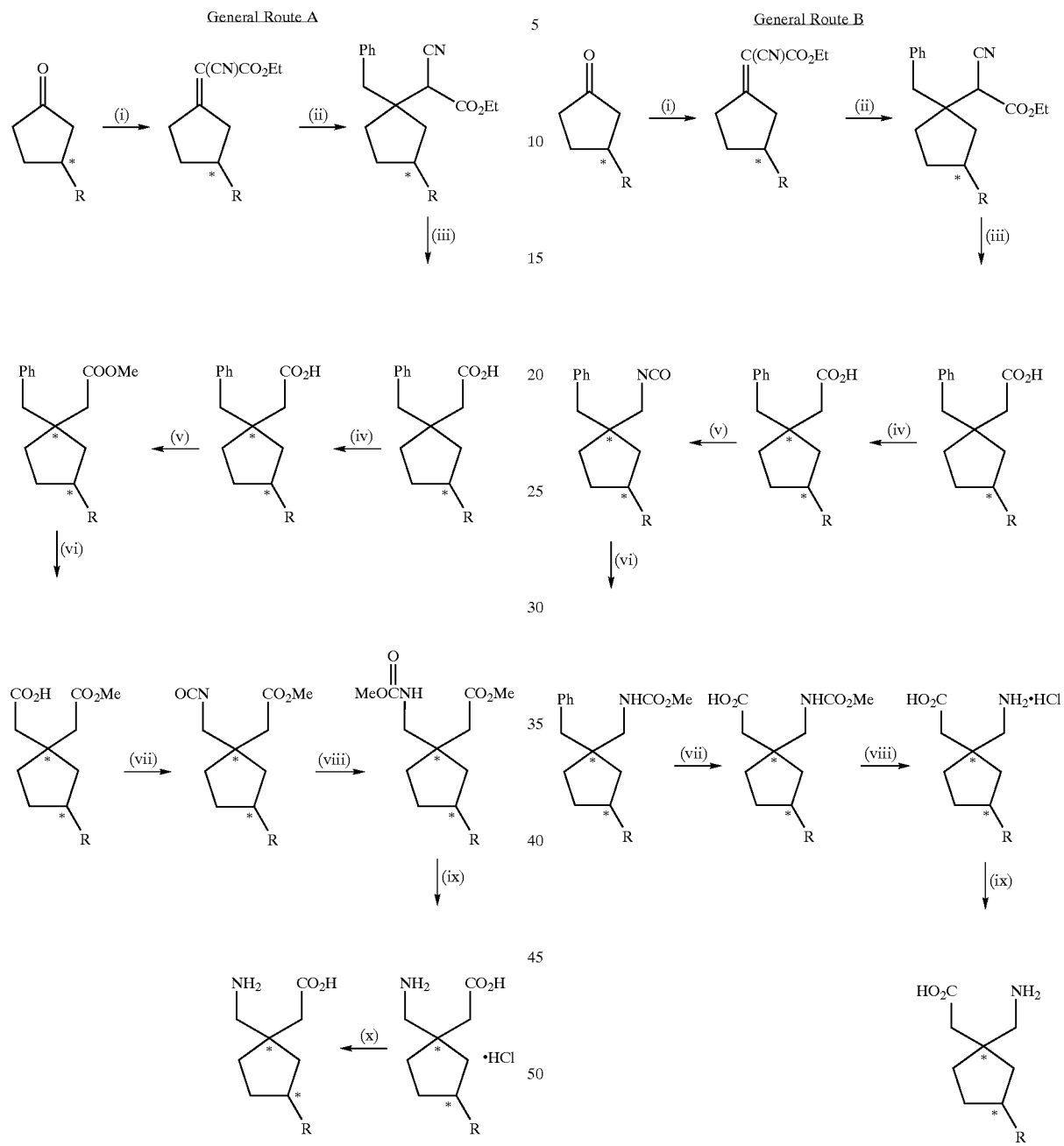

Reagents and Conditions:
(i) NCCH$_2$CO$_2$Et, catalyst (e.g., NH$_4$OAc, ACOH);
(ii) BnMgCl;
(iii) hydrolysis using, for example, alkali hydroxide (e.g., KOH);
(iv) a) resolution using a resolving agent (e.g., (R)- or (S)-α-methylbenzylamine);
  b) conversion of the enriched stereoisomer to the free acid using, for example, hydrochloric acid;
(v) esterification using, for example, MeI and DBU;
(vi) oxidation using, for example, RuCl$_3$ and NaIO$_4$;
(vii) (PhO)$_2$P(O)N$_3$ and a base (e.g., Et$_3$N);
(viii) MeOH;
(ix) hydrolysis using HCl (aq);
(x) conversion to the free amino acid using, for example, H$_2$O and alkali hydroxide (e.g., NaOH).

Reagents and Conditions:
(i) NCCH$_2$CO$_2$Et, catalyst (e.g., NH$_4$OAc, ACOH);
(ii) BnMgCl;
(iii) hydrolysis using, for example, alkali hydroxide (e.g., KOH);
(iv) a) resolution using a resolving agent (e.g., (R)- or (S)-α-methylbenzylamine);
  b) conversion of salt of enriched stereoisomer to the free acid using, for example, hydrochloric acid;
(v) (PhO)$_2$P(O)N$_3$ and base (e.g., Et$_3$N);
(vi) MeOH;
(vii) oxidation using, for example, RuCl$_3$ and NaIO$_4$;
(viii) hydrolysis using HCl (aq);
(ix) conversion to the free amino acid using, for example, H$_2$O and alkali hydroxide (e.g., NaOH).

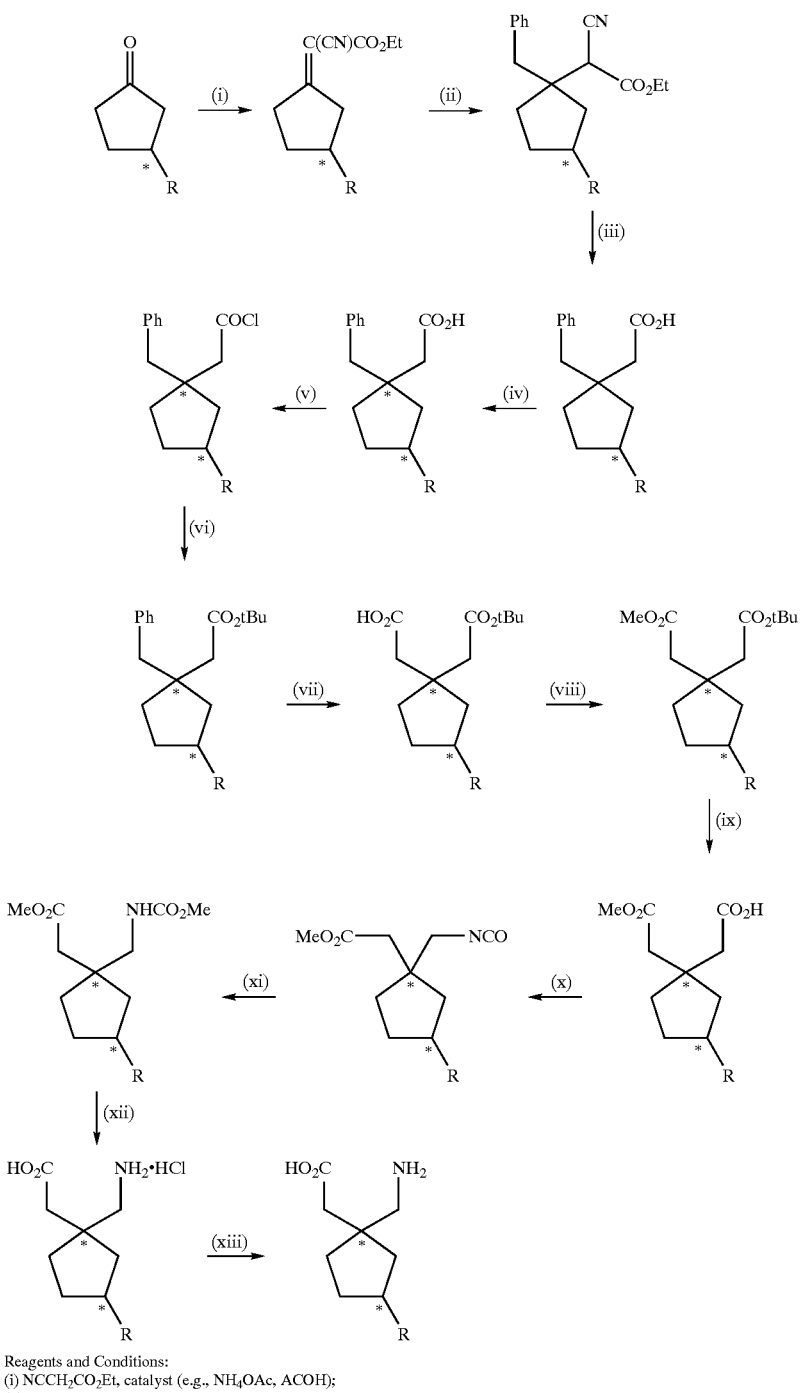

General Route C

Reagents and Conditions:
(i) NCCH$_2$CO$_2$Et, catalyst (e.g., NH$_4$OAc, ACOH);
(ii) BnMgCl;
(iii) hydrolysis using, for example, alkali hydroxide (e.g., KOH);
(iv) a) resolution using a resolving agent (e.g., (R)- or (S)-α-methylbenzylamine);
    b) conversion of salt of enriched stereoisomer to the free acid using, for example, hydrochloric acid;
(v) chlorination using, for example, (COCl)$_2$ or SOCl$_2$;
(vi) tBuOH and base (e.g., Et$_3$N);
(vii) oxidation using, for example, RuCl$_3$ and NaIO$_4$;
(viii) esterification using, for example, (CH$_3$)$_3$SiCHN$_2$ and MeOH;
(ix) dealkylation using, for example, CF$_3$CO$_2$H;
(x) (PhO)$_2$P(O)N$_3$ and a base (e.g., Et$_3$N);
(xi) MeOH;
(xiii) conversion to the free amino acid using, for example, H$_2$O and alkali hydroxide (e.g., NaOH).

EXAMPLE 1
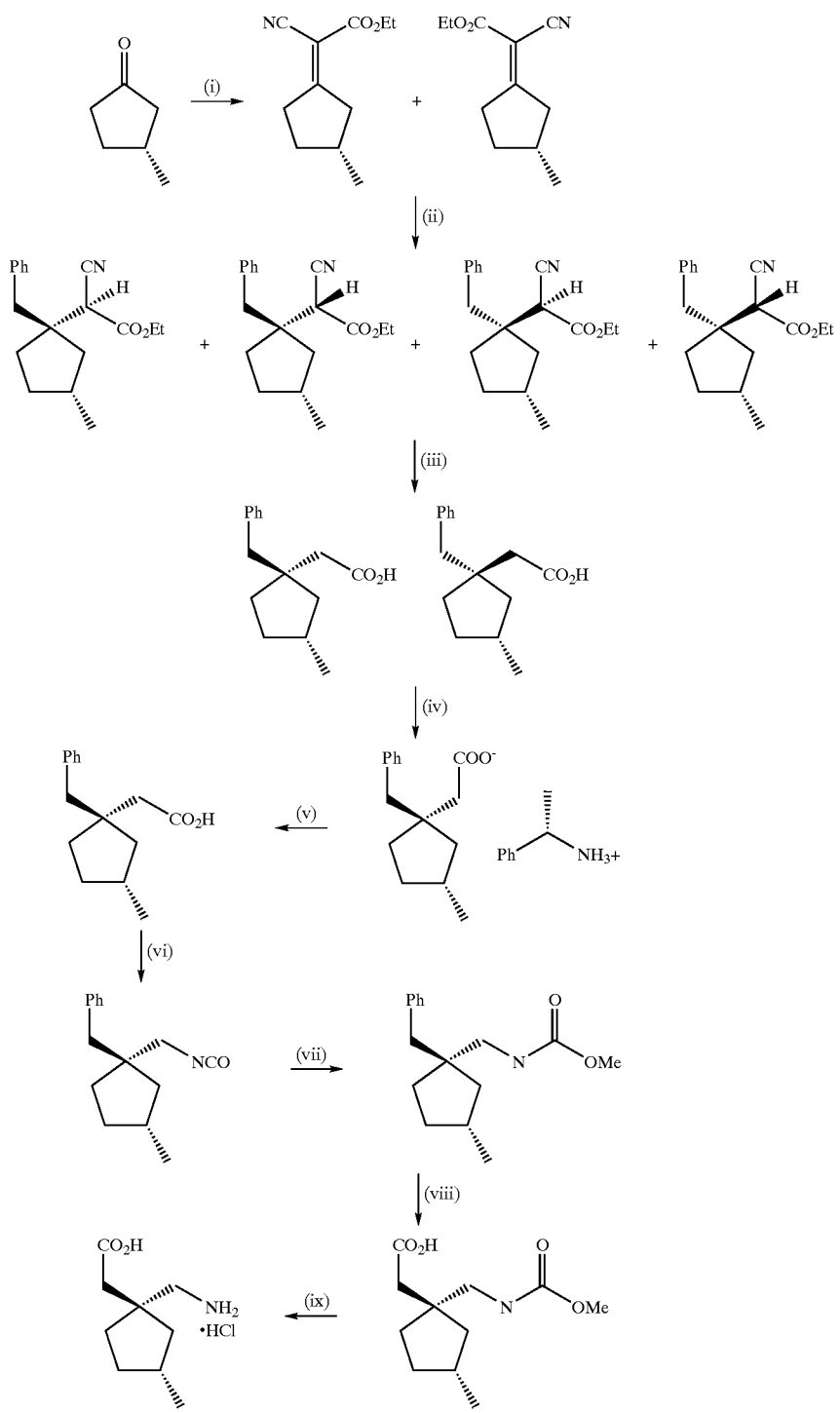
(i) NCCH$_2$CO$_2$Et, NH$_4$OAc, AcOH, toluene, reflux;
(ii) PhCH$_2$MgCl, THF, -78° C.;
(iii) KOH, ethylene glycol, 160° C.;
(iv) (S)-(-)-α-methyl benzylamine, EtOAc, 0° C.;
(v) HCl (aq);
(vi) (PhO)$_2$P(O)N$_3$, Et$_3$N, toluene, reflux;
(vii) MeOH, toluene, reflux;
(viii) RuCl$_3$, NaIO$_4$, CCl$_4$, MeCN, H$_2$O;
(ix) 6N HCl, 1,4-dioxane.

(E and Z)-Cyano-((R)-3-methyl-cyclopentylidene)-acetic acid ethyl ester (R)-(+)-3-Methylcyclopentanone (5 g, 51.0 mmol), ethyl cyanoacetate (5.42 mL, 51.0 mmol), ammonium acetate (0.4 g, 5.1 mmol), and glacial acetic acid (0.58 mL, 10.2 mmol) were refluxed in toluene (30 mL) using a Dean-Stark trap. After 6 hours, the mixture was allowed to cool and diluted with ethyl acetate (100 mL), washed with water (3×80 mL), brine, and dried (MgSO$_4$). The solvent was evaporated under reduced pressure. The residue was chromatographed (silica gel, heptane/ethyl acetate, 9:1) to give 8.87 g (90%) of a 1:1 mixture of (E and Z)-cyano-((R)-3-methyl-cyclopentylidene)-acetic acid ethyl ester;

$R_f$ (heptane-ethyl acetate, 9:1) 0.28;
IR thin film (cm$^{-1}$) 2225 (CN), 1724 (C=O), 1617 (C=C);
$^1$H-NMR (400 MHz; CDCl$_3$): δ 4.27 (2H, q, J 7.2, CO$_2$CH$_2$Me), 4.26 (2H, q, J 7.2, CO$_2$CH$_2$Me), 3.35 (1H, dt, J 7.1, 1.6), 3.30 (1H, dt, J 7.1, 1.6), 3.23 (1H, ddd, J 8.1, 3.5, 1.7), 3.18 (1H, ddd, J 8.1, 3.4, 1.7), 3.05–2.67 (4H, m), 2.50–2.32 (2H, m), 2.29–1.96 (4H, m), 1.50–1.35 (2H, m), 1.34 (3H, t, J 7.2, CO$_2$CH$_2$Me), 1.33 (3H, t, J 7.1, CO$_2$CH$_2$Me), 1.10 (3H, d, J 6.6, Me), 1.08 (3H, d, J 6.6, Me);
MS (ES$^-$): m/z 192 (M–H, 100%).

(R and S)-((1S,3R)-1-Benzyl-3-methyl-cyclopentyl)-cyano-acetic acid ethyl ester and (R and S)-((1R,3R)-1-Benzyl-3-methyl-cyclopentyl)-cyano-acetic acid ethyl ester A mixture of (E and Z)-cyano-((R)-3-methyl-cyclopentylidene)-acetic acid ethyl ester (4.13 g, 21.4 mmol) in THF (30 mL) was added over 1 hour to a stirring solution of benzylmagnesium chloride (27.7 mL of a 1 M solution in ether, 27.7 mmol) in THF (50 mL) at −78° C. under argon. After stirring for a further 1 hour, the mixture was quenched by addition of saturated ammonium chloride solution (15 mL). The mixture was allowed to warm to room temperature, diluted with ether (30 mL), and dilute hydrochloric acid (20 mL) was added. The organic layer was separated, and the aqueous layer was further extracted with ether (2×40 mL). The combined ether layers were washed with brine, dried (MgSO$_4$), and the solvent was evaporated under reduced pressure. The residue was chromatographed (silica gel, heptane-ethyl acetate, 95:5) to give 5.8 g (100%) of a 7:7:3:3 mixture of diastereomeric (R and S)-((1S,3R)-1-benzyl-3-methyl-cyclopentyl)-cyano-acetic acid ethyl ester and (R and S)-((1R,3R)-1-benzyl-3-methyl-cyclopentyl)-cyano-acetic acid ethyl ester;

$R_f$ (heptane-ethyl acetate, 9:1) 0.32;
IR thin film (cm$^{-1}$) 2246 (CN), 1740 (C=O), 1603 (C=C);
MS (ES$^-$) m/z 284 (M–H, 100%).

((1S,3R)-1-Benzyl-3-methyl-cyclopentyl)-acetic acid and ((1R,3R)-1-Benzyl-3-methyl-cyclopentyl)-acetic acid The mixture of (R and S)-((1S,3R)-1-benzyl-3-methyl-cyclopentyl)-cyano-acetic acid ethyl ester and (R and S)-((1R,3R)-1-benzyl-3-methyl-cyclopentyl)-cyano-acetic acid ethyl ester (1 g, 3.5 mmol) and potassium hydroxide (1.2 g, 21.4 mmol) were heated to 160° C. in ethylene glycol (5 mL) for 16 hours. After this time, the mixture was allowed to cool and dilute hydrochloric acid (150 mL) was added carefully. The mixture was extracted with ethyl acetate (3×50 mL), and the combined organic fractions were washed with brine, dried (MgSO$_4$), and the solvent was evaporated under reduced pressure. The residue was chromatographed (silica gel, heptane/ethyl acetate, 98:2) to give 0.65 g (80%) of a 7:3 mixture of ((1S,3R)-1-benzyl-3-methyl-cyclopentyl)-acetic acid and ((1R,3R)-1-benzyl-3-methyl-cyclopentyl)-acetic acid as an oil;

$R_f$ (heptane-ethyl acetate, 98:2) 0.36;
IR thin film (cm$^{-1}$) 1702 (C=O);
$^1$H-NMR (400 MHz; CDCl$_3$) major isomer ((1S,3R)-1-benzyl-3-methyl-cyclopentyl)-acetic acid: δ 7.31–7.21 (5H, m, Ph), 2.82 (1H, d, J 13.4, CH$_A$H$_B$CO$_2$H), 2.76 (1H, d, J 13.4, CH$_A$H$_B$CO$_2$H), 2.33 (2H, br s, CH$_2$Ph), 2.19–1.66 (m), 1.62–1.52 (m), 1.11 (1H, dd, J 13.0, 9.9), 1.01 (3H, d, J 6.6, Me); minor isomer ((1R,3R)-1-benzyl-3-methyl-cyclopentyl)-acetic acid: δ 7.31–7.21 (5H, m, Ph), 2.89 (1H, d, J 13.2, CH$_A$H$_B$CO$_2$H), 2.84 (1H, d, J 13.4, CH$_A$H$_B$CO$_2$H), 2.28 (2H, br s, CH$_2$Ph), 2.19–1.66 (m), 1.62–1.52 (m), 1.30–1.17 (m), 1.00 (3H, d, J 6.6, Me);
MS (CI$^-$): m/z 231 (M–H, 100%).

((1S,3R)-1-Benzyl-3-methyl-cyclopentyl)-acetic acid (s)-(–)-α-Methyl benzylamine (8.8 g, 72.7 mmol) was added to a stirring solution of the diastereomeric mixture of ((1S,3R)-1-benzyl-3-methyl-cyclopentyl)-acetic acid and ((1R,3R)-1-benzyl-3-methyl-cyclopentyl)-acetic acid (16.9 g, 72.7 mmol) dissolved in the minimum quantity of ethyl acetate. The mixture was placed in the fridge and left for 1 hour. After this time, the acid salt had crystallised out and this was filtered off. The salt was recrystallized several times from ethyl acetate (to 95% de). The salt was taken up in ethyl acetate, washed with dilute hydrochloric acid, brine and dried (MgSO$_4$). The solvent was evaporated under reduced pressure to give 6.8 g (40%) of ((1S,3R)-1-benzyl-3-methyl-cyclopentyl)-acetic acid; LCMS (Prodigy® (Phenomenex, Ltd.) ODS 3.50 mm×4.6 mm id column, 5–50% Acetonitrile/water) Retention Time=2.01 min, 98% purity.

((1S,3R)-1-Isocyanatomethyl-3-methyl-cyclopentylmethyl)-benzene

Diphenylphosphoryl azide (4.48 g, 16 mmol), triethylamine (1.69 g, 16.8 mmol), and acid ((1S,3R)-1-benzyl-3-methyl-cyclopentyl)-acetic acid (3.74 g, 16 mmol) were refluxed in toluene (40 mL) for 17 hours. The mixture was allowed to cool and then taken up in ethyl acetate (150 mL), washed with saturated aqueous sodium hydrogen carbonate (200 mL), brine (150 mL), and dried (MgSO$_4$). The solvent was removed under reduced pressure to give 3.69 g (100%) of ((1S,3R)-1-isocyanatomethyl-3-methyl-cyclopentylmethyl)-benzene, which was used without further purification;

$R_f$ (heptane-ethyl acetate, 8:2) 0.36;
IR thin film (cm$^{-1}$) 2262 (CN).

((1S,3R)-1-Benzyl-3-methyl-cyclopentylmethyl)-carbamic acid methyl ester ((1S,3R)-1-Isocyanatomethyl-3-methyl-cyclopentylmethyl)-benzene (3.69 g, 16 mmol) was refluxed in methanol (10 mL) and toluene (20 mL) for 16 hours and then allowed to cool to room temperature. The solvent was removed under reduced pressure, and the residue was purified by chromatography (silica gel, heptane-ethyl acetate 9:1) to give 2.66 g (63%) of((1S,3R)-1-benzyl-3-methyl-cyclopentylmethyl)-carbamic acid methyl ester;

$R_f$ (heptane-ethyl acetate, 8:2) 0.28;
IR thin film (cm$^{-1}$) 1709 (C=O);
$^1$H-NMR (400 MHz; CDCl$_3$) δ 7.32–7.16 (5H, m, Ph), 4.60 (1H, bs, NH), 3.68 (3H, s, OMe), 3.18–3.00 (2H, m, CH$_2$NH), 2.62–2.60 (2H, s, CH$_2$Ph), 0.99 (3H, d, J 6.8, Me), 2.05–1.92, 1.87–1.72, 1.60–1.40, 1.00–0.89 (7H, m);
MS (ES$^+$) m/z 262 (M+H, 90%), 302 (M+CH$_3$CN+H, 100%);
LCMS (Prodigy® ODS 3 50 mm×4.6 mm id column, 5–50% Acetonitrile (0.05% formic acid)/water (0.05% formic acid)) Retention Time=2.11, 94% de.

[(1S,3R)-1-(Methoxycarbonylamino-methyl)-3-methyl-cyclopentyl]-acetic acid ((1S,3R)-1-Benzyl-3-methyl-cyclopentylmethyl)-carbamic acid methyl ester (2.6 g, 9.9 mmol) and sodium periodate (29.8 g, 140 mmol) were stirred together in carbon tetrachloride (30 mL), acetonitrile (30 mL), and water for 6 hours. The mixture was cooled to 0° C., and ruthenium(III) chloride (0.04 g, 0.2 mmol) was added to the reaction mixture. The reaction was allowed to warm to room temperature and stirred for 20 hours. Diethyl ether (50 mL) was added, and the mixture was then extracted with saturated aqueous sodium hydrogen carbonate (200 mL). The aqueous layer was acidified to pH 1 with 4N hydrochloric acid and re-extracted with ethyl acetate (200 mL), dried (MgSO$_4$), MS (ES$^+$) m/z 173 (M+H, 100%), 196 (M+Na, 10%);

LCMS (Prodigy® ODS 3 50 mm×4.6 mm id column, 5% for 2 min, 5–50% over 1.5 min of Acetonitrile (0.05% formic acid)/water (0.05% formic acid)) Retention Time= 0.92, 94% de.

EXAMPLE 2

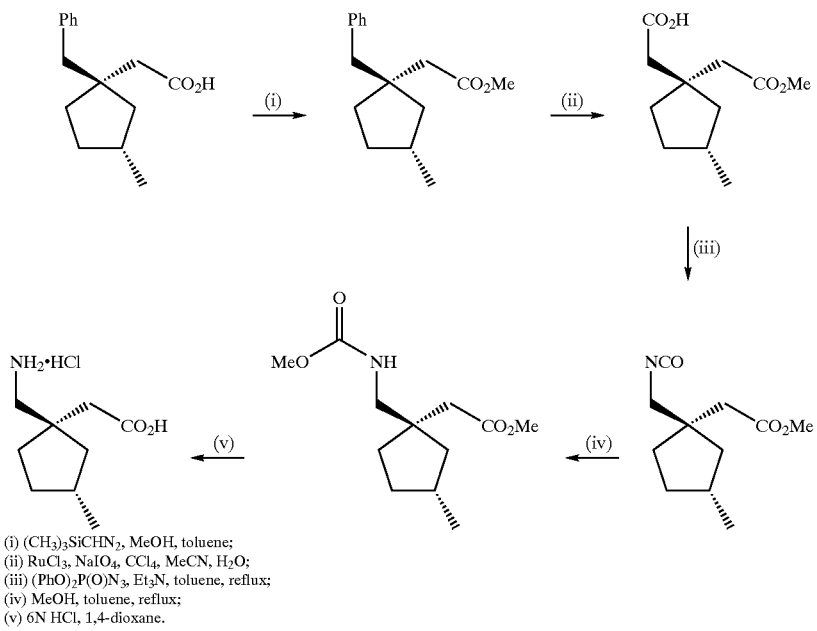

(i) (CH$_3$)$_3$SiCHN$_2$, MeOH, toluene;
(ii) RuCl$_3$, NaIO$_4$, CCl$_4$, MeCN, H$_2$O;
(iii) (PhO)$_2$P(O)N$_3$, Et$_3$N, toluene, reflux;
(iv) MeOH, toluene, reflux;
(v) 6N HCl, 1,4-dioxane.

and the solvent was evaporated under reduced pressure. The residue was purified by chromatography (silica gel, eluting with a gradient of heptane to 1:1 heptane:ethyl acetate) to give 0.32 g (14%) of [(1S,3R)-1-(methoxycarbonylamino-methyl)-3-methyl-cyclopentyl]-acetic acid;

R$_f$ (heptane-ethyl acetate, 8:2) 0.30;
IR thin film (cm$^{-1}$) 3338 (NH), 1712 (C=O);
$^1$H-NMR (400 MHz; CDCl$_3$): δ 9.29 (1H, s, COOH), 5.17 (1H, bs, NH), 3.71 (3H, s, OMe), 3.30 (1H, dd, J 14.4, 7.1, CH$_A$H$_B$NH$_2$), 3.17 (1H, dd, J 14.4, 6.6, CH$_A$H$_B$NH$_2$), 2.37 (2H, s, CH$_2$COOH), 2.20–1.00 (7H, m), 1.01 (3H, d, J 6.4, CHMe);
MS (ES$^+$) m/z 230 (M+H, 63%), 481 (M+Na, 100).
((1S,3R)-1-Aminomethyl-3-methyl-cyclopentyl)-acetic acid hydrochloride

[(1S,3R)-1-(Methoxycarbonylamino-methyl)-3-methyl-cyclopentyl]-acetic acid (0.32 g, 1.4 mmol) was refluxed in a mixture of 1,4-dioxane (3 mL) and 6N Hydrochloric acid (8 mL) for 4 hours. The mixture was allowed to cool, diluted with water (200 mL), and washed with dichloromethane (2×200 mL). The aqueous layer was evaporated under reduced pressure, and the residue was recrystallized from ethyl acetate/methanol to give 0.17 g (59%) of ((1S,3R)-1-aminomethyl-3-methyl-cyclopentyl)-acetic acid hydrochloride;

IR thin film (cm$^{-1}$) 1710 (C=O);
$^1$H-NMR (400 MHz; DMSO-d$_6$): δ 2.96 (1H, d, J 12.8, CH$_A$H$_B$NH2), 2.90 (1H, d, J 12.8, CH$_A$H$_B$NH2), 2.40 (2H, s, CH$_2$COOH), 2.04 (1H, m, CHMe), 1.81–1.61, 1.51–1.43, 1.21–1.11 (5H, m), 1.06 (1H, dd, J 12.8, 10.4), 0.97 (3H, d, J 6.35, Me);

((1S,3R)-1-Benzyl-3-methyl-cyclopentyl)-acetic acid methyl ester

Trimethylsilyldiazomethane (31.5 mL of a 2 M solution in hexanes, 63 mmol) was added dropwise to a stirring solution of ((1S,3R)-1-benzyl-3-methyl-cyclopentyl)-acetic acid (10 g, 43 mmol) in toluene (80 mL) and methanol (20 mL) at 0° C. under argon, and the mixture was allowed to warm to room temperature. The mixture was stirred for 1 hour, and then the solvent was evaporated under reduced pressure. The residue was taken up in ethyl acetate (50 mL), washed with saturated sodium hydrogen carbonate solution, dilute hydrochloric acid, dried (MgSO$_4$), and the solvent removed in vacuo to give 10.6 g (100%) of ((1S,3R)-1-benzyl-3-methyl-cyclopentyl)-acetic acid methyl ester;

R$_f$ (heptane-ethyl acetate, 9:1) 0.40;
IR thin film (cm$^{-1}$) 1736 (C=O);
$^1$H-NMR (400 MHz; CDCl$_3$): δ 7.30–7.18 (5H, m, Ph), 3.69 (3H, s, OMe), 2.78 (1H, d, J 13.4, CH$_A$H$_B$CO$_2$Me), 2.72 (1H, d, J 13.4, CH$_A$H$_B$CO$_2$Me), 2.28 (2H, s, CH$_2$Ph), 2.16–1.50 (5H, m), 1.30–1.03 (2H, m), 1.00 (3H, d, J 6.6 Me).

((1S,3R)-1-Methoxycarbonylmethyl-3-methyl-cyclopentyl)-acetic acid ((1S,3R)-1-Benzyl-3-methyl-cyclopentyl)-acetic acid methyl ester (10.5 g, 43 mmol) and sodium periodate (128.0 g, 598 mmol) were stirred together in carbon tetrachloride (120 mL), acetonitrile (120 mL), and water (210 mL) for 1 hour. The mixture was cooled to 10° C., and ruthenium(III) chloride (0.177 g, 0.86 mmol) was added to the reaction mixture. The reaction was allowed to warm to room temperature and stirred for 20 hours. Diethyl ether (100 mL)

was added, and the mixture was acidified to pH 1 with concentrated hydrochloric acid and then extracted with ether (2×200 mL). The organic layer was extracted with saturated aqueous sodium hydrogen carbonate (2×200 mL) which was then acidified to pH 1 with 4N hydrochloric acid and re-extracted with ethyl acetate, dried (MgSO$_4$), and concentrated in vacuo. The residue was purified by chromatography (silica gel, eluting with a gradient of heptane to 1:1 heptane:ethyl acetate) to give 8.02 g (87.7%) of((1S,3R)-1-methoxycarbonylmethyl-3-methyl-cyclopentyl)-acetic acid;

$R_f$ (heptane-ethyl acetate, 1:1) 0.46;

IR thin film (cm$^{-1}$) 3100 (OH), 1737 (C=O), 1705 (C=O);

$^1$H-NMR (400 MHz; CDCl$_3$): δ 3.68 (3H, s, OMe), 2.67–2.51 (4H, m), 2.06 (1H, m), 1.97–1.79 (2H, m), 1.76–1.59 (2H, m), 1.29–1.08 (2H, m), 1.01 (3H, d, J 6.6 Me);

MS (ES$^+$) m/z 215 (M+H), 278 (M+Na, 100), 451 (2M+Na, 80%).

((1R,3R)-1-Isocyanatomethyl-3-methyl-cyclopentyl)-acetic acid methyl ester

Diphenylphosphoryl azide (8.07 mL, 37.4 mmol), triethylamine (5.36 mL, 39 mmol), and ((1S,3R)-1-methoxycarbonylmethyl-3-methyl-cyclopentyl)-acetic acid (7.93 g, 37 mmol) were refluxed in toluene (80 mL) for 17 hours. The mixture was allowed to cool and then taken up in ethyl acetate (250 mL), washed with saturated aqueous sodium hydrogen carbonate (250 mL), brine (100 mL), and dried (MgSO$_4$). The solvent was removed under reduced pressure to give 7.82 g (100%) of ((1R,3R)-1-isocyanatomethyl-3-methyl-cyclopentyl)-acetic acid methyl ester which was used without further purification;

IR thin film (cm$^{-1}$) 2264 (CN), 1732 (C=O).

[(1R,3R)-1-(Methoxycarbonylamino-methyl)-3-methyl-cyclopentyl]-acetic acid methyl ester ((1R,3R)-1-Isocyanatomethyl-3-methyl-cyclopentyl)-acetic acid methyl ester (7.82 g, 37 mmol) was refluxed in methanol (30 mL) and toluene (80 mL) for 17 hours and then allowed to cool to room temperature. The solvent was removed under reduced pressure, and the residue was purified by chromatography (silica gel, heptane to heptane:ether 8:2) to give 2.60 g (29%) of [(1R,3R)-1-(methoxycarbonylamino-methyl)-3-methyl-cyclopentyl]-acetic acid methyl ester;

$R_f$ (heptane-ethyl acetate, 1: 1) 0.52;

IR thin film (cm$^{-1}$) 1728 (C=O), 1716 (C=O);

$^1$H-NMR (400 MHz; CDCl$_3$): δ 3.67 (6H, s, OMe, NHCO$_2$Me), 3.21 (1H, dd, J 7.08, 14.2, CH$_A$H$_B$NHCO$_2$Me), 3.11 (1H, dd, J 6.10, 13.9, CH$_A$H$_B$NHCO$_2$Me), 2.36 (2H, s, CH$_2$CO$_2$Me), 2.05 (1H, m, CHMe), 1.86–1.46 & 1.29–1.18 (5H, m), 0.99 (3H, d, J 6.59, Me).

((1R,3R)-1-Aminomethyl-3-methyl-cyclopentyl)-acetic acid hydrochloride

[(1R,3R)-1-(Methoxycarbonylamino-methyl)-3-methyl-cyclopentyl]-acetic acid methyl ester (2.60 g, 37 mmol) was refluxed in a mixture of 1,4-dioxane (15 mL) and 6N Hydrochloric acid (30 mL) for 16 hours. The mixture was allowed to cool, diluted with water (80 mL), and washed with dichloromethane (2×200 mL). The aqueous layer was evaporated under reduced pressure, and the residue was recrystallized from ethyl acetate/methanol (95:5) to give 0.55 g (25%) of ((1R,3R)-1-aminomethyl-3-methyl-cyclopentyl)-acetic acid hydrochloride;

IR thin film (cm$^{-1}$) 1724 (C=O);

$^1$H-NMR (400 MHz; DMSO-d$_6$): δ 2.92 (1H, d, J 12.9, CH$_A$H$_B$N), 2.87 (1H, d, J 12.9, CH$_A$H$_B$N), 2.45 (1H, d, J 15.9, CH$_A$H$_B$COOH), 2.40 (1H, d, J 15.9, CH$_A$H$_B$COOH), 1.95 (1H, m), 1.84–1.72 (2H, m), 1.60–1.48 (2H, m), 1.20 (1H, m), 1.04 (1H, m), 0.96 (3H, d, J 6.8, Me).

EXAMPLE 3

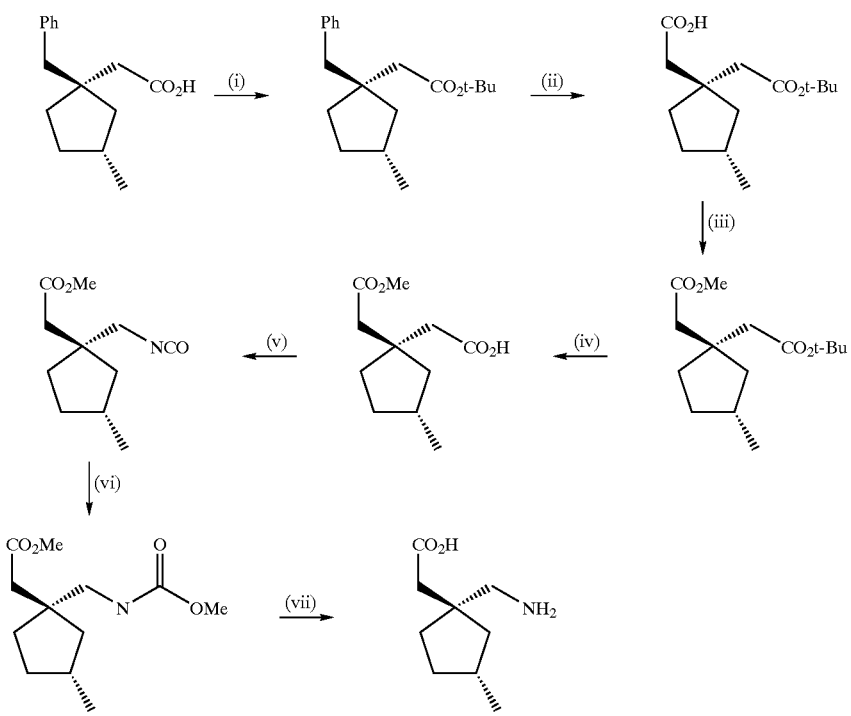

(i) a) oxalyl chloride, DMF, CH$_2$Cl$_2$;
    b) t-BuOH, (i-Pr)$_2$Net, CH$_2$Cl$_2$;
(ii) RuCl$_3$, NaIO$_4$, CCl$_4$, MeCN, H$_2$O;
(iii) (CH$_3$)$_3$SiCHN$_2$, MeOH, toluene;
(iv) CF$_3$CO$_2$H, CH$_2$Cl$_2$;
(v) (PhO)$_2$P(O)N$_3$, Et$_3$N, toluene, reflux;
(vi) MeOH, toluene, reflux;
(vii) 6N HCl, 1,4-dioxane.

((1S3R)-1-Benzyl-3-methyl-cyclopentyl)-acetic acid tert-butyl ester

Oxalyl chloride (4.14 mL, 47 mmol) was added dropwise to a stirring solution of ((1S,3R)-1-benzyl-3-methyl-cyclopentyl)-acetic acid (10 g, 43 mmol) in dichloromethane under argon at room temperature. The reaction mixture was cooled to 5° C., dimethylformamide (1 mL) was carefully added, and the mixture was allowed to warm to room temperature and stirred for a further 2 hours. The solvent was removed in vacuo and the residue diluted with dichloromethane (60 mL). 1,1-Dimethylethanol (15 mL) was carefully added to the reaction mixture under argon followed by diisopropylethylamine (11.5 mL, 65 mmol). The mixture was stirred for 17 hours and then taken up in ethyl acetate, washed with saturated aqueous sodium hydrogen carbonate (2×200 mL), and dried (MgSO$_4$). The solvent was removed under reduced pressure, and the residue was purified by chromatography (silica gel, eluting with a gradient of heptane to 9:1 heptane:ethyl acetate) to give 10.92 g (88%) of ((1S,3R)-1-benzyl-3-methyl-cyclopentyl)-acetic acid tert-butyl ester;

R$_f$ (heptane-ethyl acetate, 9:1) 0.64;
IR thin film (cm$^{-1}$) 1724 (C=O);
$^1$H-NMR (400 MHz;CDCl$_3$): δ 7.29–7.17 (5H, m, Ph), 2.77 (1H, d, J 13.6, CH$_A$H$_B$Ph), 2.71 (1H, d, J 13.6, CH$_A$H$_B$Ph), 2.18 (1H, s, CH$_A$H$_B$CO$_2$$^t$Butyl), 2.17 (1H, s,CH$_A$H$_B$CO$_2$$^t$Butyl), 1.49 (9H, s, CMe$_3$), 2.17–1.5 & 1.30–1.00 (7H, m), 1.00 (3H, d, J 6.8, CHMe).

[(1S,3R)-1-Carboxymethyl-3-methyl-cyclopentyl]-acetic acid tert-butyl ester ((1S,3R)-1-Benzyl-3-methyl-cyclopentyl)-acetic acid tert-butyl ester (10.72 g, 37.2 mmol) and sodium periodate (124.77 g, 0.583 mol) were stirred together in carbon tetrachloride (120 mL), acetonitrile (120 mL), and water (210 mL) for 2 hours. The mixture was cooled to 0° C., and ruthenium(III) chloride (0.173 g, 0.83 mmol) was added to the reaction mixture. The reaction was allowed to warm to room temperature and stirred for 48 hours. Diethyl ether (60 mL) was added, and the mixture was then acidified to pH 2 by the addition of dilute hydrochloric acid. The mixture was extracted with ethyl acetate (2×200 mL), dried (MgSO$_4$), and concentrated in vacuo. The residue was purified by chromatography (silica gel, eluting with a gradient of heptane to 1:1 heptane:ethyl acetate) to give 7.01 g (73.5%) of [(1S,3R)-1-carboxymethyl-3-methyl-cyclopentyl]-acetic acid tert-butyl ester;

R$_f$ (heptane-ethyl acetate, 1:1) 0.58;
IR thin film (cm$^{-1}$) 2953 (OH), 1726 (C=O) 1705 (C=O);
$^1$H-NMR (400 MHz; CDCl$_3$): δ 2.51 (2H, s, CH$_2$CO), 2.46 (2H, s, CH$_2$CO), 1.47 (9H, s, CMe$_3$), 2.05–2.15, 1.95–1.80, 1.75–1.60, 1.30–1.03 (7H, m), 1.01 (3H, d, J 6.4, Me).

[(1S ,3R)-1-Methoxycarbonylmethyl-3-methyl-cyclopentyl]-acetic acid tert-butyl ester Trimethylsilyldiazomethane (14 mL of a 2 M solution in hexanes, 26.9 mmol) was added dropwise to a stirring solution of [(1S,3R)-1-carboxymethyl-3-methyl-cyclopentyl]-acetic acid tert-butyl ester (6.9 g, 26.9 mmol) in toluene (60 mL) and methanol (15 mL) at 10° C. under argon, and the mixture was allowed to warm to room temperature. The mixture was stirred for 2 hours, and then the solvent was evaporated under reduced pressure. The residue was taken up in ethyl acetate (200 mL), washed with saturated sodium hydrogen carbonate solution, dilute hydrochloric acid, dried (MgSO$_4$), and the solvent removed in vacuo. The residue was purified by chromatography (silica gel, eluting with a gradient of heptane to 95:5 heptane:ethyl acetate) to give 6.73 g (92.4%) of [(1S,3R)-1-methoxycarbonylmethyl-3-methyl-cyclopentyl]-acetic acid tert-butyl ester;

R$_f$ (heptane-ethyl acetate, 9:1) 0.36;
IR thin film (cm$^{-1}$) 1738 (C=O) 1732 (C=O);
$^1$H-NMR (400 MHz; CDCl$_3$): δ 3.65 (3H, s, OMe), 2.52 (2H, m, CH$_2$CO$_2$), 2.45 (1H, d, J 4.8, CH$_2$CO$_2$), 1.44 (9H, s, CMe$_3$), 2.05–1.5, 1.30–1.10 (7H, m), 1.00 (3H, d, J 6.8, Me).

((1R,3R)-1-Methoxycarbonylmethyl-3-methyl-cyclopentyl)-acetic acid

[(1S,3R)-1-Methoxycarbonylmethyl-3-methyl-cyclopentyl]-acetic acid tert-butyl ester (6.64 g, 24.6 mmol) and trifluoroacetic acid (10 mL) were stirred together in dichloromethane (30 mL) for 17 hours at room temperature. The mixture was carefully poured into aqueous sodium carbonate and extracted with ethyl acetate (200 mL). The aqueous was acidified to pH 1 with concentrated hydrochloric acid and re-extracted with ethyl acetate (3×200 mL), dried (MgSO$_4$), and concentrated in vacuo. The residue was purified by chromatography (silica gel, eluting with a gradient of heptane to 1:1 heptane:ethyl acetate) to give 5.26 g (100%) of [(1R,3R)-1-methoxycarbonylmethyl-3-methyl-cyclopentyl]-acetic acid;

R$_f$ (heptane-ethyl acetate, 1:1) 0.46;
IR thin film (cm$^{-1}$) 2952 (OH), 1737 (C=O), 1706 (C=O);
$^1$H-NMR (400 MHz; CDCl$_3$): δ 3.68 (3H, s, OMe), 2.67 (1H, d, J 15.0, CH$_A$H$_B$CO$_2$), 2.61 (1H, d, J 14.9, CH$_A$H$_B$CO$_2$), 2.58 (1H, d, J 14.8, CH$_A$H$_B$CO$_2$), 2.53 (1H, d, J 14.8, CH$_A$H$_B$CO$_2$), 1.93–1.81, 1.75–1.59, 1.75–1.63 (6H, m), 1.16 (1H, dd, J 19.5, 9.3), 1.01 (3H, d, J 6.35, Me).

((1S,3R)-1-Isocyanatomethyl-3-methyl-cyclopentyl)-acetic acid methyl ester

Diphenylphosphoryl azide (5.35 mL, 24.8 mmol), triethylamine (3.55 mL, 25.6 mmol), and [(1R,3R)-1-methoxycarbonylmethyl-3-methyl-cyclopentyl]-acetic acid (5.26 g, 24.5 mmol) were refluxed in toluene (80 mL) for 17 hours. The mixture was allowed to cool and then taken up in ethyl acetate (300 mL), washed with saturated aqueous sodium hydrogen carbonate solution (250 mL), brine (200 mL), and dried (MgSO$_4$). The solvent was removed under reduced pressure to give 5.19 g (100%) of ((1S,3R)-1-isocyanatomethyl-3-methyl-cyclopentyl)-acetic acid methyl ester which was used without further purification;

IR thin film (cm$^{-1}$) 2262 (NCO), 1732 (C=O).

[(1S,3R)-1-(Methoxycarbonylamino-methyl)-3-methyl-cyclopentyl]-acetic acid methyl ester ((1S,3R)-1-Isocyanatomethyl-3-methyl-cyclopentyl)-acetic acid methyl ester (5.19 g, 24.5 mmol) was refluxed in methanol (30 mL) and toluene (80 mL) for 17 hours and then allowed to cool to room temperature. The solvent was removed under reduced pressure, and the residue was purified by chromatography (silica gel, heptane-ethyl acetate 9:1) to give 4.62 g (77%) of [(1S,3R)-1-(methoxycarbonylamino-methyl)-3-methyl-cyclopentyl]-acetic acid methyl ester;

$R_f$ (heptane-ethyl acetate, 1:1) 0.59;

IR thin film (cm$^{-1}$) 1730 (C=O);

$^1$H-NMR (400 MHz; CDCl$_3$): δ 3.68 (6H, s, OMe, NHCO$_2$Me), 3.27 (1H, dd, J 13.7, 6.8, CH$_A$H$_B$NHCO$_2$Me), 3.13 (1H, dd, J 13.9, 6.4, CH$_A$H$_B$NHCO$_2$Me), 2.37 (1H, d, J 13.9, CH$_A$H$_B$CO$_2$), 2.33 (1H, d, J 13.9, CH$_A$H$_B$CO$_2$), 2.09–1.99 (1H, m, CHMe), 1.88–1.76, 1.69–1.43, 1.28–1.19 (6H, m), 1.01 (3H, d, J 6.4, Me); m/z (CI$^+$) 244 (M+H, 100%).

((1S,3R)-1-Aminomethyl-3-methyl-cyclopentyl)-acetic acid hydrochloride

[(1S,3R)-1-(Methoxycarbonylamino-methyl)-3-methyl-cyclopentyl]-acetic acid methyl ester (2.84 g, 11.7 mmol) was refluxed in a mixture of 1,4-dioxane (15 mL) and 6N Hydrochloric acid (30 mL) for 17 hours. The mixture was allowed to cool, diluted with water (200 mL), and washed with dichloromethane (2×100 mL). The aqueous layer was evaporated under reduced pressure, and the residue was recrystallized from ethyl acetate/methanol (95:5) to give 1.28 g (53%) of ((1S,3R)-1-aminomethyl-3-methyl-cyclopentyl)-acetic acid hydrochloride;

IR thin film (cm$^{-1}$) 1710 (C=O);

$^1$H-NMR (400 MHz; DMSO-d$_6$): δ 2.96 (1H, d, J 12.8, CH$_A$H$_B$NH$_2$), 2.90 (1H, d, J 12.8, CH$_A$H$_B$NH$_2$), 2.40 (2H, s, CH$_2$COOH), 2.09–1.98 (1H, m, CHMe), 1.81–1.61, 1.51–1.43, 1.21–1.11 (5H, m), 1.04 (1H, dd, J 13.2, 10.4), 0.97 (3H, d, J 6.35, Me);

MS (ES$^+$) m/z 173 (M+H, 100%), 196 (M+Na, 10%);

LCMS (Prodigy® ODS 3 50 mm×4.6 mm id column, 5% for 2 min, 5–50% over 1.5 min of acetonitrile (0.05% formic acid)/water (0.05% formic acid)) Retention Time=0.92, 94% de; (Found: C, 49.5; H, 8.78; N, 6.37. C$_9$H$_{17}$NO$_2$1HCl0.6H$_2$O requires C, 49.5; H, 8.86; N, 6.41).

What is claimed is:

1. A process for the preparation of a compound of Formula I:

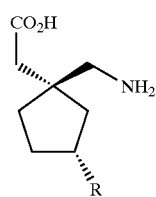

wherein R is C$_1$–C$_{10}$ alkyl or C$_3$–C$_{10}$ cycloalkyl, and pharmaceutically acceptable salts thereof, which comprises:

a) adding a cyanoacetate of formula (A):

wherein R$_1$ is alkyl or benzyl, to a mixture of a chiral cyclopentanone of formula (1):

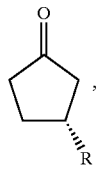

a solvent, a carboxylic acid, and a Knoevenagel reaction catalyst, and stirring the mixture in the presence of a means of removing water to produce the alkene of formula (2):

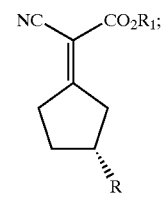

b) adding the product of Step a) above to a mixture of benzylmagnesium chloride, benzylmagnesium bromide, or benzylmagnesium iodide, in a solvent to produce the addition products of formulas (3a):

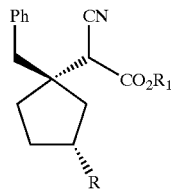

and (3b):

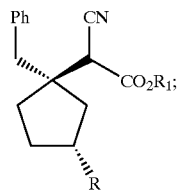

c) adding the products of Step b) above to a mixture of a base selected from potassium hydroxide, sodium hydroxide, lithium hydroxide, or cesium hydroxide in a solvent and stirring, and then acidifying to produce the carboxylic acids of formula (4a):

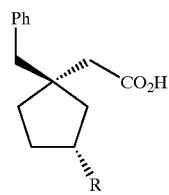

and (4b):

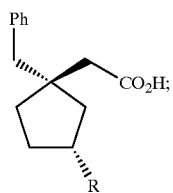

or adding the products of Step b) above to an acid mixture and stirring to produce the carboxylic acids of formulas (4a):

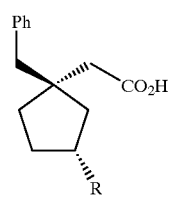

and (4b):

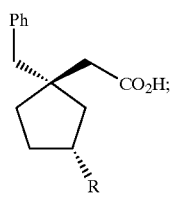

d) contacting the products of Step c) above with an amine in a solvent, and recrystallizing the salt so formed to produce the enriched diastereomer of formula (5):

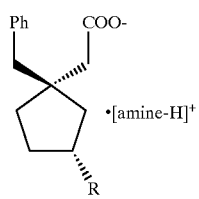

as the amine salt;

e) converting the product of Step d) to a carboxylic acid of formula (6):

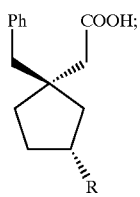

f) adding the product of Step e) to a mixture of iodomethane, a solvent, and a base, and stirring to produce the ester of formula (7):

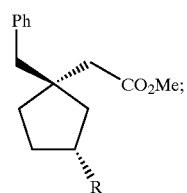

or adding the product of Step e) to methanol and an acid to produce the ester of formula (7):

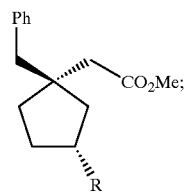

or adding the product of Step e) above to trimethylsilyldiazo-methane and methanol in a solvent to produce the ester of formula (7):

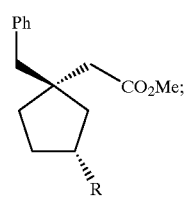

or adding the product of Step e) to a solution of diazomethane or trimethylsilyl-diazomethane in a solvent to produce ester of formula (7):

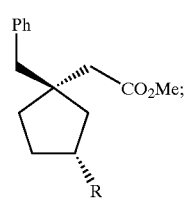

g) adding the product of Step f) to a mixture of carbon tetrachloride or ethyl acetate, and acetonitrile, water, sodium periodate, and ruthenium(III) chloride, and stirring to produce the carboxylic acid of formula (8):

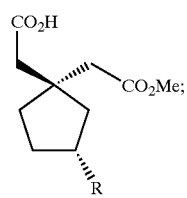

h) adding the product of Step g) to a mixture of a tertiary amine base, a solvent, and diphenylphosphoryl azide (DPPA), and stirring to produce the isocyanate of formula (9):

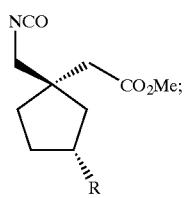

or adding the product of Step g) above to ethyl chloroformate or isobutyl chloroformate and a base in a solvent at a temperature of from −40° C. to 78° C., followed by adding a solution of sodium azide in water and tetrahydrofuran or acetone, followed by adding toluene or benzene, and refluxing to produce the isocyanate of formula (9):

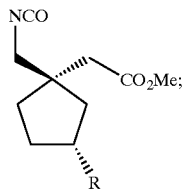

i) adding the product of Step h) to a mixture of a solvent and methanol, and stirring to produce the carbamate of formula (10):

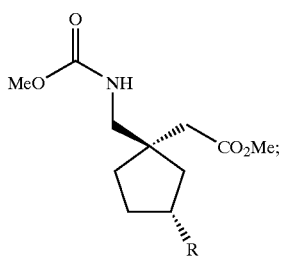

j) adding the product of Step i) to a mixture of a solvent and aqueous hydrochloric acid, and stirring to produce a compound of formula (Ia):

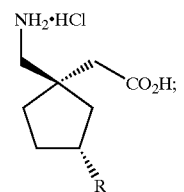

and k) converting the product of Step j) to a compound of formula (I):

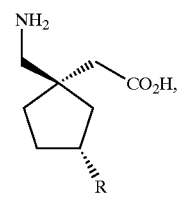

and further converting, if desired, to a pharmaceutically acceptable salt by known means.

2. A process according to claim 1 which comprises:

a) adding a cyanoacetate of formula (A):

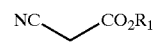

wherein $R_1$ is selected from methyl, ethyl, n-propyl, iso-propyl, n-butyl, iso-butyl, sec-butyl, tert-butyl, and benzyl to a mixture of a chiral cyclopentanone of formula (1):

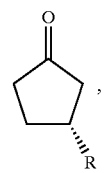

a solvent selected from tetrahydrofuran, 1,4-dioxane, tert-butylmethylether, chloroform, dichloromethane, acetonitrile, ethyl ether, ethyl acetate, hexanes, N,N-dimethylformamide, dimethylsulfoxide, ethanol, tert-butanol, toluene, benzene, xylenes, and n-heptane, acetic acid, and a Knoevenagel reaction catalyst selected from β-alanine, ammonium acetate, and piperidine, and stirring the mixture in the presence of a means of removing water selected from azeotropic distillation, activated molecular sieves, anhydrous magnesium sulfate, anhydrous sodium sulfate, anhydrous sodium carbonate, anhydrous potassium carbonate, anhydrous cesium carbonate, trimethyl orthoformate, and triethyl orthoformate to produce the alkene of formula (2):

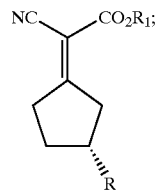

b) adding the product of Step a) above to a mixture of benzylmagnesium chloride, benzylmagnesium bromide, or benzylmagnesium iodide in a solvent selected from tetrahydrofuran, benzene, 1,4-dioxane, hexanes, n-heptane, toluene, diethyl ether, and tert-butyl methyl ether to produce the addition products of formulas (3a):

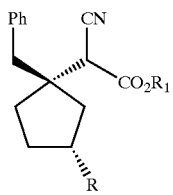

and (3b):

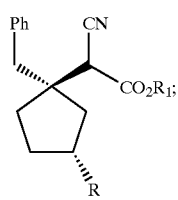

c) adding the products of Step b) above to a mixture of a base selected from potassium hydroxide, sodium hydroxide, lithium hydroxide, and cesium hydroxide in a solvent selected from ethylene glycol, 2-methoxyethyl ether, 1,4-dioxane, and diethylene glycol, and stirring the mixture, and then acidifying to produce the carboxylic acids of formulas (4a):

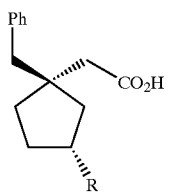

and (4b):

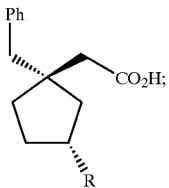

or adding the products of Step b) above to an acid mixture selected from 6–12 M HCl, 12 M $H_2SO_4$, 10%–48% wt/wt hydrobromic acid, and HBr in aqueous acetic acid, and stirring to produce the carboxylic acids of formulas (4a):

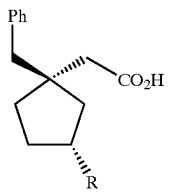

and (4b):

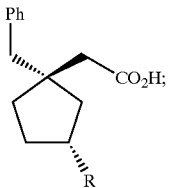

d) contacting the products of Step c) above with an amine selected from (S)-α-methyl-benzylamine, (R)-α-methyl-benzylamine, (R)-(+)-1-(naphthyl)ethylamine, (S)-(+)-1-(naphthyl)ethylamine, triethylamine, diisopropylethylamine, dicyclohexylamine, benzylamine, dibenzylamine, morpholine, N-methylmorpholine, piperidine, N-methylpiperidine, and pyridine in a solvent selected from N,N-dimethylformamide, chloroform, benzene, xylenes, hexanes, acetone, ethanol, methanol, iso-propanol, diethyl ether, dichloromethane, benzene, toluene, n-pentane, n-hexane, n-heptane, ethyl acetate, acetonitrile, tert-butyl methyl ether, tetrahydrofuran, and 1,4-dioxane, and recrystallizing the salt so formed to produce the enriched diastereomer of formula (5):

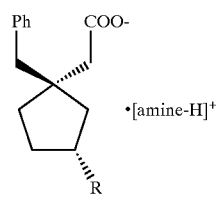

as the amine salt;

e) adding the product of Step d) to a mixture selected from aqueous hydrochloric acid, aqueous sulfuric acid, aqueous acetic acid, hydrochloric acid dissolved in acetic acid, or hydrochloric acid dissolved in acetic acid to which water is added and stirring to produce the carboxylic acid of formula (6):

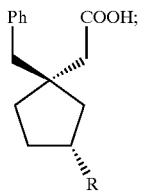

or partitioning the product of Step d) between a mixture of aqueous hydrochloric acid and a solvent selected from chloroform, dichloromethane, ethyl acetate, ethyl ether, tetrahydrofuran, 1,4-dioxane, toluene, and tert-butylmethylether, and drying and evaporating the organic layer to produce the carboxylic acid of formula (6):

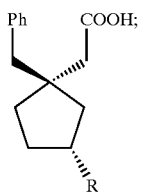

f) adding the product of Step e) above to a mixture of iodomethane, a solvent selected from dichloromethane, chloroform, tetrahydrofuran, toluene, and 1,4-dioxane, and a base selected from 1,8-diazabicyclo[5.4.0]undec-7-ene (DBU), diisopropylethylamine, triethylamine, and 1,5-diazabicyclo[4.3.0]non-5-ene (DBN), and stirring at a temperature of from −40° C. to 110° C. to produce the ester of formula (7):

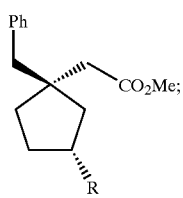

or adding the product of Step e) above to a mixture of methanol and concentrated sulphuric acid, concentrated hydrochloric acid, or hydrogen chloride at a temperature of from 0° C. to 100° C. to produce the ester of formula (7):

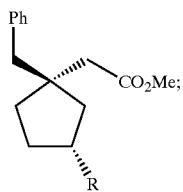

or adding the product of Step e) above to trimethylsilyldiazomethane and methanol in benzene or toluene at a temperature of from −40° C. to 100° C. to produce the ester of formula (7):

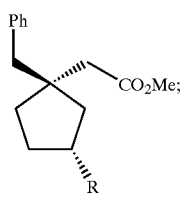

or adding the product of Step e) above to diazomethane or trimethylsilyldiazomethane in a solvent selected from benzene, toluene, dichloromethane, and diethyl ether at a temperature of from −40° C. to 40° C. to give a compound of formula (7):

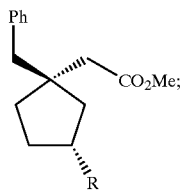

g) adding the product of Step f) to a mixture of carbon tetrachloride or ethyl acetate, and acetonitrile, water, sodium periodate, and ruthenium(III) chloride, and stirring at a temperature from −40° C. to 80° C. to produce the carboxylic acid of formula (8):

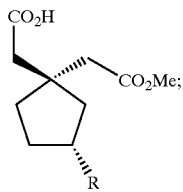

h) adding the product of Step g) above to a mixture of a base selected from triethylamine and diisopropylethylamine, a solvent selected from toluene, benzene, xylenes, tetrahydrofuran, diethyl ether and n-heptane, and diphenylphosphoryl azide (DPPA), and stirring at a temperature of from 0° C. to 150° C. to produce the isocyanate of formula (9):

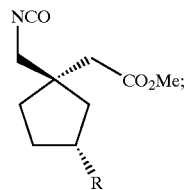

or adding the product of Step g) above to ethyl chloroformate or isobutyl chloroformate, a base selected from triethylamine and diisopropylethylamine, and a solvent selected from tetrahydrofuran, acetone, and diethyl ether at a temperature of from −40° C. to 78° C., followed by adding a solution of sodium azide in water and tetrahydrofuran or acetone, followed by adding toluene or benzene, and refluxing to produce the isocyanate of formula (9):

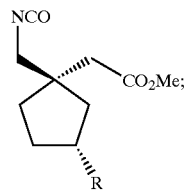

i) adding the product of Step h) to a mixture of a solvent selected from toluene, benzene, xylenes and n-heptane, and methanol, and stirring at a temperature from 0° C. to 150° C. to produce the carbamate of formula (10):

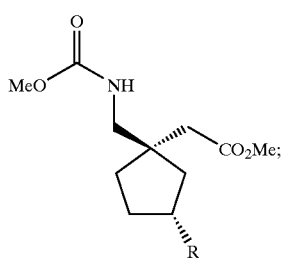

j) adding the product of Step i) to a mixture of a solvent selected from water, acetic acid, and 1,4-dioxane, and aqueous hydrochloric acid at a concentration of from 0.01 M to 12 M, and stirring at a temperature from 0° C. to 115° C. to produce a compound of formula Ia:

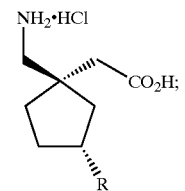

and k) converting the product of Step j) to a compound of formula I:

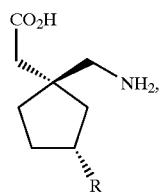

and further converting, if desired, to a pharmaceutically acceptable salt by known means.

3. A process according to claim 1 which comprises:

a) adding a cyanoacetate of formula (A):

wherein $R_1$ is ethyl, to a mixture of a chiral cyclopentanone of formula (1):

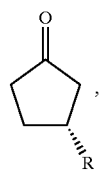

toluene, acetic acid, and a Knoevenagel reaction catalyst which is ammonium acetate, and heating the mixture at reflux over a Dean-Stark trap to produce the alkene of formula (2):

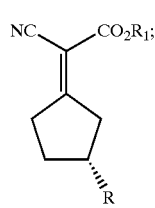

(2)

b) adding the product of Step a) above to a mixture of benzylmagnesium chloride in dry tetrahydrofuran at −100° C. to 25° C. to produce the addition products of formulas (3a):

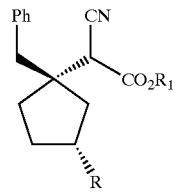

and (3b):

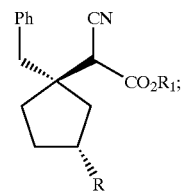

c) adding the products of Step b) above to a mixture of potassium hydroxide in ethylene glycol, and heating the mixture at 100° C. to 200° C., and then acidifying to produce the hydrolysis products of formulas (4a):

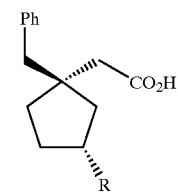

and (4b):

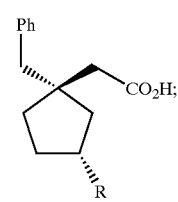

d) contacting the products of Step c) above with (S)-α-methyl-benzylamine in ethyl acetate, and recrystallizing the salt so formed from ethyl acetate to produce the enriched diastereomer of formula (5):

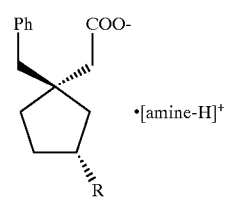

as the (S)-α-methyl-benzylamine salt;

e) adding the product of Step d) to aqueous hydrochloric acid and stirring to produce the carboxylic acid of formula (6):

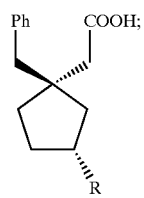

f) adding the product of Step e) to a mixture of iodomethane, dichloromethane, and 1,8-diazabicyclo [5.4.0]undec-7-ene (DBU), and stirring to produce the ester of formula (7):

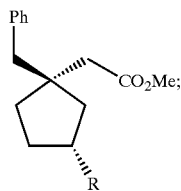

or adding the product of Step e) to methanol and concentrated sulfuric acid to produce the ester of formula (7):

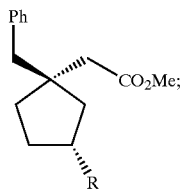

or adding the product of Step e) to a solution of diazomethane or trimethylsilyl-diazomethane in dichloromethane to produce the ester of formula (7):

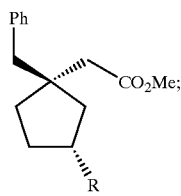

g) adding the product of Step f) to a mixture of carbon tetrachloride or ethyl acetate, and acetonitrile, water, sodium periodate, and ruthenium(III) chloride, and stirring to produce the carboxylic acid of formula (8):

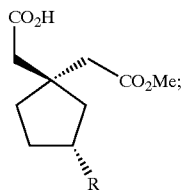

h) adding the product of Step g) to a mixture of triethylamine, toluene, and diphenylphosphoryl azide (DPPA), and refluxing to produce the isocyanate of formula (9):

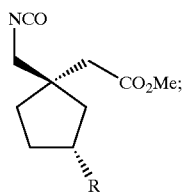

or adding the product of Step g) above to ethyl chloroformate or isobutyl chloroformate and triethylamine in tetrahydrofuran at a temperature of from −40° C. to 78° C., followed by adding a solution of sodium azide in water and tetrahydrofuran, followed by adding toluene or benzene, and refluxing to produce ester of formula (9):

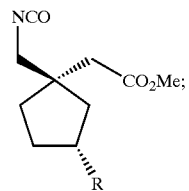

i) adding the product of Step h) to a mixture of methanol and toluene, and refluxing to produce the carbamate of formula (10):

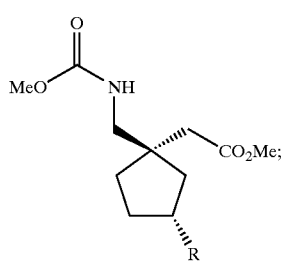

j) adding the product of Step i) to a mixture of 1,4-dioxane and aqueous hydrochloric acid at a concentration of 6 M, and stirring to produce a compound of formula Ia:

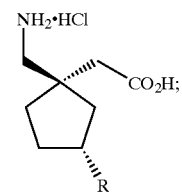

k) converting the product of Step j) to a compound of Formula I:

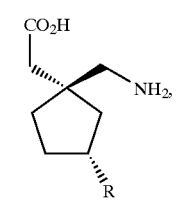

and further converting, if desired, to a pharmaceutically acceptable salt by known means.

4. A process according to claim 1, further characterized in that the intermediate product (9):

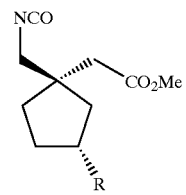

formed is reacted, without isolation, with methanol to produce the carbamate of formula (10):

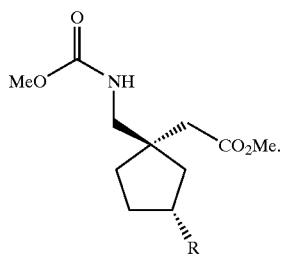

5. A process for the preparation of a compound of Formula II:

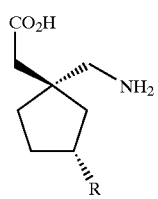

wherein R is $C_1$–$C_{10}$ alkyl or $C_3$–$C_{10}$ cycloalkyl, and pharmaceutically acceptable salts thereof, which comprises:

a) adding a cyanoacetate of formula (A):

wherein $R_1$ is alkyl or benzyl, to a mixture of a chiral cyclopentanone of formula (1):

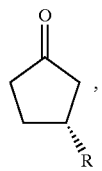

a solvent, a carboxylic acid, and a Knoevenagel reaction catalyst, and stirring the mixture in the presence of a means of removing water to produce the alkene of formula (2):

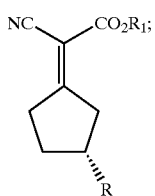

b) adding the product of Step a) above to a mixture of benzylmagnesium chloride, benzylmagnesium bromide, or benzylmagnesium iodide, in a solvent to produce the addition products of formulas (3a):

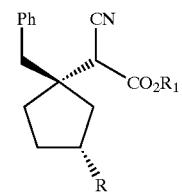

and (3b):

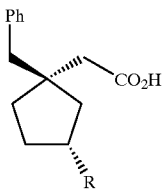

c) adding the products of Step b) above to a mixture of a base selected from potassium hydroxide, sodium hydroxide, lithium hydroxide, and cesium hydroxide and a solvent, and stirring, and then acidifying to produce the carboxylic acids of formulas (4a):

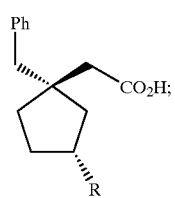

and (4b):

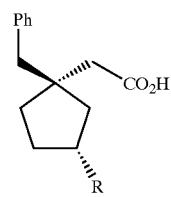

or adding the products of Step b) above to an acid mixture and stirring to produce the carboxylic acids of formulas (4a):

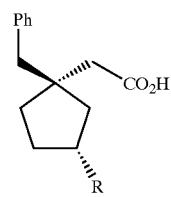

and (4b):

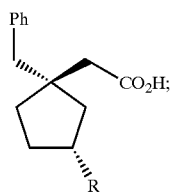

d) contacting the products of Step c) above with an amine in a solvent, and recrystallizing the salt so formed to produce the enriched diastereomer of formula (5):

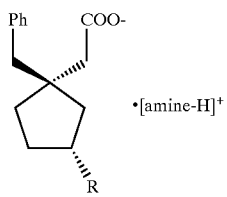

as the amine salt; and e) converting the product of Step d) to a carboxylic acid of formula (6):

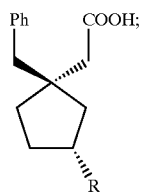

f) adding the product of Step e) to a mixture of a tertiary amine base, a solvent, and diphenylphosphoryl azide (DPPA), and stirring to produce the isocyanate of formula (11):

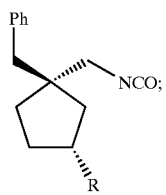

or adding the product of Step e) above to ethyl chloroformate or isobutyl chloroformate and a base in a solvent at a temperature of from −40° C. to 78° C., followed by adding a solution of sodium azide in water and tetrahydrofuran or acetone, followed by adding toluene or benzene, and refluxing to produce isocyanate of formula (11):

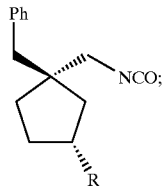

g) adding the product of Step f) to a mixture of a solvent and methanol, and stirring to produce the carbamate of formula (12):

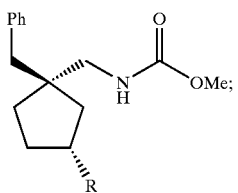

h) adding the product of Step g) to a mixture of carbon tetrachloride or ethyl acetate, and acetonitrile, water, sodium periodate, and ruthenium(III) chloride, and stirring to produce the carboxylic acid of formula (13):

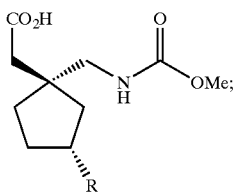

i) adding the product of Step h) to a mixture of a solvent and aqueous hydrochloric acid, and stirring to produce a compound of formula (IIa):

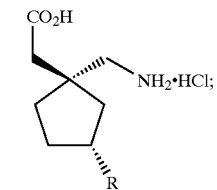

j) converting the product of Step i) to a compound of formula (II):

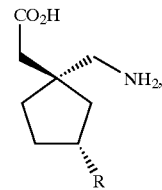

and further converting, if desired, to a pharmaceutically acceptable salt by known means.

6. A process according to claim 5 which comprises:

a) adding a cyanoacetate of formula (A):

wherein $R_1$ is selected from methyl, ethyl, n-propyl, iso-propyl, n-butyl, iso-butyl, sec-butyl, tert-butyl, and benzyl to a mixture of a chiral cyclopentanone of formula (1):

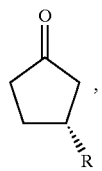

a solvent selected from tetrahydrofuran, 1,4-dioxane, tert-butylmethylether, chloroform, dichloromethane, acetonitrile, ethyl ether, ethyl acetate, hexanes, N,N-dimethylformamide, dimethylsulfoxide, ethanol, tert-butanol, toluene, benzene, xylenes, and n-heptane, acetic acid, and a Knoevenagel reaction catalyst selected from β-alanine, ammonium acetate, and piperidine, and stirring the mixture in the presence of a means of removing water selected from azeotropic distillation, activated molecular sieves, anhydrous magnesium sulfate, anhydrous sodium sulfate, anhydrous sodium carbonate, anhydrous potassium carbonate, anhydrous cesium carbonate, trimethyl orthoformate, and triethyl orthoformate to produce the alkene of formula (2):

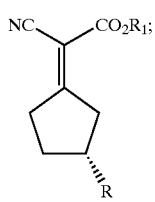

(2)

b) adding the product of Step a) above to a mixture of benzylmagnesium chloride, benzylmagnesium bromide, or benzylmagnesium iodide in a solvent selected from tetrahydrofuran, benzene, 1,4-dioxane, hexanes, n-heptane, toluene, diethyl ether, and tert-butyl methyl ether to produce the addition products of formulas (3a):

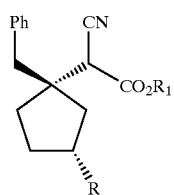

and (3b):

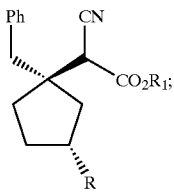

c) adding the products of Step b) above to a mixture of a base selected from potassium hydroxide, sodium hydroxide, lithium hydroxide, and cesium hydroxide in a solvent selected from ethylene glycol, 2-methoxyethyl ether, 1,4-dioxane, and diethylene glycol, and stirring the mixture and then acidifying to produce the carboxylic acids of formulas (4a):

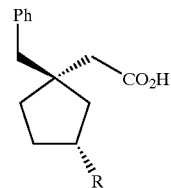

and (4b):

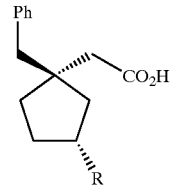

or adding the products of Step b) above to an acid mixture selected from 6–12 M HCl, 12 M H$_2$SO$_4$, 10%–48% wt/wt hydrobromic acid, and HBr in aqueous acetic acid, and stirring to produce the carboxylic acids of formulas (4a):

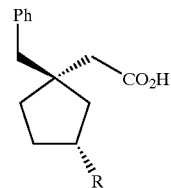

and (4b):

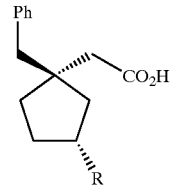

d) contacting the products of Step c) above with an amine selected from (S)-α-methyl-benzylamine, (R)-α-methyl-benzylamine, (R)-(+)-1-(naphthyl)ethylamine, (S)-(+)-1-(naphthyl)ethylamine, triethylamine, diisopropylethylamine, dicyclohexylamine, benzylamine, dibenzylamine, morpholine, N-methylmorpholine, piperidine, N-methylpiperidine, and pyridine in a solvent selected from N,N-dimethylformamide, chloroform, benzene, xylenes, hexanes, acetone, ethanol, methanol, iso-propanol, diethyl ether, dichloromethane, benzene, toluene, n-pentane, n-hexane, n-heptane, ethyl acetate, acetonitrile, tert-butyl methyl ether, tetrahydrofuran, and 1,4-dioxane, and recrystallizing the salt so formed to produce the enriched diastereomer of formula (5):

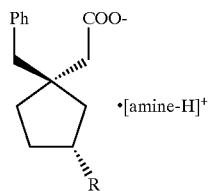

as the amine salt;

e) adding the product of Step d) to a mixture selected from aqueous hydrochloric acid, aqueous sulfuric acid, aqueous acetic acid, hydrochloric acid dissolved in acetic acid, and hydrochloric acid dissolved in acetic acid and water, and stirring to produce the carboxylic acid of formula (6):

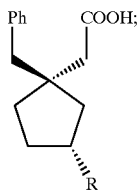

or partitioning the product of Step d) between a mixture of aqueous hydrochloric acid and a solvent selected from chloroform, dichloromethane, ethyl acetate, ethyl ether, tetrahydrofuran, 1,4-dioxane, toluene, and tert-butylmethylether, and drying and evaporating the organic layer to produce the carboxylic acid of formula (6):

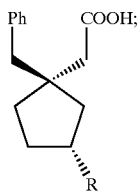

f) adding the product of Step e) above to a mixture of a base selected from triethylamine and diisopropylethylamine, a solvent selected from toluene, benzene, xylenes, tetrahydrofuran, diethyl ether and n-heptane, and diphenylphosphoryl azide (DPPA), and stirring at a temperature of from 0° C. to 150° C. to produce the isocyanate of formula (11):

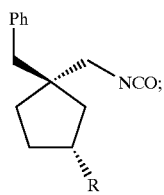

or adding the product of Step e) above to ethyl chloroformate or isobutyl chloroformate and a base selected from triethylamine and diisopropylethylamine, and a solvent selected from tetrahydrofuran, acetone, and diethyl ether at a temperature of from −40° C. to 78° C., followed by adding a solution of sodium azide in water and tetrahydrofuran or acetone, followed by adding toluene or benzene, and refluxing to produce the isocyanate of formula (11):

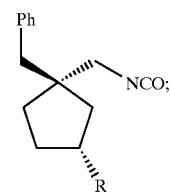

g) adding the product of Step f) to a solvent selected from toluene, benzene, xylenes, and n-heptane, and methanol, and stirring at a temperature from 0° C. to 150° C. to produce the carbamate of formula (12):

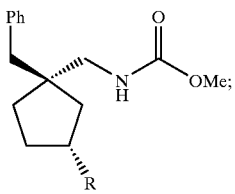

h) adding the product of Step g) to a mixture of carbon tetrachloride or ethyl acetate, and acetonitrile, water, sodium periodate, and ruthenium(III) chloride, and stirring at a temperature from −40° C. to 80° C. to produce the carboxylic acid of formula (13):

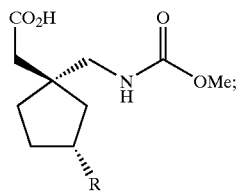

i) adding the product of Step h) to a mixture of a solvent selected from water, acetic acid, and 1,4-dioxane, and aqueous hydrochloric acid at a concentration of from 0.01 M to 12 M, and stirring at a temperature from 0° C. to 115° C. to produce a compound of formula IIa:

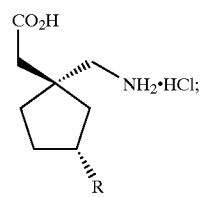

and j) converting the product of Step i) to a compound of Formula II:

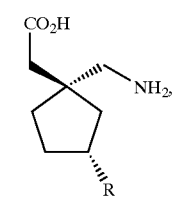

and further converting, if desired, to a pharmaceutically acceptable salt by known means.

7. A process according to claim 5 which comprises:

a) adding a cyanoacetate of formula (A):

wherein $R_1$ is ethyl, to a mixture of a chiral cyclopentanone of formula (1):

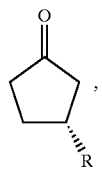

toluene, acetic acid, and a Knoevenagel reaction catalyst which is ammonium acetate, and heating the mixture at reflux over a Dean-Stark trap to produce the alkene of formula (2):

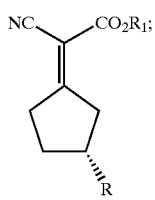

b) adding the product of Step a) above to a mixture of benzylmagnesium chloride in dry tetrahydrofuran at −100° C. to 25° C. to produce the addition products of formulas (3a):

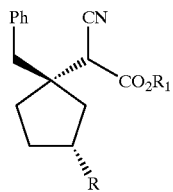

and (3b):

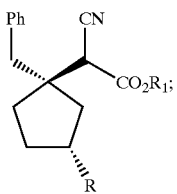

c) adding the products of Step b) above to a mixture of potassium hydroxide in ethylene glycol, and heating the mixture at 100° C. to 200° C., and then acidifying to produce the hydrolysis products of formulas (4a):

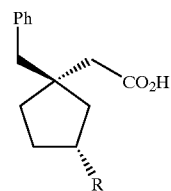

and (4b):

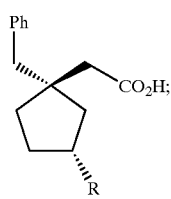

d) contacting the products of Step c) above with (S)-α-methyl-benzylamine in ethyl acetate, and recrystallizing the salt so formed from ethyl acetate to produce the enriched diastereomer of formula (5):

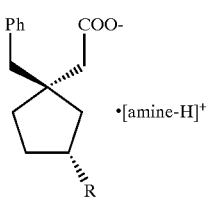

as the (S)-α-methyl-benzylamine salt;

e) adding the product of Step d) to aqueous hydrochloric acid and stirring to produce the carboxylic acid of formula (6):

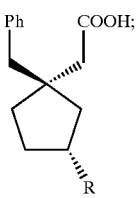

f) adding the product of Step e) to a mixture of triethylamine, toluene, and diphenylphosphoryl azide (DPPA), and refluxing to produce the isocyanate of formula (11):

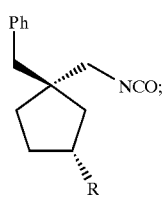

or adding the product of Step e) above to ethyl chloroformate or isobutyl chloroformate and triethylamine in tetrahydrofuran at a temperature of from −40° C. to 78° C., followed by adding a solution of sodium azide in water and tetrahydrofuran or acetone, followed by adding toluene or benzene, and refluxing to produce isocyanate of formula (11):

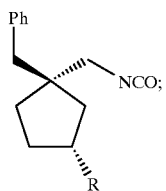

g) adding the product of Step f) to a mixture of methanol and toluene, and refluxing to produce the carbamate of formula (12):

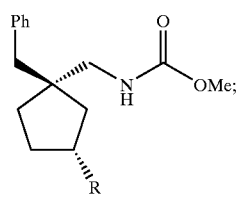

h) adding the product of Step g) to a mixture of carbon tetrachloride or ethyl acetate, and acetonitrile, water, sodium periodate, and ruthenium(III) chloride, and stirring to produce the carboxylic acid of formula (13):

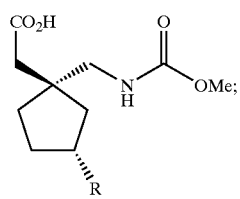

i) adding the product of Step h) to a mixture of 1,4-dioxane and aqueous hydrochloric acid at a concentration of 6 M, and stirring to produce a compound of formula IIa:

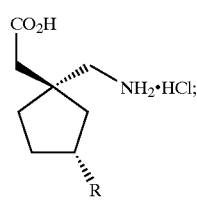

j) converting the product of Step i) to a compound of Formula II:

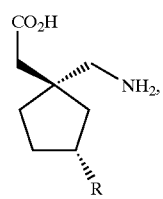

and further converting, if desired, to a pharmaceutically acceptable salt by known means.

8. A process according to claim 5, further characterized in that the intermediate product (11):

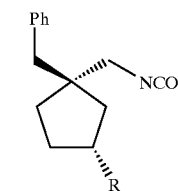

formed is further reacted, without isolation, with methanol to produce the carbamate of formula (12):

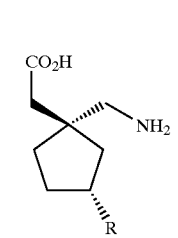

9. A process for the preparation of a compound of Formula II:

II wherein R is $C_1$–$C_{10}$ alkyl or $C_3$–$C_{10}$ cycloalkyl, and pharmaceutically acceptable salts thereof, which comprises:

a) adding a cyanoacetate of formula (A):

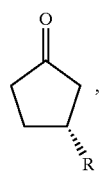

wherein $R_1$ is alkyl or benzyl, to a mixture of a chiral cyclopentanone of formula (1):

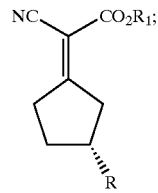

a solvent, a carboxylic acid, and a Knoevenagel reaction catalyst, and stirring the mixture in the presence of a means of removing water to produce the alkene of formula (2):

NC CO₂R₁;

b) adding the product of Step a) above to a mixture of benzylmagnesium chloride, benzylmagnesium bromide, or benzylmagnesium iodide, in a solvent to produce the addition products of formulas (3a):

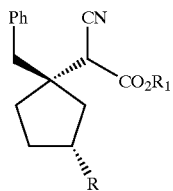

and (3b):

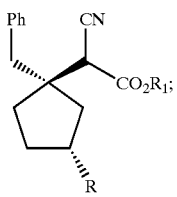

c) adding the products of Step b) above to a mixture of a base selected from potassium hydroxide, sodium hydroxide, lithium hydroxide, and cesium hydroxide, in a solvent, and stirring, and then acidifying to produce the carboxylic acids of formulas (4a):

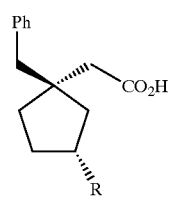

and (4b):

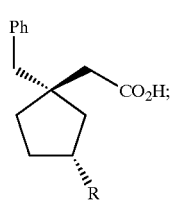

or adding the products of Step b) above to an acid mixture and stirring to produce the carboxylic acids of formulas (4a):

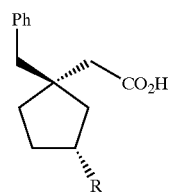

and (4b):

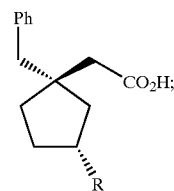

d) contacting the products of Step c) above with an amine in a solvent, and recrystallizing the salt so formed to produce the enriched diastereomer of formula (5):

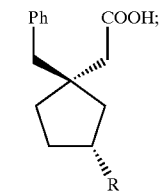

as the amine salt;

e) converting the product of Step d) to a carboxylic acid of formula (6):

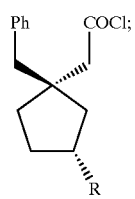

f) adding oxalyl chloride to a mixture of the product of Step e), a solvent, and N,N-dimethylformamide (DMF), and stirring to produce the acid chloride of formula (14):

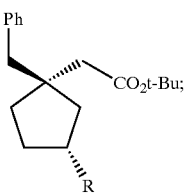

g) adding the product of Step f) to a mixture of tert-butyl alcohol, a solvent, and a tertiary amine base, and stirring to produce the ester of formula (15):

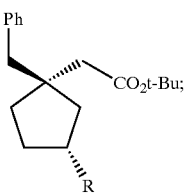

h) adding the product of Step g) to a mixture of carbon tetrachloride or ethyl acetate, and acetonitrile, water, sodium periodate, and ruthenium(III) chloride, and stirring to produce the carboxylic acid of formula (16):

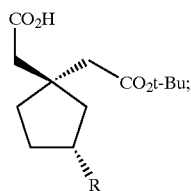

i) adding the product of Step h) to a mixture of a solvent, methanol, and (trimethylsilyl)diazomethane, and stirring to produce the bis ester of formula (17):

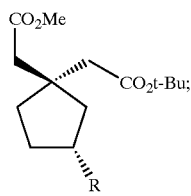

or adding the product of Step h) to a mixture of iodomethane, a solvent, and a base, and stirring to produce the bis ester of formula (17):

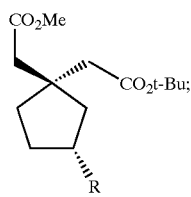

j) adding an acid to a mixture of the product from Step i) and a solvent, and stirring to produce the carboxylic acid of formula (18):

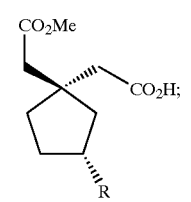

k) adding the product of Step j) to a mixture of a tertiary amine base, a solvent, and diphenylphosphoryl azide (DPPA) is added, and stirring to produce the isocyanate of formula (19):

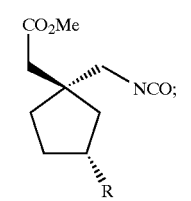

or adding the product of Step j) above to ethyl chloroformate or isobutyl chloroformate and a base in a solvent at a temperature of from −40° C. to 78° C., followed by adding a solution of sodium azide in water and tetrahydrofuran or acetone, followed by adding toluene or benzene and refluxing to produce isocyanate of formula (19):

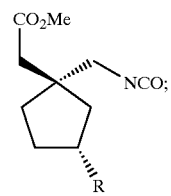

l) adding the product of Step k) to a mixture of a solvent and methanol, and stirring to produce the carbamate of formula (20):

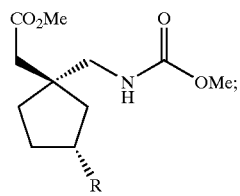

m) adding the product of Step l) to a mixture of a solvent and aqueous hydrochloric acid is added, and stirring to produce a compound of formula (IIa):

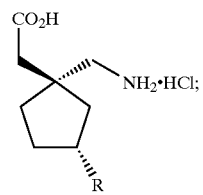

n) converting the product of Step m) to a compound of formula (II):

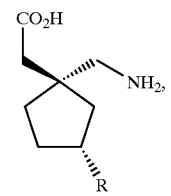

and further converting, if desired, to a pharmaceutically acceptable salt by known means.

10. A process according to claim 9 which comprises:

a) adding a cyanoacetate of formula (A)

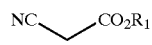

wherein $R_1$ is selected from methyl, ethyl, n-propyl, iso-propyl, n-butyl, iso-butyl, sec-butyl, tert-butyl, and benzyl to a mixture of a chiral cyclopentanone of formula (1):

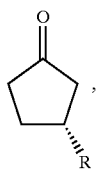

a solvent selected from tetrahydrofuran, 1,4-dioxane, tert-butylmethylether, chloroform, dichloromethane, acetonitrile, ethyl ether, ethyl acetate, hexanes, N,N-dimethylformamide, dimethylsulfoxide, ethanol, tert-butanol, toluene, benzene, xylenes, and n-heptane, acetic acid, and a Knoevenagel reaction catalyst selected from β-alanine, ammonium acetate, and piperidine, and stirring the mixture in the presence of a means of removing water selected from azeotropic distillation, activated molecular sieves, anhydrous magnesium sulfate, anhydrous sodium sulfate, anhydrous sodium carbonate, anhydrous potassium carbonate, anhydrous cesium carbonate, trimethyl orthoformate, and triethyl orthoformate to produce the alkene of formula (2):

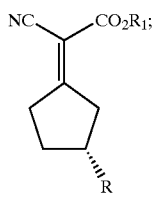

b) adding the product of Step a) above to a mixture of benzylmagnesium chloride, benzylmagnesium bromide, or benzylmagnesium iodide in a solvent selected from tetrahydrofuran, benzene, 1,4-dioxane, hexanes, n-heptane, toluene, diethyl ether, and tert-butyl methyl ether to produce the addition products of formulas (3a):

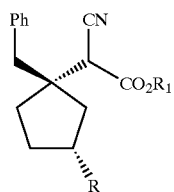

and (3b):

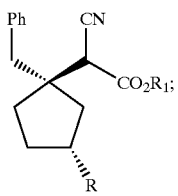

c) adding the products of Step b) above to a mixture of a base selected from potassium hydroxide, sodium hydroxide, lithium hydroxide, and cesium hydroxide in a solvent selected from ethylene glycol, 2-methoxyethyl ether, 1,4-dioxane, and diethylene glycol, and stirring the mixture and then acidifying to produce the carboxylic acids of formulas (4a):

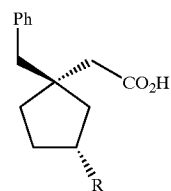

and (4b):

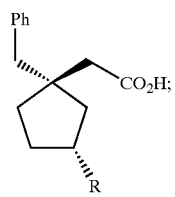

or adding the products of Step b) above to an acid mixture selected from 6–12 M HCl, 12 M $H_2SO_4$, 10%–48% wt/wt hydrobromic acid, and HBr in aqueous acetic acid, and stirring to produce the carboxylic acids of formulas (4a):

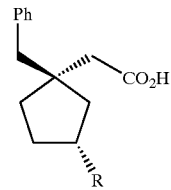

and (4b):

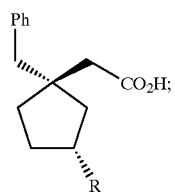

d) contacting the products of Step c) above with an amine selected from (S)-α-methyl-benzylamine, (R)-α-methyl-benzylamine, (R)-(+)-1-(naphthyl)ethylamine, (S)-(+)-1-(naphthyl)ethylamine, triethylamine, diisopropylethylamine, dicyclohexylamine, benzylamine, dibenzylamine, morpholine, N-methylmorpholine, piperidine, N-methylpiperidine, and pyridine in a solvent selected from N,N-dimethylformamide, chloroform, benzene, xylenes, hexanes, acetone, ethanol, methanol, iso-propanol, diethyl ether, dichloromethane, benzene, toluene, n-pentane, n-hexane, n-heptane, ethyl acetate, acetonitrile, tert-butyl methyl ether, tetrahydrofuran, and 1,4-dioxane, and recrystallizing the salt so formed to produce the enriched diastereomer of formula (5):

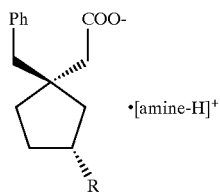

as the amine salt;

e) adding the product of Step d) to a mixture selected from aqueous hydrochloric acid, aqueous sulfuric acid, aqueous acetic acid, hydrochloric acid dissolved in acetic acid, or hydrochloric acid dissolved in acetic acid and water, and stirring to produce the carboxylic acid of formula (6):

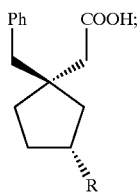

or partitioning the product of Step d) between a mixture of aqueous hydrochloric acid and a solvent selected from chloroform, dichloromethane, ethyl acetate, ethyl ether, tetrahydrofuran, 1,4-dioxane, toluene, and tert-butylmethylether, and drying and evaporating the organic layer to produce the carboxylic acid of formula (6):

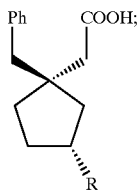

f) adding oxalyl chloride to a mixture of the product of Step e), a solvent selected from dichloromethane, chloroform, ethyl ether, toluene, and tert-butyl methyl ether, and 0.01 to 10 mole percent of N,N-dimethylformamide (DMF), and stirring at a temperature from −40° C. to 110° C. to produce the acid chloride of formula (14):

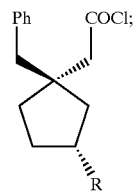

g) adding the product of Step f) to a mixture of tert-butyl alcohol, a solvent selected from dichloromethane, chloroform, ethyl ether, toluene, and tert-butyl methyl ether, and N,N-diisopropylethylamine (DIPEA) or triethylamine, and stirring at a temperature from −40° C. to 110° C. to produce the ester of formula (15):

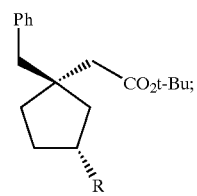

h) adding the product of Step g) to a mixture of carbon tetrachloride or ethyl acetate, and acetonitrile, water, sodium periodate, and ruthenium(III) chloride, and stirring at a temperature from −40° C. to 80° C. to produce the carboxylic acid of formula (16):

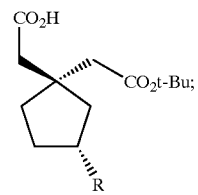

i) adding the product of Step h) to a solvent selected from toluene, benzene, xylenes, and n-heptane, methanol, and (trimethylsilyl)diazomethane, and stirring at a temperature from 0° C. to 150° C. to produce the bis ester of formula (17):

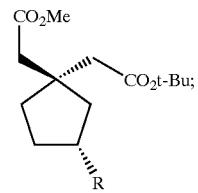

or adding the product of Step h) to a mixture of iodomethane, a solvent selected from dichloromethane, chloroform, tetrahydrofuran, toluene and 1,4-dioxane, and a base selected from 1,8-diazabicyclo[5.4.0]undec-7-ene (DBU), diisopropylethylamine, triethylamine, or 1,5-diazabicyclo[4.3.0]non-5-ene (DBN), and stirring at a temperature of from −40° C. to 110° C. to produce the bis ester of formula (17):

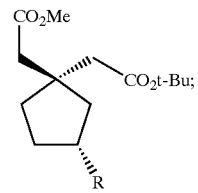

j) adding hydrochloric acid or trifluoroacetic acid (TFA) to a mixture of the product from Step i) and a solvent selected from dichloromethane, chloroform, 1,4-dioxane, tetrahydrofuran, ethyl ether, and tert-butyl methyl ether, and stirring at a temperature from −40° C. to 110° C. to produce the carboxylic acid of formula (18):

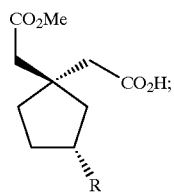

k) adding the product of Step j) to a mixture of a base selected from triethylamine and diisopropylethylamine, a solvent selected from toluene, benzene, xylenes, and n-heptane, and diphenylphosphoryl azide (DPPA), and stirring at a temperature from 0° C. to 150° C. to produce the isocyanate of formula (19):

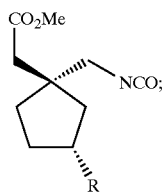

or adding the product of Step j) above to ethyl chloroformate or isobutyl chloroformate, a base selected from triethylamine and diisopropylethylamine, and a solvent selected from tetrahydrofuran, acetone, and diethyl ether at a temperature of from −40° C. to 78° C., followed by adding a solution of sodium azide in water and tetrahydrofuran or acetone, followed by adding toluene or benzene, and refluxing to produce isocyanate of formula (19):

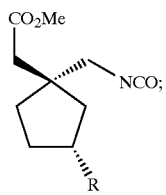

l) adding the product of Step k) to a mixture of a solvent selected from toluene, benzene, xylenes, and n-heptane, and methanol, and stirring at a temperature from 0° C. to 150° C. to produce the carbamate of formula (20):

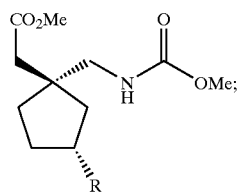

m) adding the product of Step l) to a mixture of a solvent selected from water, acetic acid, and 1,4-dioxane, and aqueous hydrochloric acid at a concentration of from 0.01 M to 12 M, and stirring at a temperature from 0° C. to 115° C. to produce a compound of formula IIa

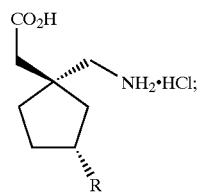

and n) converting the product of Step m) to a compound of Formula II:

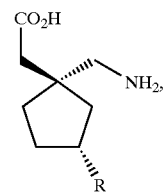

and farther converting, if desired, to a pharmaceutically acceptable salt by known means.

11. A process according to claim 9 which comprises:

a) adding a cyanoacetate of formula (A):

wherein $R_1$ is ethyl, to a mixture of a chiral cyclopentanone of formula (1):

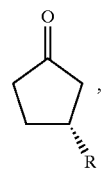

toluene, acetic acid, and a Knoevenagel reaction catalyst which is ammonium acetate, and heating the mixture at reflux over a Dean-Stark trap to produce the alkene of formula (2):

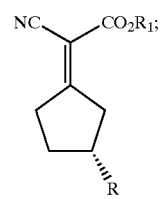

b) adding the product of Step a) above to a mixture of benzylmagnesium chloride in dry tetrahydrofuran at −100° C. to 25° C. to produce the addition products of formulas (3a):

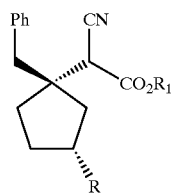

and (3b):

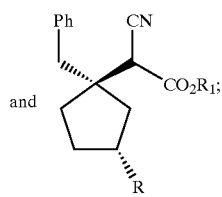

c) adding the products of Step b) above to a mixture of potassium hydroxide in ethylene glycol and heating the mixture at 100° C. to 200° C., and then acidifying to produce the hydrolysis products of formulas (4a):

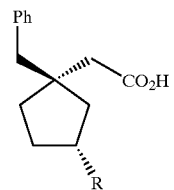

and (4b):

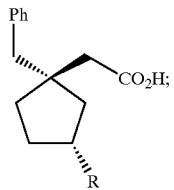

d) contacting the products of Step c) above with (S)-α-methyl-benzylamine in ethyl acetate, and recrystallizing the salt so formed from ethyl acetate to produce the enriched diastereomer of formula (5):

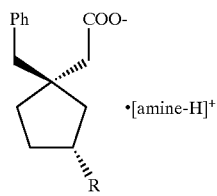

as the (S)-α-methyl-benzylamine salt;

e) adding the product of Step d) to aqueous hydrochloric acid and stirring to produce the carboxylic acid of formula (6):

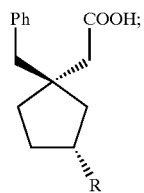

f) adding oxalyl chloride to a mixture of the product of Step e), dichloromethane, and a catalytic amount of N,N-dimethylformamide (DMF), and stirring to produce the acid chloride of formula (14):

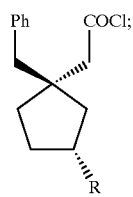

g) adding the product of Step i) to a mixture of tert-butyl alcohol, dichloromethane, and N-diisopropylethylamine (DIPEA), and stirring to produce the ester of formula (15):

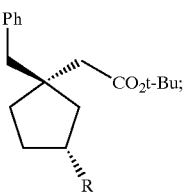

h) adding the product of Step g) to a mixture of carbon tetrachloride or ethyl acetate, and acetonitrile, water, sodium periodate, and ruthenium(III) chloride, and stirring to produce the carboxylic acid of formula (16):

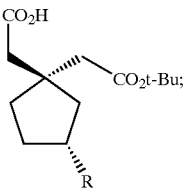

i) adding the product of Step h) to a mixture of methanol, toluene, and (trimethylsilyl)diazomethane, and stirring to produce the bis ester of formula (17):

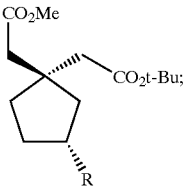

or adding the product of Step h) to a mixture of iodomethane, dichloromethane, triethylamine, and stirring to produce the bis ester of formula (17):

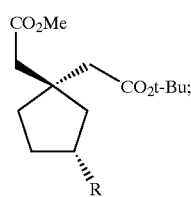

j) adding hydrochloric acid or trifluoroacetic acid (TFA) to a mixture of the product from Step i) and dichloromethane, and stirring to produce the carboxylic acid of formula (18):

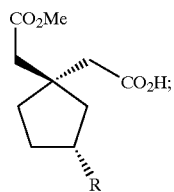

k) adding the product of Step j) to a mixture of triethylamine, toluene, and diphenylphosphoryl azide (DPPA), and refluxing to produce the isocyanate of formula (19):

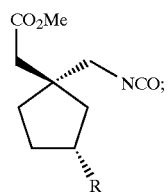

or adding the product of Step j) above to ethyl chloroformate or isobutyl chloroformate, triethylamine, and tetrahydrofuran at a temperature of from −40° C. to 78° C., followed by adding a solution of sodium azide in water and tetrahydrofuran or acetone, followed by adding toluene or benzene, and refluxing to produce isocyanate of formula (19):

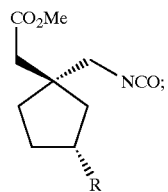

l) adding the product of Step k) to a mixture of methanol and toluene, and refluxing to produce the carbamate of formula (20):

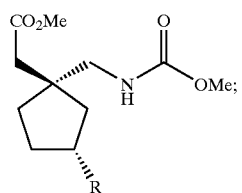

m) adding the product of Step l) to a mixture of 1,4-dioxane and aqueous hydrochloric acid at a concentration of 6 M, and stirring to produce a compound of formula IIa:

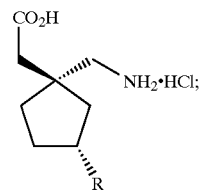

n) converting the product of Step m) to a compound of Formula II:

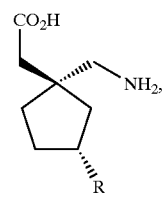

and further converting, if desired, to a pharmaceutically acceptable salt by known means.

12. A process according to claim 9, further characterized in that the intermediate product (14):

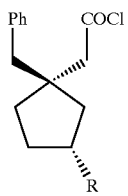

formed is further reacted, without isolation, with tert-butyl alcohol to produce the ester of formula (15):

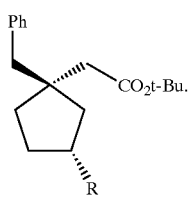

13. A process according to claim 9, characterized in that the intermediate product (19):

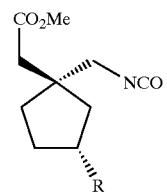

formed is further reacted, without isolation, with methanol to produce the carbamate of formula (20):

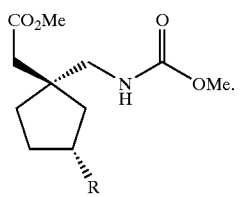

14. A process according to claim 9, characterized in that the intermediate product (14):

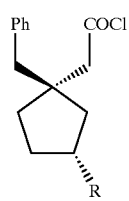

formed is further reacted, without isolation, with tert-butyl alcohol to produce the ester of formula (15):

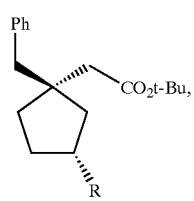

and the intermediate product (19):

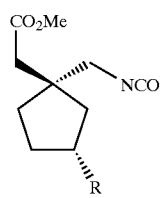

formed is further reacted, without isolation, with methanol to produce the carbamate of formula (20):

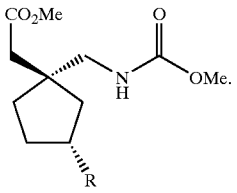

15. A process for the preparation of a compound of Formula III:

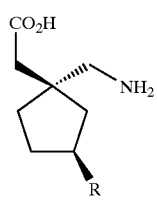

wherein R is $C_1$–$C_{10}$ alkyl or $C_3$–$C_{10}$ cycloalkyl, and pharmaceutically acceptable salts thereof, which comprises:

a) adding a cyanoacetate of formula (A):

wherein $R_1$ is alkyl or benzyl, to a mixture of a chiral cyclopentanone of formula (21):

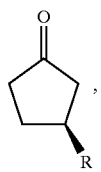

a solvent, a carboxylic acid, and a Knoevenagel reaction catalyst, and stirring the mixture in the presence of a means of removing water to produce the alkene of formula (22):

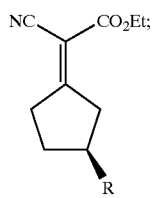

b) adding the product of Step a) above to a mixture of benzylmagnesium chloride or benzylmagnesium iodide, in a solvent to produce the addition of products of formulas (23a):

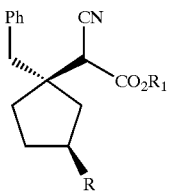

and (23b)

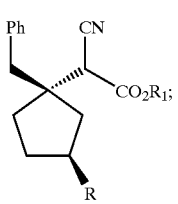

c) adding the products of Step b) above to a mixture of a base selected from potassium hydroxide, sodium hydroxide, lithium hydroxide, and cesium hydroxide, in a solvent, and stirring, and then acidifying to produce the carboxylic acids of formulas (24a):

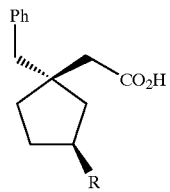

and (24b):

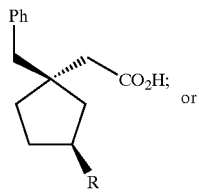
or or adding the products of Step b) above to an acid mixture, and stirring to produce the carboxylic acids of formulas (24a):

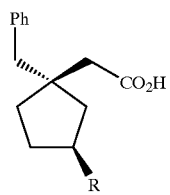

and (24b):

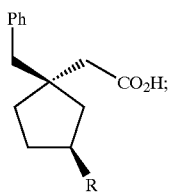

d) contacting the products of Step c) above with an amine in a solvent, and recrystallizing the salt so formed to produce the enriched diastereomer of formula (25):

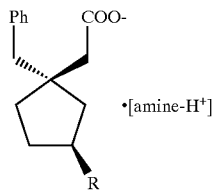

as the amine salt; and e) converting the product of Step d) to a carboxylic acid of formula (26):

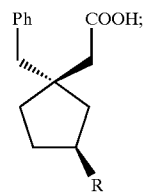

f) adding the product of Step e) to a mixture of iodomethane, a solvent, and 1,8-diazabicyclo[5.4.0]undec-7-ene (DBU), and stirring to produce the ester of formula (27):

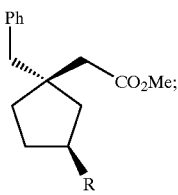

or adding the product of Step e) to methanol and an acid to produce the ester of formula (27):

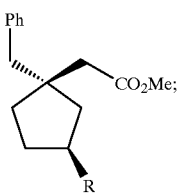

or adding the product of Step e) to a solution of diazomethane or trimethylsilyl-diazomethane in a solvent to produce ester of formula (27):

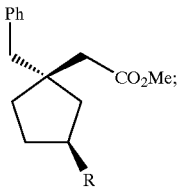

g) adding the product of Step f) to a mixture of carbon tetrachloride or ethyl acetate, and acetonitrile, water, sodium periodate, and ruthenium(III) chloride, and stirring to produce the carboxylic acid of formula (28):

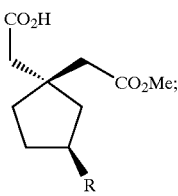

h) adding the product of Step g) to a mixture of a tertiary amine base, a solvent, and diphenylphosphoryl azide (DPPA), and stirring to produce the isocyanate of formula (29):

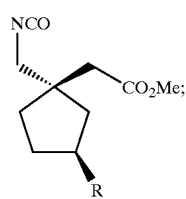

or adding the product of Step g) above to ethyl chloroformate or isobutyl chloroformate and a base in a solvent at a temperature of from −40° C. to 78° C., followed by adding a solution of sodium azide in water and tetrahydrofuran or acetone, followed by adding toluene or benzene, and refluxing to produce isocyanate of formula (29):

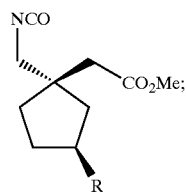

i) adding the product of Step h) to a mixture of a solvent and methanol, and stirring to produce the carbamate of formula (30):

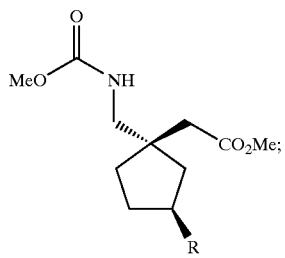

j) adding the product of Step i) to a mixture of a solvent and aqueous hydrochloric acid, and stirring to produce a compound of formula (IIIa):

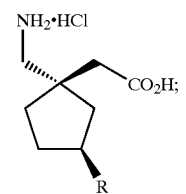

k) converting the product of Step j) to a compound of formula (III):

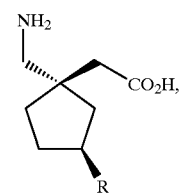

and further converting, if desired, to a pharmaceutically acceptable salt by known means.

16. A process for the preparation of a compound of Formula IV:

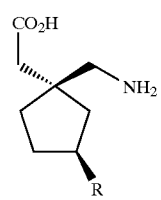

wherein R is $C_1$–$C_{10}$ alkyl or $C_3$–$C_{10}$ cycloalkyl, and pharmaceutically acceptable salts thereof, which comprises:

a) adding a cyanoacetate of formula (A):

wherein $R_1$ is alkyl or benzyl, to a mixture of a chiral cyclopentanone of formula (21):

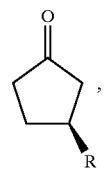

a solvent, a carboxylic acid, and a Knoevenagel reaction catalyst, and stirring the mixture in the presence of a means of removing water to produce the alkene of formula (22):

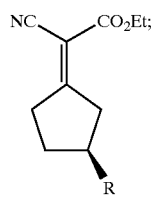

b) adding the product of Step a) above to a mixture of benzylmagnesium chloride or benzylmagnesium iodide, in a solvent to produce the addition of products of formulas (23a):

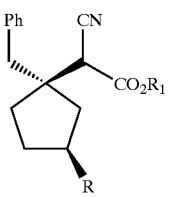

and (23b):

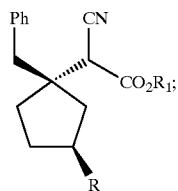

c) adding the products of Step b) above to a mixture of a base selected from potassium hydroxide, sodium hydroxide, lithium hydroxide, and cesium hydroxide, in a solvent, and stirring, and then acidifying to produce the carboxylic acids of formulas (24a):

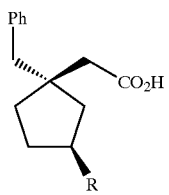

and (24b):

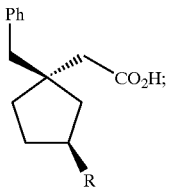

or adding the products of Step b) above to an acid mixture, and stirring to produce the carboxylic acids of formulas (24a):

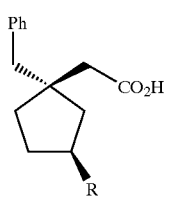

and (24b):

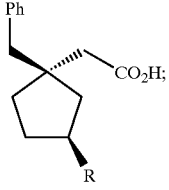

d) contacting the products of Step c) above with an amine in a solvent, and recrystallizing the salt so formed to produce the enriched diastereomer of formula (25):

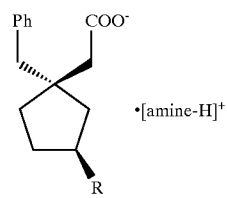

as the amine salt; and e) converting the product of Step d) to a carboxylic acid of formula (26):

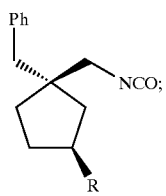

f) adding the product of Step e) to a mixture of a tertiary amine base, a solvent, and diphenylphosphoryl azide (DPPA) is added, and stirring to produce the isocyanate of formula (31):

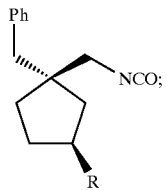

or adding the product of Step g) above to ethyl chloroformate or isobutyl chloroformate and a base in a solvent at a temperature of from −40° C. to 78° C., followed by adding a solution of sodium azide in water and tetrahydrofuran or acetone, followed by adding toluene or benzene, and refluxing to produce the isocyanate of formula (31):

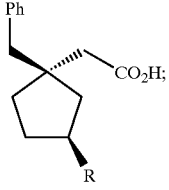

g) adding the product of Step f) to a mixture of a solvent and methanol, and stirring to produce the carbamate of formula (32):

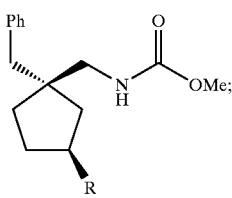

h) adding the product of Step g) to a mixture of carbon tetrachloride or ethyl acetate, and acetonitrile, water, sodium periodate, and ruthenium(III) chloride, and stirring to produce the carboxylic acid of formula (33):

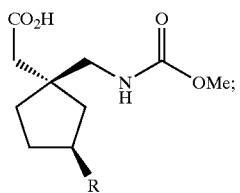

i) adding the product of Step h) to a mixture of a solvent and aqueous hydrochloric acid, and stirring to produce a compound of formula (IVa):

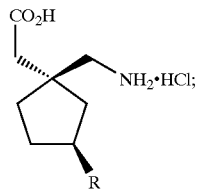

and j) converting the product of Step i) to a compound of formula (IV):

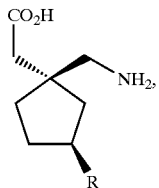

and further converting, if desired, to a pharmaceutically acceptable salt by known means.

17. A process for the preparation of a compound of Formula IV:

IV

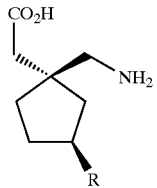

wherein R is $C_1$–$C_{10}$ alkyl or $C_3$–$C_{10}$ cycloalkyl, and pharmaceutically acceptable salts thereof, which comprises:

a) adding a cyanoacetate of formula (A):

wherein $R_1$ is alkyl or benzyl, to a mixture of a chiral cyclopentanone of formula (21):

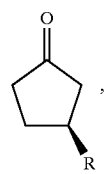

a solvent, a carboxylic acid, and a Knoevenagel reaction catalyst, and stirring the mixture in the presence of a means of removing water to produce the alkene of formula (22):

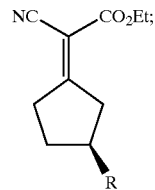

b) adding the product of Step a) above to a mixture of benzylmagnesium chloride or benzylmagnesium iodide, in a solvent to produce the addition of products of formulas (23a):

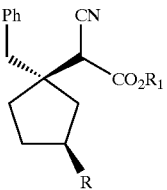

and (23b)

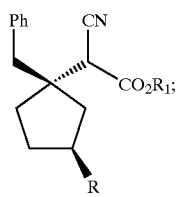

c) adding the products of Step b) above to a mixture of a base selected from potassium hydroxide, sodium hydroxide, lithium hydroxide, and cesium hydroxide, in a solvent, and stirring, and then acidifying to produce the carboxylic acids of formulas (24a):

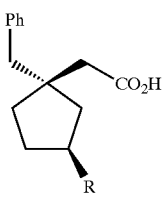

and (24b):

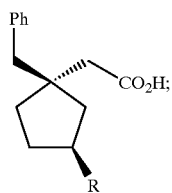

or adding the products of Step b) above to an acid mixture, and stirring to produce the carboxylic acids of formulas (24a):

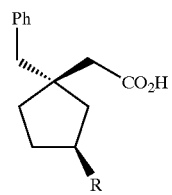

and (24b):

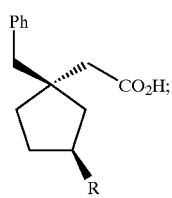

d) contacting the products of Step c) above with an amine in a solvent, and recrystallizing the salt so formed to produce the enriched diastereomer of formula (25):

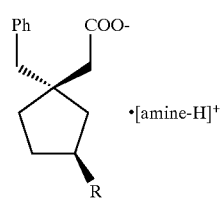

as the amine salt; and e) converting the product of Step d) to a carboxylic acid of formula (26):

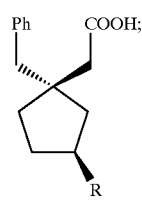

f) adding oxalyl chloride to a mixture of the product of Step e), a solvent, and N,N-dimethylformamide (DMF), and stirring to produce the acid chloride of formula (34):

g) adding the product of Step f) to a mixture of tert-butyl alcohol, a solvent, and a tertiary amine base, and stirring to produce the ester of formula (35):

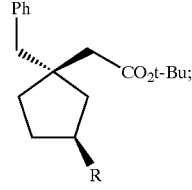

h) adding the product of Step g) to a mixture of carbon tetrachloride or ethyl acetate, and acetonitrile, water, sodium periodate, and ruthenium(III) chloride, and stirring to produce the carboxylic acid of formula (36):

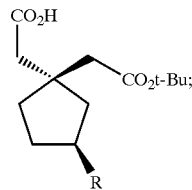

i) adding the product of Step h) to a mixture of a solvent, methanol, and (trimethylsilyl)diazomethane, and stirring to produce the bis ester of formula (37):

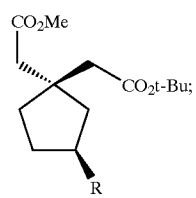

or adding the product of Step h) to a mixture of iodomethane, a solvent, and a base, and stirring to produce the bis ester of formula (37):

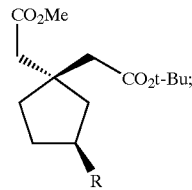

j) adding an acid to a mixture of the product from Step i) and a solvent and stirring to produce the carboxylic acid of formula (38):

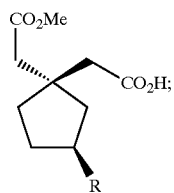

k) adding the product of Step j) to a mixture of a tertiary amine base, a solvent, and diphenylphosphoryl azide (DPPA), and stirring to produce the isocyanate of formula (39):

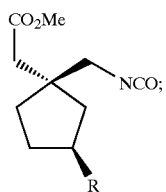

or adding the product of Step j) above to ethyl chloroformate or isobutyl chloroformate and a base in a solvent at a temperature of from −40° C. to 78° C., followed by adding a solution of sodium azide in water and tetrahydrofuran or acetone, followed by adding toluene or benzene, and refluxing to produce isocyanate of formula (39):

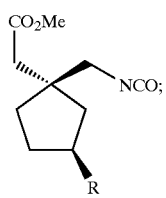

l) adding the product of Step k) to a mixture of a solvent and methanol, and stirring to produce the carbamate of formula (40):

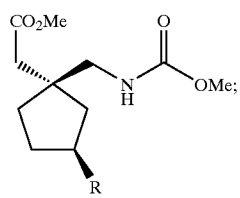

m) adding the product of Step l) to a mixture of a solvent and hydrochloric acid, and stirring to produce a compound of formula (IVa):

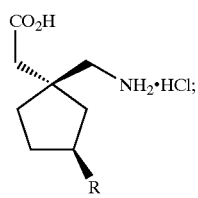

n) converting the product of Step m) to a compound of Formula IV:

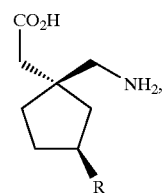

and further converting, if desired, to a pharmaceutically acceptable salt by known means.

18. A process for the preparation of a compound of formula (6):

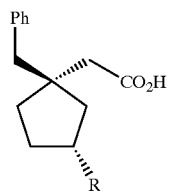

wherein R is $C_1$–$C_{10}$ alkyl or $C_3$–$C_{10}$ cycloalkyl, and pharmaceutically acceptable salts thereof, which comprises:

a) adding a cyanoacetate of formula (A):

wherein $R_1$ is alkyl or benzyl, to a mixture of a chiral cyclopentanone of formula (1):

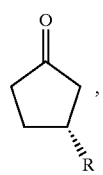

a solvent, a carboxylic acid, and a Knoevenagel reaction catalyst, and stirring the mixture in the presence of a means of removing water to produce the alkene of formula (2):

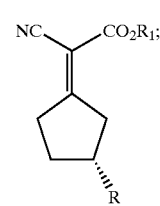

b) adding the product of Step a) above to a mixture of benzylmagnesium chloride, benzylmagnesium bromide, or benzylmagnesium iodide, in a solvent to produce the addition products of formulas (3a):

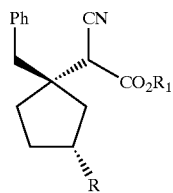

and (3b):

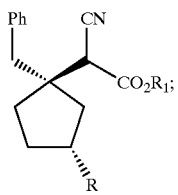

c) adding the products of Step b) above to a mixture of a base selected from potassium hydroxide, sodium hydroxide, lithium hydroxide, and cesium hydroxide, and a solvent, and stirring, and then acidifying to produce the carboxylic acids of formulas (4a):

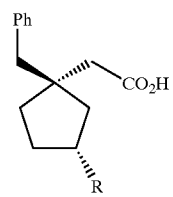

and (4b):

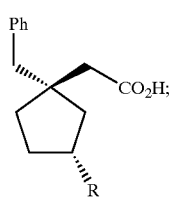

or adding the products of Step b) above to an acid mixture and stirring to produce the carboxylic acids of formulas (4a):

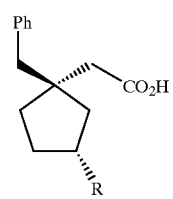

and (4b):

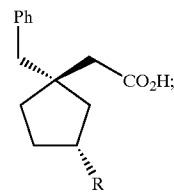

d) contacting the products of Step c) above with an amine in a solvent, and recrystallizing the salt so formed to produce the enriched diastereomer of formula (5):

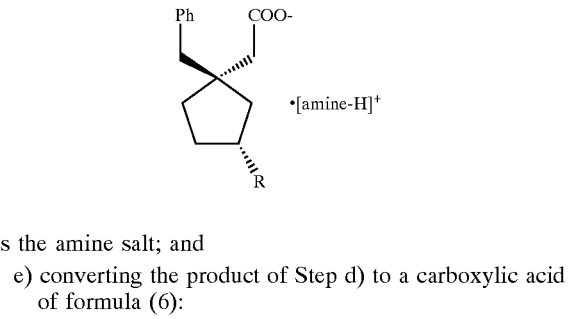

as the amine salt; and e) converting the product of Step d) to a carboxylic acid of formula (6):

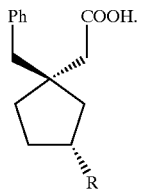

19. A process according to claim 18 which comprises:

a) adding a cyanoacetate of formula (A):

wherein $R_1$ is selected from methyl, ethyl, n-propyl, iso-propyl, n-butyl, iso-butyl, sec-butyl, tert-butyl, and benzyl to a mixture of a chiral cyclopentanone of formula (1):

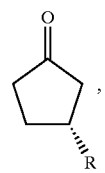

a solvent selected from tetrahydrofuran, 1,4-dioxane, tert-butylmethylether, chloroform, dichloromethane, acetonitrile, ethyl ether, ethyl acetate, hexanes, N,N-dimethylformamide, dimethylsulfoxide, ethanol, tert-butanol, toluene, benzene, xylenes, and n-heptane, acetic acid, and a Knoevenagel reaction catalyst selected from β-alanine, ammonium acetate, and piperidine, and stirring the mixture in the presence of a means of removing water selected from azeotropic distillation, activated molecular sieves, anhydrous magnesium sulfate, anhydrous sodium sulfate, anhydrous sodium carbonate, anhydrous potassium carbonate, anhydrous cesium carbonate, trimethyl orthoformate, and triethyl orthoformate to produce the alkene of formula (2):

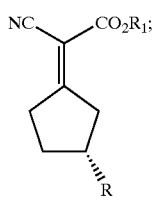

b) adding the product of Step a) above to a mixture of benzylmagnesium chloride, benzylmagnesium bromide, or benzylmagnesium iodide in a solvent selected from tetrahydrofuran, benzene, 1,4-dioxane, hexanes, n-heptane, toluene, diethyl ether, and tert-butyl methyl ether to produce the addition products of formulas (3a):

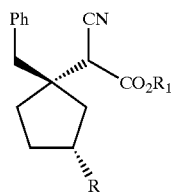

and (3b):

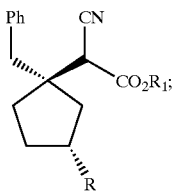

c) adding the products of Step b) above to a mixture of a base selected from potassium hydroxide, sodium hydroxide, lithium hydroxide, and cesium hydroxide in a solvent selected from ethylene glycol, 2-methoxyethyl ether, 1,4-dioxane, and diethylene glycol, and stirring the mixture, and then acidifying to produce the carboxylic acids of formulas (4a):

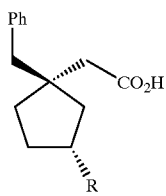

and (4b):

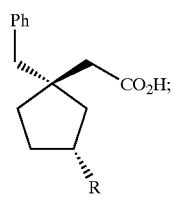

or adding the products of Step b) above to an acid mixture selected from 6–12 M HCl, 12 M $H_2SO_4$, 10%–48% wt/wt hydrobromic acid, and HBr in aqueous acetic acid, and stirring to produce the carboxylic acids of formulas (4a):

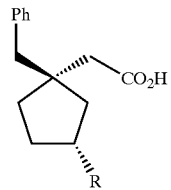

and (4b):

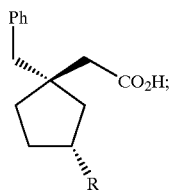

d) contacting the products of Step c) above with an amine selected from (S)-α-methyl-benzylamine, (R)-α-methyl-benzylamine, (R)-(+)-1-(naphthyl)ethylamine, (S)-(+)-1-(naphthyl)ethylamine, triethylamine, diisopropylethylamine, dicyclohexylamine, benzylamine, dibenzylamine, morpholine, N-methylmorpholine, piperidine, N-methylpiperidine, and pyridine in a solvent selected from N,N-dimethylformamide, chloroform, benzene, xylenes, hexanes, acetone, ethanol, methanol, iso-propanol, diethyl ether, dichloromethane, benzene, toluene, n-pentane, n-hexane, n-heptane, ethyl acetate, acetonitrile, tert-butyl methyl ether, tetrahydrofuran, and 1,4-dioxane, and recrystallizing the salt so formed to produce the enriched diastereomer of formula (5):

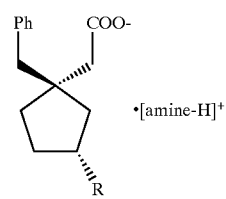

as the amine salt; and e) adding the product of Step d) to a mixture selected from aqueous hydrochloric acid, aqueous sulfuric acid, aqueous acetic acid, hydrochloric acid dissolved in acetic acid, and hydrochloric acid dissolved in acetic acid and water, and stirring to produce the carboxylic acid of formula (6):

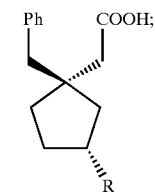

or partitioning the product of Step d) between a mixture of aqueous hydrochloric acid and a solvent selected from chloroform, dichloromethane, ethyl acetate, ethyl ether, tetrahydrofuran, 1,4-dioxane, toluene, and tert-butylmethylether, and drying and evaporating the organic layer to produce the carboxylic acid of formula (6):

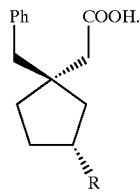

20. A process according to claim 18 which comprises:
a) adding a cyanoacetate of formula (A)

wherein $R_1$ is ethyl, to a mixture of a chiral cyclopentanone of formula (1):

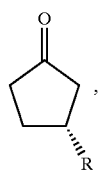

toluene, acetic acid, and a Knoevenagel reaction catalyst which is ammonium acetate, and heating the mixture at reflux over a Dean-Stark trap to produce the alkene of formula (2):

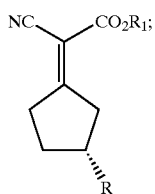

b) adding the product of Step a) above to a mixture of benzylmagnesium chloride in dry tetrahydrofuran at −100° C. to 25° C. to produce the addition products of formulas (3a):

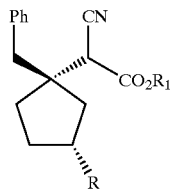

and (3b):

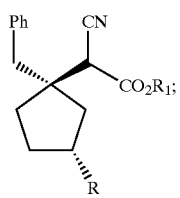

c) adding the products of Step b) above to a mixture of potassium hydroxide in ethylene glycol, and heating the mixture at 100° C. to 200° C., and then acidifying to produce the hydrolysis products of formulas (4a):

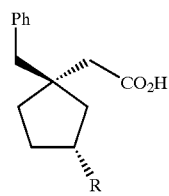

and (4b):

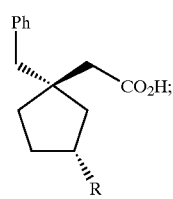

d) contacting the products of Step c) above with (S)-α-methyl-benzylamine in ethyl acetate, and recrystallizing the salt so formed from ethyl acetate to produce the enriched diastereomer of formula (5):

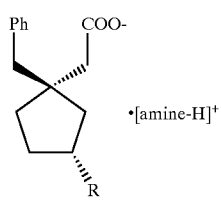

(S)-α-methyl-benzylamine salt;

e) adding the product of Step d) to aqueous hydrochloric acid and stirring to produce the carboxylic acid of formula (6):

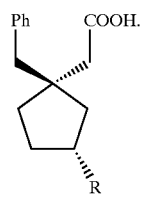

21. A process for the preparation of a compound of formula (26):

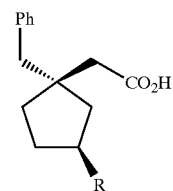

wherein R is $C_1$–$C_{10}$ alkyl or $C_1$–$C_{10}$ cycloalkyl, and pharmaceutically acceptable salts thereof, which comprises:

a) adding a cyanoacetate of formula (A):

wherein $R_1$ is alkyl or benzyl, to a mixture of a chiral cyclopentanone of formula (21):

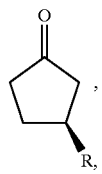

a solvent, a carboxylic acid, and a Knoevenagel reaction catalyst, and stirring the mixture in the presence of a means of removing water to produce the alkene of formula (22):

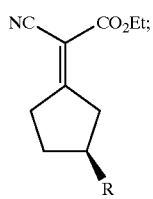

b) adding the product of Step a) above to a mixture of benzylmagnesium chloride or benzylmagnesium iodide, in a solvent to produce the addition of products of formulas (23a):

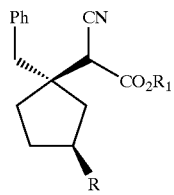

and (23b):

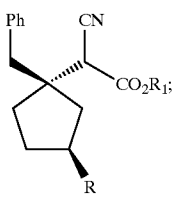

c) adding the products of Step b) above to a mixture of a base selected from potassium hydroxide, sodium hydroxide, lithium hydroxide, and cesium hydroxide, and a solvent, and stirring, and then acidifying to produce the carboxylic acids of formulas (24a):

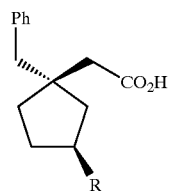

and (24b):

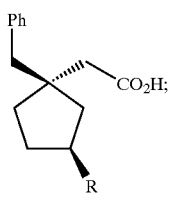

or adding the products of Step b) above to an acid mixture, and stirring to produce the carboxylic acids of formulas (24a):

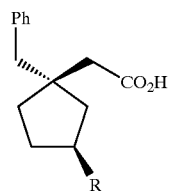

and (24b):

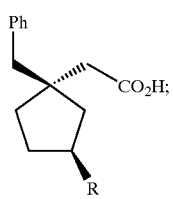

d) contacting the products of Step c) above with an amine in a solvent, and recrystallizing the salt so formed to produce the enriched diastereomer of formula (25):

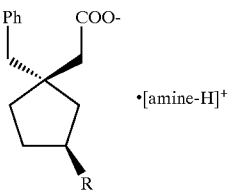

as the amine salt; and e) converting the product of Step d) to a carboxylic acid of formula (26):

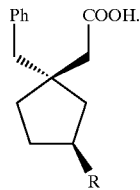

22. A process according to claim 21 which comprises:
a) adding a cyanoacetate of formula (A):

wherein $R_1$ is selected from methyl, ethyl, n-propyl, iso-propyl, n-butyl, iso-butyl, sec-butyl, tert-butyl, and benzyl, to a mixture of a chiral cyclopentanone of formula (21):

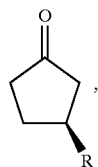

a solvent selected from tetrahydrofuran, 1,4-dioxane, tert-butylmethylether, chloroform, dichloromethane, acetonitrile, ethyl ether, ethyl acetate, hexanes, N,N-dimethylformamide, dimethylsulfoxide, ethanol, tert-butanol, toluene, benzene, xylenes, and n-heptane, acetic acid, and a Knoevenagel reaction catalyst selected from β-alanine, ammonium acetate, and piperidine, and stirring the mixture in the presence of a means of removing water selected from azeotropic distillation, activated molecular sieves, anhydrous magnesium sulfate, anhydrous cesium carbonate, trimethyl orthoformate, and triethyl orthoformate to produce the alkene of formula (22):

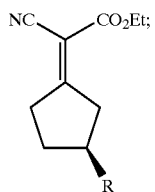

b) adding the product of Step a) above to a mixture of benzylmagnesium chloride, benzylmagnesium bromide, or benzylmagnesium iodide in a solvent selected from tetrahydrofuran, 1,4-dioxane, hexanes, n-heptane, toluene, diethyl ether, and tert-butyl methyl ether to produce the addition products of formulas (23a):

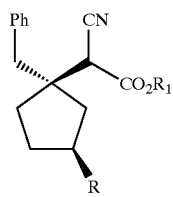

and (23b):

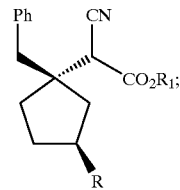

c) adding the products of Step b) above to a mixture of a base selected from potassium hydroxide, sodium hydroxide, lithium hydroxide, and cesium hydroxide in a solvent selected from ethylene glycol, 2-methoxyethyl ether, 1,4-dioxane, and diethylene glycol, and stirring the mixture, and then acidifying to produce the carboxylic acids of formulas (24a):

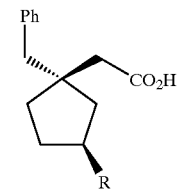

and (24b):

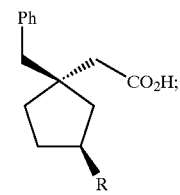

or adding the products of Step b) above to an acid mixture selected from 6–12 M HCl, 12 M $H_2SO_4$, 10%–48% wt/wt hydrobromic acid, and HBr in aqueous acetic acid, and stirring to produce the carboxylic acids of formulas (24a):

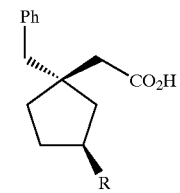

and (24b):

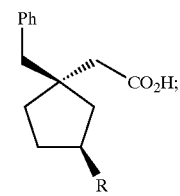

d) contacting the products of Step c) above with an amine selected from (S)-α-methyl-benzylamine, (R)-α-methyl-benzylamine, (R)-(+)-1-(naphthyl)ethylamine, (S)-(+)-1-(naphthyl)ethylamine, triethylamine, diisopropylethylamine, dicyclohexylamine, benzylamine, dibenzylamine, morpholine, N-methylmorpholine, piperidine, N-methylpiperidine, and pyridine in a solvent selected from N,N-dimethylformamide, chloroform, hexanes, acetone, ethanol, methanol, iso-propanol, diethyl ether, dichloromethane, benzene, toluene, n-pentane, n-hexane, n-heptane, ethyl acetate, acetonitrile, tert-butyl methyl ether, tetrahydrofuran, and 1,4-dioxane, and recrystallizing the salt so formed to produce the enriched diastereomer of formula (25):

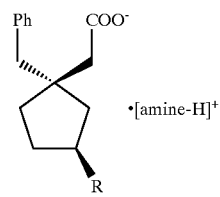

as the amine salt; and e) adding the product of Step d) to a mixture selected from aqueous hydrochloric acid, aqueous sulfuric acid, aqueous acetic acid, hydrochloric acid dissolved in acetic acid, and hydrochloric acid dissolved in acetic acid and water, and stirring to produce the carboxylic acid of formula (26):

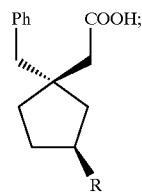

or partitioning the product of Step d) between a mixture of aqueous hydrochloric acid and a solvent selected from chloroform, dichloromethane, ethyl acetate, ethyl ether, tetrahydrofuran, 1,4-dioxane, toluene, and tert-butylmethylether, and drying and evaporating the organic layer to produce the carboxylic acid of formula (26):

23. A process according to claim 21 which comprises:

a) adding a cyanoacetate of formula (A):

wherein $R_1$ is ethyl, to a mixture of a chiral cyclopentanone of formula (21):

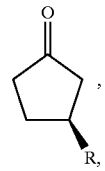

toluene, acetic acid, and a Knoevenagel reaction catalyst which is ammonium acetate, and heating the mixture at reflux over a Dean-Stark trap to produce the alkene of formula (22):

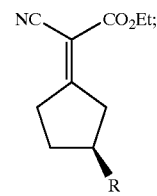

b) adding the product of Step a) above to a mixture of benzylmagnesium chloride in dry tetrahydrofuran at −100° C. to −20° C. to produce the addition products of formulas (23a):

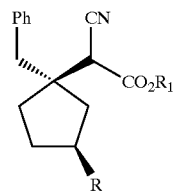

and (23b):

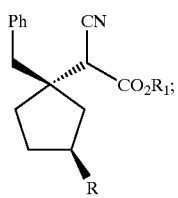

c) adding the products of Step b) above to a mixture of potassium hydroxide in ethylene glycol, and heating the mixture at 100° C. to 200° C., and then acidifying to produce the hydrolysis products of formula (24a):

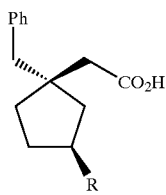

and (24b):

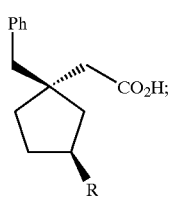

d) contacting the products of Step c) above with (R)-α-methyl-benzylamine in ethyl acetate, and recrystallizing the salt so formed from ethyl acetate to produce the enriched diastereomer of formula (25):

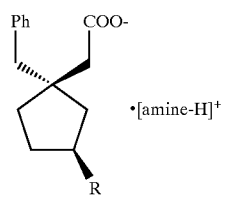

as the (R)-α-methyl-benzylamine salt; and e) adding the product of Step d) to aqueous hydrochloric acid and stirring to produce the carboxylic acid of formula (26):

24. A compound of formula (6):

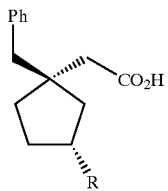

wherein R is $C_1$–$C_{10}$ alkyl or $C_3$–$C_{10}$ cycloalkyl, and pharmaceutically acceptable salts thereof.

25. A compound according to claim 24 wherein R is $C_1$–$C_{10}$ alkyl.

26. A compound according to claim 24 wherein R is selected from methyl, ethyl, and n-propyl.

27. A compound according to claim 24 named ((1S,3R)-1-benzyl-3-methyl-cyclopentyl)-acetic acid.

28. A compound of formula (26):

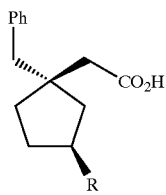

wherein R is $C_1$–$C_{10}$ alkyl or $C_3$–$C_{10}$ cycloalkyl and pharmaceutically acceptable salts thereof.

29. A compound according to claim 28 wherein R is $C_1$–$C_{10}$ alkyl.

30. A compound according to claim 28 wherein R is selected from methyl, ethyl, and n-propyl.

31. A compound according to claim 28 named ((1R,3S)-1-benzyl-3-methyl-cyclopentyl)-acetic acid.

32. A compound of formula (6):

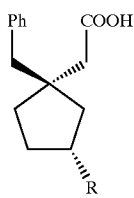

wherein R is $C_1$–$C_{10}$ alkyl or $C_3$–$C_{10}$ cycloalkyl and pharmaceutically acceptable salts thereof, prepared according to the process of claim 18.

33. A compound of formula (6)

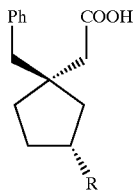

wherein R is $C_1$–$C_{10}$ alkyl or $C_3$–$C_{10}$ cycloalkyl and pharmaceutically acceptable salts thereof, prepared according to the process of claim 19.

34. A compound of formula (6)

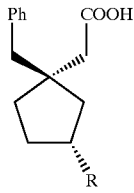

wherein R is $C_1$–$C_{10}$ alkyl or $C_3$–$C_{10}$ cycloalkyl and pharmaceutically acceptable salts thereof, prepared according to the process of claim 20.

35. A compound of formula (26)

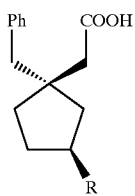

wherein R is $C_1$–$C_{10}$ alkyl or $C_3$–$C_{10}$ cycloalkyl and pharmaceutically acceptable salts thereof, prepared according to the process of claim 21.

36. A compound of formula (26)

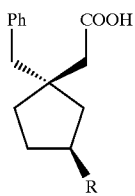

wherein R is $C_1$–$C_{10}$ alkyl or $C_3$–$C_{10}$ cycloalkyl and pharmaceutically acceptable salts thereof, prepared according to the process of claim 22.

37. A compound of formula (26)

wherein R is $C_1$–$C_{10}$ alkyl or $C_3$–$C_{10}$ cycloalkyl and pharmaceutically acceptable salts thereof, prepared according to the process of claim 23.

38. A compound selected from:
E-Cyano-((R)-3-methyl-cyclopentylidene)-acetic acid ethyl ester;
Z-Cyano-((R)-3-methyl-cyclopentylidene)-acetic acid ethyl ester;
(R)-((1S,3R)-1-Benzyl-3-methyl-cyclopentyl)-cyano-acetic acid ethyl ester;
(S)-((1S,3R)-1-Benzyl-3-methyl-cyclopentyl)-cyano-acetic acid ethyl ester;
(R)-((1R,3R)-1-Benzyl-3-methyl-cyclopentyl)-cyano-acetic acid ethyl ester;
(S)-((1R,3R)-1-Benzyl-3-methyl-cyclopentyl)-cyano-acetic acid ethyl ester;
((1S,3R)-1-Isocyanatomethyl-3-methyl-cyclopentylmethyl)-benzene;
((1S,3R)-1-Benzyl-3-methyl-cyclopentylmethyl)-carbamic acid methyl ester;
[(1S,3R)-1-(Methoxycarbonylamino-methyl)-3-methyl-cyclopentyl]-acetic acid;
((1S,3R)-1-Benzyl-3-methyl-cyclopentyl)-acetic acid methyl ester;
(1S,3R)-1-Methoxycarbonylmethyl-3-methyl-cyclopentyl)-acetic acid;
((1R,3R)-1-Isocyanatomethyl-3-methyl-cyclopentyl)-acetic acid methyl ester;
[(1R,3R)-1-(Methoxycarbonylamino-methyl)-3-methyl-cyclopentyl]-acetic acid methyl ester;
((1S,3R)-1-Benzyl-3-methyl-cyclopentyl)-acetic acid tert-butyl ester;
[(1S,3R)-1-Carboxymethyl-3-methyl-cyclopentyl]-acetic acid tert-butyl ester;
[(1S,3R)-1-Methoxycarbonylmethyl-3-methyl-cyclopentyl]-acetic acid tert-butyl ester;
((1R,3R)-1-Methoxycarbonylmethyl-3-methyl-cyclopentyl)-acetic acid;
((1S,3R)-1-Isocyanatomethyl-3-methyl-cyclopentyl)-acetic acid methyl ester; and
[(1S,3R)-1-(Methoxycarbonylamino-methyl)-3-methyl-cyclopentyl]-acetic acid methyl ester.

39. A process for the preparation of a compound of formula (4a):

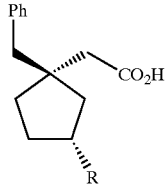

wherein R is $C_1$–$C_{10}$ alkyl or $C_3$–$C_{10}$ cycloalkyl, comprising, hydrolyzing a compound of formula (3a):

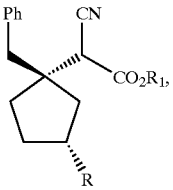

wherein $R_1$ is H, alkyl, or benzyl.

40. A process for the preparation of a compound of formula (24a):

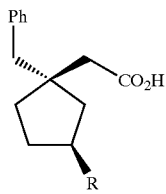

wherein R is $C_1$–$C_{10}$ alkyl or $C_3$–$C_{10}$ cycloalkyl, comprising, hydrolyzing a compound of formula (23a):

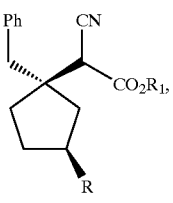

wherein $R_1$ is H, alkyl, or benzyl.

41. A process for the preparation of a compound of formula (6):

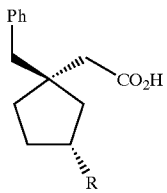

wherein R is $C_1$–$C_{10}$ alkyl or $C_3$–$C_{10}$ cycloalkyl, comprising, resolving a mixture containing compounds of formulas (4a):

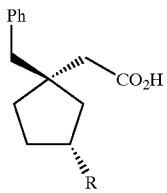

and (4b):

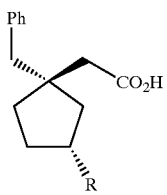

wherein R is $C_1$–$C_{10}$ alkyl or $C_3$–$C_{10}$ cycloalkyl.

42. A process for the preparation of a compound of formula (26):

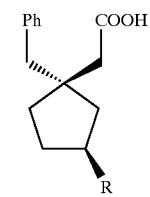

wherein R is $C_1$–$C_{10}$ alkyl or $C_3$–$C_{10}$ cycloalkyl, comprising, resolving a mixture containing compounds of formulas (24a):

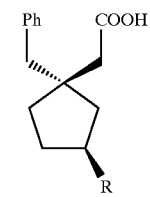

and (24b):

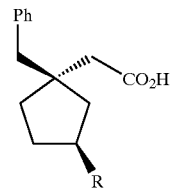

wherein R is $C_1$–$C_{10}$ alkyl or $C_3$–$C_{10}$ cycloalkyl.

43. A process for the preparation of a compound of Formula I:

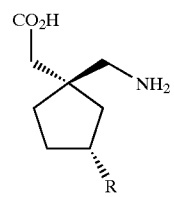

wherein R is $C_1$–$C_{10}$ alkyl or $C_3$–$C_{10}$ cycloalkyl, and a pharmaceutically acceptable salts thereof, comprising, hydrolyzing a compound of formula (41):

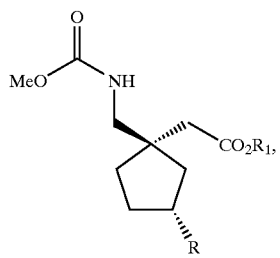

wherein $R_1$ is H, alkyl, or benzyl, and contacting the product, if desired, with an acid or a base.

44. A process for the preparation of a compound of Formula II:

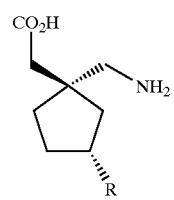

wherein R is $C_1$–$C_{10}$ alkyl or $C_3$–$C_{10}$ cycloalkyl, and a pharmaceutically acceptable salts thereof, comprising, hydrolyzing a compound of formula (42):

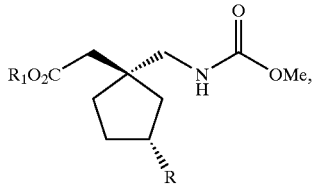

wherein $R_1$ is H, alkyl, or benzyl, and contacting the product, if desired, with an acid or a base.

45. A process for the preparation of a compound of Formula III:

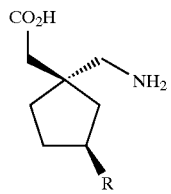

wherein R is $C_1$–$C_{10}$ alkyl or $C_3$–$C_{10}$ cycloalkyl, and pharmaceutically acceptable salts thereof; comprising, hydrolyzing a compound of formula (43):

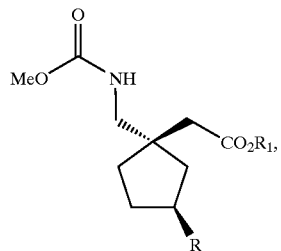

wherein $R_1$ is H, alkyl, or benzyl, and contacting the product, if desired, with an acid or a base.

46. A process for the preparation of a compound of Formula IV:

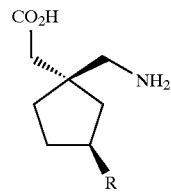

wherein R is $C_1$–$C_{10}$ alkyl or $C_3$–$C_{10}$ cycloalkyl, and pharmaceutically acceptable salts thereof, comprising, hydrolyzing a compound of formula (44):

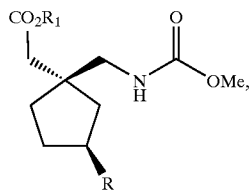

wherein $R_1$ is H, alkyl, or benzyl, and contacting the product, if desired, with an acid or a base.

* * * * *